US008735417B2

(12) United States Patent
Altman et al.

(10) Patent No.: US 8,735,417 B2
(45) Date of Patent: May 27, 2014

(54) AMINOPYRIMIDINES AS SYK INHIBITORS

(75) Inventors: Michael D. Altman, Needham, MA (US); Kenneth L. Arrington, Revere, MA (US); Jason Burch, Redwood City, CA (US); Bernard Cote, Notre-Dame-de-l'Ile-Perrot (CA); Jean-Francois Fournier, Juan les Pins (FR); Jacques Yves Gauthier, Laval des Rapides (CA); Solomon Kattar, Arlington, MA (US); Sandra Lee Knowles, Princeton, NJ (US); Jongwon Lim, Lexington, MA (US); Michelle R. Machacek, Brookline, MA (US); Alan B. Northrup, Reading, MA (US); Michael H. Reutershan, Brookline, MA (US); Joel S. Robichaud, Dollard des Ormeaux (CA); Adam J. Schell, Decatur, GA (US); Kerrie B. Spencer, Woonsocket, RI (US)

(73) Assignees: Merck Sharp & Dohme Corp., Rahway, NJ (US); Merck Canada Inc., Quebec (CA)

( * ) Notice: Subject to any disclaimer, the term of this patent is extended or adjusted under 35 U.S.C. 154(b) by 161 days.

(21) Appl. No.: 13/515,941

(22) PCT Filed: Dec. 16, 2010

(86) PCT No.: PCT/US2010/060703
§ 371 (c)(1),
(2), (4) Date: Jun. 14, 2012

(87) PCT Pub. No.: WO2011/075560
PCT Pub. Date: Jun. 23, 2011

(65) Prior Publication Data
US 2012/0309735 A1 Dec. 6, 2012

Related U.S. Application Data

(60) Provisional application No. 61/287,288, filed on Dec. 17, 2009.

(51) Int. Cl.
*A61K 31/506* (2006.01)
*C07D 417/02* (2006.01)

(52) U.S. Cl.
USPC .......... 514/275; 544/242; 544/322; 544/331; 514/247; 514/256

(58) Field of Classification Search
USPC .......... 544/242, 322, 331; 514/247, 256, 275
See application file for complete search history.

(56) References Cited

U.S. PATENT DOCUMENTS

| 7,449,458 | B2 | 11/2008 | Bhamidipati et al. |
| 7,485,724 | B2 | 2/2009 | Singh et al. |
| 7,538,108 | B2 | 5/2009 | Singh et al. |
| 7,557,210 | B2 | 7/2009 | Singh et al. |
| 8,158,641 | B2 * | 4/2012 | Djung et al. .......... 514/275 |
| 8,551,984 | B2 | 10/2013 | Altman et al. |
| 2004/0176271 | A1 | 9/2004 | Bethiel et al. |
| 2006/0030588 | A1 | 2/2006 | Stamford et al. |
| 2006/0205731 | A1 | 9/2006 | Kodama et al. |
| 2008/0139535 | A1 | 6/2008 | Anandan et al. |
| 2008/0221089 | A1 | 9/2008 | Argade et al. |
| 2008/0312251 | A1 | 12/2008 | Sun et al. |
| 2012/0277192 | A1 | 11/2012 | Altman et al. |
| 2013/0090309 | A1 | 4/2013 | Romeo et al. |

FOREIGN PATENT DOCUMENTS

| EP | 1854793 A1 | 11/2007 |
| WO | 02/096905 A1 | 12/2002 |
| WO | 02/102313 A2 | 12/2002 |
| WO | 2004/005283 A1 | 1/2004 |
| WO | 2004/087698 A2 | 10/2004 |
| WO | 2006/129100 A1 | 7/2006 |
| WO | 2007/117692 A2 | 10/2007 |
| WO | 2008/024634 A1 | 2/2008 |
| WO | 2008/073687 A2 | 6/2008 |
| WO | 2004/087699 A2 | 10/2008 |
| WO | 2008/137605 A1 | 11/2008 |
| WO | 2009/012421 A1 | 1/2009 |
| WO | 2009/032861 A1 | 3/2009 |
| WO | 2009/103032 A1 | 8/2009 |
| WO | 2009/122180 A1 | 10/2009 |
| WO | 2009/145856 A1 | 12/2009 |
| WO | 2011/075515 A1 | 6/2011 |
| WO | 2011/086085 A1 | 7/2011 |

OTHER PUBLICATIONS

Pearce, et al., "Failure modes in anticancer drug discovery and development," Cancer Drug Design and Discovery, 2008, Edited by Stephen Neidle, Chapter 18, pp. 424-435.
Johnson, et al., "Relationships between drug activity in NCI preclinical in vitro and in vivo models and early clinical trials," British Journal of Cancer, (2001), vol. 84, No. 10, pp. 1424-1431.
Simone, J.V., "Oncology: Introduction," Cecil Textbook of Medicine, 20th Edition, 1996, vol. 1, pp. 1004-1010.
Gura, T., "Cancer models—Systems for identifying new drugs are often faulty," Science, Nov. 1997, vol. 278, No. 5340, pp. 1041-1042.
Pamuk et al., "Spleen tyrosine kinase inhibition in the treatment of autoimmune, allergic and autoinflammatory diseases," Arthritis Research & Therapy, 2010, vol. 12, No. 222, pp. 1-11.
Written Opinion issued Feb. 9, 2011 by the International Searching Authority in connection with PCT International No. PCT/US2010/060703, filed Dec. 16, 2010.
International Search Report issued Feb. 9, 2011 by the International Searching Authority in connection with PCT/US2010/060703, filed Dec. 16, 2010.

* cited by examiner

*Primary Examiner* — Golam M M Shameem
(74) *Attorney, Agent, or Firm* — Eric A. Meade; Valerie J. Camara

(57) ABSTRACT

The present invention provides novel pyrimidine amines of formula (I) which are potent inhibitors of spleen tyrosine kinase, and are useful in the treatment and prevention of diseases mediated by said enzyme, such as asthma, COPD and rheumatoid arthritis.

13 Claims, No Drawings

AMINOPYRIMIDINES AS SYK INHIBITORS

CROSS-REFERENCE TO RELATED APPLICATIONS

This Application is a U.S. National Stage Application under 35 U.S.C. §371 of PCT Application No. PCT/US2010/060703 filed Dec. 16, 2010 which claims priority under 35 U.S.C. §119(e) of U.S. Provisional Application No. 61/287,288 filed Dec. 17, 2009.

BACKGROUND OF THE INVENTION

Spleen Tyrosine Kinase (Syk) is a protein tyrosine kinase which has been described as a key mediator of immunoreceptor signalling in a host of inflammatory cells including mast cells, B-cells, macrophages and neutrophils. These immunoreceptors, including Fc receptors and the B-cell receptor, are important for both allergic diseases and antibody-mediated autoimmune diseases and thus pharmacologically interfering with Syk could conceivably treat these disorders.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE and IgG become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesized lipid mediators including prostaglandins and leukotrienes.

Syk kinase is a non-receptor linked tyrosine kinase which is important in transducing the downstream cellular signals associated with cross-linking Fc.epsilon.R1 and or Fc.epsilon.R1 receptors, and is positioned early in the signalling cascade. In mast cells, for example, the early sequence of Fc.epsilon.R1 signalling following allergen cross-linking of receptor-IgE complexes involves first Lyn (a Src family tyrosine kinase) and then Syk. Inhibitors of Syk activity would therefore be expected to inhibit all downstream signalling cascades thereby alleviating the immediate allergic response and adverse events initiated by the release of pro-inflammatory mediators and spasmogens (Wong et al 2004, Expert Opin. Investig. Drugs (2004) 13 (7) 743-762).

Recently, it has been shown that the Syk kinase inhibitor R112 (Rigel), dosed intranasally in a phase I/II study for the treatment of allergic rhinitis, gave a statistically significant decrease in PGD2, a key immune mediator that is highly correlated with improvements in allergic rhinorrhea, as well as being safe across a range of indicators, thus providing the first evidence for the clinical safety and efficacy of a topical Syk kinase inhibitor. (Meltzer, Eli O.; Berkowitz, Robert B.; Grossbard, Elliott B, Journal of Allergy and Clinical Immunology (2005), 115(4), 791-796). In a more recent phase II clinical trial for allergic rhinitis (Clinical Trials.gov Identifier NCT0015089), R112 was shown as having a lack of efficacy versus placebo.

Rheumatoid Arthritis (RA) is an auto-immune disease affecting approximately 1% of the population. It is characterised by inflammation of articular joints leading to debilitating destruction of bone and cartilage. Recent clinical studies with Rituximab, which causes a reversible B cell depletion, (J. C. W. Edwards et al 2004, New Eng. J. Med. 350: 2572-2581) have shown that targeting B cell function is an appropriate therapeutic strategy in auto-immune diseases such as RA. Clinical benefit correlates with a reduction in auto-reactive antibodies (or Rheumatoid Factor) and these studies suggest that B cell function and indeed auto-antibody production are central to the ongoing pathology in the disease.

Studies using cells from mice deficient in the Spleen Tyrosine Kinase (Syk) have demonstrated a non-redundant role of this kinase in B cell function. The deficiency in Syk is characterised by a block in B cell development (M. Turner et al 1995 Nature 379: 298-302 and Cheng et al 1995, Nature 378: 303-306). These studies, along with studies on mature B cells deficient in Syk (Kurasaki et al 2000, Immunol. Rev. 176:19-29), demonstrate that Syk is required for the differentiation and activation of B cells. Hence, inhibition of Syk in RA patients is likely block B cell function and thereby reduce Rheumatoid Factor production. In addition to the role of Syk in B cell function, and of further relevance to the treatment of RA, is the requirement for Syk activity in Fc receptor (FcR) signalling. FcR activation by immune complexes in RA has been suggested to contribute to the release of multiple pro-inflammatory mediators.

The present invention relates to novel compounds, which are inhibitors of Syk kinase activity. These compounds therefore have potential therapeutic benefit in the treatment of disorders associated with inappropriate Syk activity, in particular in the treatment and prevention of disease states mediated by Syk. Such disease states may include inflammatory, allergic and autoimmune diseases, for example, asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, idiopathic thrombocytopenic purpura (ITP), multiple sclerosis, cancer, HIV and lupus.

SUMMARY OF THE INVENTION

The present invention provides novel compounds that are potent inhibitors of SYK as well as pharmaceutical compositions containing them. As SYK inhibitors compounds of the present invention are useful in the treatment and prevention of diseases and disorders mediated by the SYK protein; such diseases and disorders include, but are not limited to, asthma, COPD, rheumatoid arthritis and idiopathic thrombocytopenic purpura.

DETAILED DESCRIPTION OF THE INVENTION

The present invention provides compounds of formula I and pharmaceutically acceptable salts thereof:

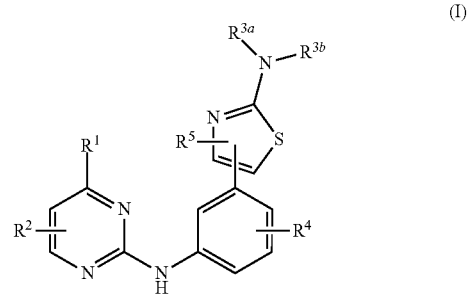

(I)

wherein
R¹ is selected from the group consisting of (a) hydrogen, (b) halogen, (c) CN, (d) $C_{1-6}$ alkyl optionally substituted with one or more groups independently selected from the group consisting of $OR^a$ and halogen, (e) $C_{2-6}$ alkenyl, (f) $C_{2-6}$ alkynyl, (g) $C_{3-6}$ cycloalkyl, (h) OH, (i) —O—$C_{1-6}$ alkyl optionally substituted with one or more groups independently selected from (i) aryl, (ii) 5- or 6-membered heteroaryl optionally substituted with one or more groups independently selected from $C_{1-6}$ alkyl, (iii) 4- to 8-membered heterocyclyl optionally substituted with one or more groups independently selected from oxo, halogen, $C_{1-6}$ alkyl, (iv) —$CO_2R^a$, (v) —$CONR^bR^c$, (vi) —$NR^bR^c$, (vii) —NH-heterocycle optionally substituted with alkyl, and (viii) —$OR^a$, (j) —O—X, wherein X is selected from the group consisting of (i) 4- to 8-membered heterocyclyl optionally substituted with one or more groups independently selected from halogen, $C_{1-6}$ alkyl, —$C_{1-6}$ haloalkyl, $COR^a$, $CO_2R^a$, and (ii) $C_{3-6}$ cycloalkyl optionally substituted with one or more groups independently selected from $C_{1-6}$ alkyl, —$OR^a$, benzyl, —$CO_2R^a$, and —$NR^bR^c$, (k) —$S(O)_n$—$C_{1-6}$ alkyl optionally substituted with $OR^a$, (l) —$CO_2R^a$, (m) —$CONR^bR^c$, and (n) —$COR^a$;
R² is selected from the group consisting of (a) H, (b) halogen, (c) $C_{1-6}$ alkyl, (d) O—$C_{1-6}$ alkyl, (e) $C_{1-6}$ haloalkyl and (f) O—$C_{1-6}$ haloalkyl;
$R^{3a}$ and $R^{3b}$ are independently selected from the group consisting of (a) H, (b) $C_{1-8}$ alkyl optionally substituted with one or more groups independently selected from (i) $OR^a$, (ii) heteroaryl optionally substituted with $C_{1-4}$ alkyl, aryl, (iii) aryl optionally substituted with halogen, $C_{1-4}$ alkyl (optionally substituted with halogen, $CO_2R^a$, $NR^bR^c$), $CO_2R^a$, $OR^a$, $NR^bR^c$, heteroaryl, (iv) $NR^bR^c$, (v) halogen, (vi) heterocyclyl optionally substituted with oxo, $C_{1-4}$ alkyl, $OR^a$, $NR^bR^c$, (vii) $SR^a$, (viii) $C_{3-8}$ cycloalkyl optionally substituted with $OR^a$, $NR^bR^c$, and (ix) $CO_2R^a$, (c) heterocycle optionally substituted with one or more groups independently selected from $OR^a$, (d) $C_{3-8}$ cycloalkyl optionally substituted with one or more groups independently selected from $OR^a$, (e) $C_{3-6}$ alkenyl, (f) heteroaryl optionally substituted with one or more groups independently selected from $C_{1-4}$ alkyl optionally substituted with $NR^bR^c$, (g) —$SO_2R^a$, (h) —$C(O)CH_2OC(O)R^a$, (i) —$C(O)R^a$, (j) —$CO_2R^a$, (k) —$CONR^bR^c$, (l) aryl optionally substituted with $CO_2R^a$, or
$R^{3a}$, $R^{3b}$ and the nitrogen atom to which they are both attached together form a 3- to 8-membered heterocyclic ring having 0-1 additional heteroatom selected from N—$R^x$, O and S; wherein said ring is optionally substituted with one or more groups independently selected from (a) oxo, (b) $C_{1-4}$ alkyl optionally substituted with (i) $OR^a$, (ii) $NR^bR^c$, (iii) $NHC(O)R^a$, (iv) $NHCO_2R^a$, (v) halogen, (vi) $CO_2R^a$, (vii) $CONR^bR^c$, and (viii) heteroaryl, (c) $OR^a$, (d) heteroaryl optionally substituted with aryl, $C_{1-4}$ alkyl, (e) halogen, (f) aryl optionally substituted with halogen, $SO_2R^a$, (g) —$OCH_2C(O)NHR^b$, (h) $NR^bR^c$, (i) —$C(O)NR^bR^c$, (j) —$CO_2R^a$, or two substituents (including $R^x$) on adjacent ring atoms together with said atoms form a benzene, a $C_{3-8}$cycloalkyl, a 3- to 8-membered heterocycle, or a 5- or 6-membered heteroaryl, each optionally substituted with $R^x$; or two substituents on the same ring atom together with said atom form a $C_{3-8}$cycloalkyl or a 3- to 8-membered heterocycle, each optionally substituted with $R^x$; or
$R^{3a}$, $R^{3b}$ and the nitrogen atom to which they are both attached together form a 3- to 8-membered heteroaryl ring having 0-2 additional N, or 0-1 additional N and 0-1 heteroatom selected from O and S;
R⁴ is selected from the group consisting of (a) H, (b) halogen, (c) $C_{1-6}$ alkyl, (d) O—$C_{1-6}$ alkyl, (e) $C_{1-6}$ haloalkyl, (f) O—$C_{1-6}$ haloalkyl, (g) OH, (i) $NO_2$, (j) —$NR^bR^c$, (k) NHC(O)$R^a$, (l) NHC(O)$NHR^b$, (m) NHC(O)NHC(O)$NR^bR^c$, (n) $C_{2-6}$ alkenyl, (O)$C_{2-6}$ alkynyl, (p) $C_{3-6}$ cycloalkyl and (q) O-benzyl,
R⁵ is selected from the group consisting of H, halogen and $C_{1-3}$alkyl;
$R^a$ is selected from the group consisting of (a) H, (b) $C_{1-6}$ alkyl optionally substituted with one or more groups independently selected from (i) halogen, (ii) CN, (iii) OH, (iv) —$NR^bR^c$, (v) heterocyclyl optionally substituted with oxo, and (vi) $CO_2H$; and (c) benzyl;
$R^b$ and $R^c$ are independently selected from the group consisting of H, $C_{1-6}$ alkyl and $C_{3-6}$cycloalkyl; or
$R^b$, $R^c$ and the nitrogen atom to which they are attached together form a 5- or 6-membered heterocycle having 0 or 1 additional heteroatom selected from O, S and N—$R^x$, and optionally substituted with one or more groups independently selected from oxo,
$R^x$ is selected from (a) H, (b) —$C(O)C_{1-4}$ alkyl optionally substituted with OH or $OC_{1-4}$alkyl, (c) —$CO_2C_{1-4}$ alkyl, (d) —$CO_2C_{3-4}$ alkenyl, (e) C(O)-heteroaryl, (f) benzyl, (g) $C_{1-4}$ alkyl optionally substituted with OH, and (h) aryl optionally substituted with $CO_2H$.
In one group of formula (I) are compounds of formula (Ia):

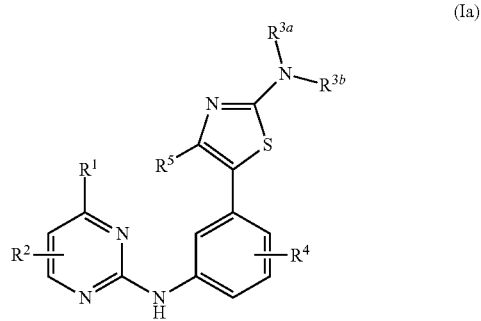

(Ia)

wherein the variables are as defined under formula (I).
In one subset of formula (Ia) are compounds wherein $R^{3a}$ and $R^{3b}$ are independently selected from (a) H, (b) $C_{1-6}$alkyl optionally substituted with one or two groups independently selected from (i) $OR^a$, (ii) phenyl optionally substituted with $OR^a$, $C_{1-3}$alkyl or $CF_3$, (iii) 5- or 6-membered heterocyclyl optionally substituted with one or two groups selected from oxo, $C_{1-3}$alkyl, $OR^a$ and $NR^bR^c$, (iv) 5- or 6-membered heteroaryl optionally substituted with one or two methyl groups, (v) $C_{3-6}$cycloalkyl, (vi) $CO_2H$, (vii) $NR^bR^c$, and (viii) $SR^a$, (c) $C_{1-6}$haloalkyl optionally substituted with OH, (d) $C_{3-6}$cycloalkyl optionally substituted with OH, and (e) phenyl optionally substituted with $CO_2H$ or $CO_2C_{1-4}$alkyl. In one aspect thereof, wherein $R^{3a}$ is H and $R^{3b}$ is selected from (a) $C_{1-6}$alkyl optionally substituted with one or two groups independently selected from (i) $OR^a$, (ii) phenyl optionally substituted with $OR^a$, $C_{1-3}$alkyl or $CF_3$, (iii) 5- or 6-membered heterocyclyl optionally substituted with one or two groups selected from oxo, $C_{1-3}$alkyl, $OR^a$ and $NR^bR^c$, (iv) 5- or 6-membered heteroaryl optionally substituted with one or two methyl groups, (v) $C_{3-6}$cycloalkyl, (vi) $CO_2H$, (vii) $NR^bR^c$, and (viii) $SR^a$, and (b) $C_{1-6}$haloalkyl optionally substituted with OH.
In another subset of formula (Ia) are compounds wherein $R^{3a}$, $R^{3b}$ and the nitrogen atom to which they are both attached together form a 5- or 6-membered heterocyclic ring having 0-1 additional heteroatom selected from N—$R^x$ and O, wherein said ring is optionally substituted with one or two groups independently selected from (a) oxo, (b) $C_{1-3}$alkyl optionally substituted with OH, $CO_2H$, $CONH_2$, $NHCOCH_3$, (c) $CF_3$, (d) OH, (e) $CONH_2$, (f) $CO_2H$, and (g) $NH_2$. In one aspect thereof $R^{3a}$, $R^{3b}$ and the nitrogen atom to which they are both attached together form a pyrrolidinyl or piperidinyl ring, each being optionally substituted as provided above.

In another group of formula (I) are compounds of formula (Ib):

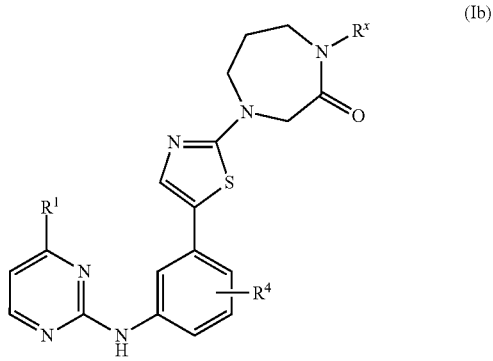

wherein the variables are as defined under formula (Ib). In one set of formula (Ib) are compounds wherein $R^x$ is H.

Within formulas (I), (Ia) and (Ib) are compounds wherein $R^1$ is trifluoromethyl.

Representative compounds of the present invention are as provided in the Examples section.

In the application various terms are as defined below, unless specified otherwise:

"Alkyl" refers to a straight- or branched-chain hydrocarbon radical having the specified number of carbon atoms. Examples of "alkyl" include, but are not limited to, methyl, ethyl, n-propyl, isopropyl, n-butyl, isobutyl, t-butyl, n-pentyl, isopentyl, and the like.

"Alkenyl" refers to a straight- or branched-chain hydrocarbon radical having at least one carbon-carbon double bond, and having the specified number of carbon atoms. Examples of "alkenyl" include, but are not limited to ethenyl, propenyl, n-butenyl, 3-methylbut-2-enyl and n-pentenyl.

"Alkynyl" refers to a straight- or branched-chain hydrocarbon radical having at least one carbon-carbon triple bond, and having the specified number of carbon atoms. Examples of "alkynyl" include, but are not limited to, ethynyl, propynyl, 2-butynyl and 3-methylbutynyl.

"Halogen" or "halo" refers to fluorine, chlorine, bromine, or iodine.

"Haloalkyl" refers to an alkyl group as defined above, substituted with at least one halo group, halo being as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo. Specific examples of haloalkyl include, but are not limited to, fluoromethyl, difluoromethyl, trifluoromethyl, 2-fluoroethyl, 2,2-difluoroethyl, and 2,2,2-trifluoroethyl.

"Cycloalkyl" refers to a saturated ring containing the specified number of ring carbon atoms, and no heteroatom. In a like manner the term "$C_{3-8}$ cycloalkyl" refers to a saturated ring having from 3 to 8 ring carbon atoms. Exemplary "cycloalkyl" groups useful in the present invention include, but are not limited to, cyclopropyl, cyclobutyl, cyclopentyl, cyclohexyl, cycloheptyl and cyclooctyl.

"Heterocyclic" or "heterocyclyl" refers to a non-aromatic saturated or partially unsaturated monocyclic ring in which one or two ring atoms are independently selected from N, S and O, and the ring being isolated or fused (including ortho-fused, spiro-fused and bridged) to another such heterocycle, a carbocycle, a benzene ring, or a heteroaryl ring. In the case of a bicyclic heterocycle, the attachment point may be on either ring. A carbon-linked heterocycle is attached via a ring carbon atom. Examples of heterocycle include, but are not limited to, aziridine, azetidine, pyrrolidine, piperidine, piperazine, morpholine, thiomorpholine, imidazolidine, oxazolidine, thiazolidine, azepane, diazepane, diazapene, oxetane, tetrahydrofuran, dihydropyran, pyran, tetrahydropyran, tetrahydrothiophen, tetrahydrothiopyran, 1,3-dioxane, 1,4-dioxane, 1,3-dioxolane, 8-azabicyclo[3.2.1]octane, 9-azabicyclo[3.3.1]nonane, 7-azabicyclo[22.1]heptane, 1,4-dioxaspiro[4.5]decane, "Heteroaryl" refers to aromatic monocyclic groups and fused bicyclic aromatic rings containing 1, 2, 3 or 4 heteroatoms selected from N, O and S. Examples of heteroaryl groups include, but are not limited to, furan, thiophene, pyrrole, imidazole, pyrazole, triazole, tetrazole, thiazole, isothiazole, oxazole, isoxazole, oxadiazole, thiadiazole, pyridine, pyridazine, pyrazine, pyrimidine, quinoline, isoquinoline, benzofuran, benzoxazole, benzothiazole, naphthyridine, benzothiopene, benzimidazole, indole and indazole.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

As used herein, the term "optionally" means that the subsequently described event(s) may or may not occur, and includes both event(s), which occur, and events that do not occur.

As used herein, the term "substituted with one or more groups" refers to substitution with the named substituent or substituents, multiple degrees of substitution, up to replacing all hydrogen atoms with the same or different substituents, being allowed unless the number of substituents is explicitly stated. Where the number of substituents is not explicitly stated, one or more is intended.

The term "Syk inhibitor" is used to mean a compound which inhibits the Syk enzyme.

The term "Syk mediated disease" or a "disorder or disease or condition mediated by inappropriate Syk activity" is used to mean any disease state mediated or modulated by Syk kinase mechanisms. Such disease states may include inflammatory, allergic and autoimmune diseases, for example, asthma, chronic obstructive pulmonary disease (COPD), adult respiratory distress syndrome (ARDs), ulcerative colitis, Crohns disease, bronchitis, dermatitis, allergic rhinitis, psoriasis, scleroderma, urticaria, rheumatoid arthritis, multiple sclerosis, cancer, HIV and lupus, in particular, asthma, chronic obstructive pulmonary disease (COPD), adult respiratory distress syndrome (ARDs), allergic rhinitis and rheumatoid arthritis.

As used herein, "a compound of the invention" means a compound of formula (I) or a salt, solvate or physiologically functional derivative thereof.

As used herein, the term "solvate" refers to a complex of variable stoichiometry formed by a solute (in this invention, a compound of formula (I), or a salt thereof) and a solvent. Such solvents for the purpose of the invention may not interfere with the biological activity of the solute. Examples of suitable solvents include, but are not limited to, water, acetone, methanol, ethanol and acetic acid. Preferably the solvent used is a pharmaceutically acceptable solvent. Examples of suitable pharmaceutically acceptable solvents include water, ethanol and acetic acid. Most preferably the solvent is water.

As used herein, the term "physiologically functional derivative" refers to a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The compounds of formula (I) may have the ability to crystallize in more than one form, a characteristic known as polymorphism, and it is understood that such polymorphic forms ("polymorphs") are within the scope of formula (I). Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention.

It is also noted that the compounds of Formula (I) may form tautomers. It is understood that all tautomers and mixtures of tautomers of the compounds of the present invention are included within the scope of the compounds of the present invention. Some of the compounds described herein contain olefinic double bonds, and unless specified otherwise, are meant to include both E and Z geometric isomers.

Whilst the embodiments for each variable have generally been listed above separately for each variable, this invention also includes those compounds in which several or each embodiment in formula (I) is selected from each of the embodiments listed above. Therefore, this invention is intended to include all combinations of embodiments for each variable.

The compounds of the present invention may be in the form of and/or may be administered as a pharmaceutically acceptable salt. For a review on suitable salts see Berge et al, J. Pharm. Sci. 1977, 66, 1-19. Typically, the salts of the present invention are pharmaceutically acceptable salts. Salts encompassed within the term "pharmaceutically acceptable salts" refer to non-toxic salts of the compounds of this invention. Suitable pharmaceutically acceptable salts can include acid or base additions salts.

A pharmaceutically acceptable acid addition salt can be formed by reaction of a compound of formula (I) with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated, for example, by crystallisation and filtration. A pharmaceutically acceptable acid addition salt of a compound of formula (I) can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

A pharmaceutically acceptable base salt can be formed by reaction of a compound of formula (I) with a suitable inorganic or organic base. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Other, non-pharmaceutically acceptable, salts, e.g. oxalates or trifluoroacetates, may also be used, for example, in the isolation of compounds of the invention, and are included within the scope of this invention.

The invention includes within its scope all possible stoichiometric and non-stoichiometric forms of the compounds of formula (I).

In the compounds of formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature.

Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates The compounds of formula (I) and salts, solvates and physiologically functional derivatives thereof are believed to be inhibitors of Syk activity, and thus be potentially useful in the treatment of diseases and conditions associated with inappropriate Syk activity.

Compound of formula (I) or its pharmaceutically acceptable salts and pharmaceutical compositions can be used to treat or prevent a variety of conditions or diseases mediated by Spleen tyrosine kinase (SYK). Such conditions and diseases include, but are not limited to: (1) arthritis, including rheumatoid arthritis, juvenile arthritis, psoriatic arthritis and osteoarthritis; (2) asthma and chronic obstruction pulmonary disease including emphysema; (3) autoimmune diseases or disorders, including those designated as single organ or single cell-type autoimmune disorders, those designated as involving systemic autoimmune disorder, for example systemic lupus erythematosis, immune thrombocytopenic purpura, rheumatoid arthritis, multiple sclerosis; (4) cancers or tumors, including solid tumors, and lymphoma and leukemia; (5) eye diseases including keratoconjunctivitis, vernal conjunctivitis, uveitis, keratitis, keratoconjunctivitis sicca (dry eye), allergic conjunctivitis; (6) intestinal inflammations, allergies or conditions including Crohn's disease and/or ulcerative colitis, inflammatory bowel disease; (7) skin diseases including atopic dermatitis, eczema, psoriasis, scleroderma, pruritus and other pruritic conditions; (8) allergic reactions including anaphylaxis, allergic rhinitis, allergic dermatitis, allergic urticaria, angioedema, allergic asthma, or allergic reaction to insect bites, food, drugs, or pollen; (9) transplant rejection.

The invention thus provides compounds of formula (I) and salts, solvates and physiologically functional derivatives thereof for use in therapy, and particularly in the treatment of diseases and conditions mediated by inappropriate Syk activity. The inappropriate Syk activity referred to herein is any Syk activity that deviates from the normal Syk activity expected in a particular mammalian subject. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk for the prevention and/or treatment of disorders related to unregulated Syk activity.

In a further embodiment, the present invention provides a method of treatment of a mammal suffering from a disorder mediated by Syk activity, which comprises administering to said mammal an effective amount of a compound of formula (I) or a pharmaceutically acceptable salt, solvate, or a physiologically functional derivative thereof.

In a further embodiment, the present invention provides for the use of a compound of formula (I), or a pharmaceutically acceptable salt or solvate thereof, or a physiologically functional derivative thereof, in the preparation of a medicament for the treatment of a disorder mediated by Syk activity.

In a further embodiment said disorder mediated by Syk activity is asthma. In a further embodiment said disorder is rheumatoid arthritis. In yet another embodiment, said disorder is cancer. In a further embodiment said disorder is ocular conjunctivitis.

While it is possible that, for use in therapy, a compound of formula (I), as well as salts, solvates and physiological functional derivatives thereof, may be administered as the raw chemical, it is possible to present the active ingredient as a pharmaceutical composition. Accordingly, the invention further provides a pharmaceutical composition, which comprises a compound of formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the formula (I), or salts, solvates and physiological functional derivatives thereof, with one or more pharmaceutically acceptable carriers, diluents or excipients.

Pharmaceutical compositions of the present invention may be presented in unit dose forms containing a predetermined amount of active ingredient per unit dose. Such a unit may contain, for example, 5 μg to 1 g, preferably 1 mg to 700 mg, more preferably 5 mg to 100 mg of a compound of the formula (I), depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), inhaled, nasal, ocular, or parenteral (including intravenous and intramuscular) route. Such compositions may be prepared by any method known in the art of pharmacy, for example by bringing into association the active ingredient with the carrier(s) or excipient(s).

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, COPD or ARDS.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Dosage forms for inhaled administration may conveniently be formulated as aerosols or dry powders.

For compositions suitable and/or adapted for inhaled administration, it is preferred that the compound or salt of formula (I) is in a particle-size-reduced form, and more preferably the size-reduced form is obtained or obtainable by micronisation. The preferable particle size of the size-reduced (e.g. micronised) compound or salt or solvate is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of formula (I) or salt or solvate thereof (preferably in particle-size-reduced form, e.g. in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of formula (I) or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (WAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering-Plough), Turbuhaler® (AstraZeneca), Ultrahaler® (Aventis), and the like.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurised aerosols, nebulizers or insufflators.

For pharmaceutical compositions suitable and/or adapted for intranasal administration, the compound of formula (I) or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity.

The following are examples of representative pharmaceutical dosage forms for the compounds of this invention:

| Injectable Suspension (I.M.) | mg/ml |
|---|---|
| Compound of Formula (I) | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula (I) | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula (I) | 25 |
| Lactose Powder | 573.5 |
| Magnesium Stearate | 1.5 |
| | 600 |

| Aerosol | Per canister |
|---|---|
| Compound of Formula (I) | 24 mg |
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian However, an effective amount of a compound of formula (I) for the treatment of diseases or conditions associated with inappropriate Syk activity, will generally be in the range of 5 µg to 100 mg/kg body weight of recipient (mammal) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of formula (I) per se.

Compounds of the present invention, and their salts and solvates, and physiologically functional derivatives thereof, may be employed alone or in combination with other therapeutic agents for the treatment of diseases and conditions associated with inappropriate Syk activity. Combination therapies according to the present invention thus comprise the administration of at least one compound of formula (I) or a pharmaceutically acceptable salt or solvate thereof, or a physiologically functional derivative thereof, and the use of at least one other pharmaceutically active agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of formula (I) may be combined with one or more other active agents such as: (1) TNF-α inhibitors; (2) non-selective COX-I/COX-2 inhibitors; (3) COX-2 inhibitors; (4) other agents for treatment of rheumatoid arthritis including methotrexate, leflunomide, sulfasalazine, azathioprine, cyclosporin, tacrolimus, penicilamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistaminic H1 receptor antagonists; (9) α1- and α2-adrenoceptor agonist; (10) anticholinergic agents; (11) β-adrenoceptor agonists; (12) insulin-like growth factor type I (IGF-1) mimetic; (13) glucocorticosteroids; (14) kinase inhibitors such as inhibitors of the Janus Kinases (JAK 1 and/or JAK2 and/or JAK 3 and/or TYK2), p38 MAPK and IKK2; (15) B-cell targeting biologics such as rituximab; (16) selective costimulation modulators such as abatacept; (17) interleukin inhibitors, such as IL-1 inhibitor anakinra and IL-6 inhibitor tocilizumab.

For the treatment of treatment cancer a compound of Formula (I) may be combined with one or more of an anticancer agents. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator; (2) other hormonal agents including aromatase inhibitors; (3) androgen receptor modulator; (4) retinoid receptor modulator; (5) antiproliferative agent; (6) prenyl-protein transferase inhibitor; (7) HMG-CoA reductase inhibitorn; (8) angiogenesis inhibitor; (9) PPAR-γ agonists, PPAR-δ agonists; (10) inhibitor of inherent multidrug resistance; (11) inhibitor of cell proliferation and survival signaling; (12) a bisphosphonate; (13) γ-secretase inhibitors, (14) agents that interfere with receptor tyrosine kinases (RTKs); (14) agent that interferes with a cell cycle checkpoint including inhibitors of ATR, ATM, the Chk1 and Chk2 kinases and cdk and cdc kinase inhibitors; (15) BTK inhibitors; (16) PARP; (17) mTOR inhibitors; and (18) cytotoxic/cytostatic agents classically used in cancer treatment such as the anthracyclines, platinum compounds, taxanes, podophyllotoxins, vinca alkaloids, nitrosoureas, bleomycin, mitomycin C, vorinostat, camptothecins and the like.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of Formula (I). Those skilled in the art will recognize if a stereocenter exists in compounds of Formula (I). Accordingly, the present invention includes all possible stereoisomers and includes not only mixtures of stereoisomers (such as racemic compounds) but the individual stereoisomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

The following abbreviations are used in the schemes and examples: Ac=Acetyl; AcOH=Acetic acid; Bn=benzyl; Boc (t-Boc)-t-butyloxycarbonyl; BOP=(Benzotriazol-1-yloxy)-tris(dimethylamino)phosphonium hexafluorophosphate; DAST=(Diethylamino)sulfur trifluoride; dba=dibenzylideneacetone; DCE=1,2-dichloroethane; DCM=Dichloromethane; Dibal/Dibal-H=Diisobutylaluminum hydride; DIPEA/DIEA=Diisopropylethylamine; DMAP=N,N-dimethyl-aminopyridine; DME=1,2-dimethoxyethane; DMF=Dimethyl formamide; DMSO=Dimethylsulfoxide; Dppf=1,1'-Bis (diphenylphosphino)ferrocene; EDC=N-(3-Dimethylaminopropyl)-N'-ethylcarbodiimide; EtOAc=Ethyl acetate; HATU=N,N,N',N'-Tetramethyl-O-(7-azabenzotriazol-1-yl) uronium hexafluorophosphate; HMDS=Hexamethyldisilazane; HOBT=1-Hydroxybenzotriazole; IPA=Isopropyl alcohol; LDA=Lithium diisopropylamide; mCPBa=Meta-chloroperoxy-benzoic acid; Ms=Methanesulfonyl (mesyl); MTBE=Methyl t-butyl ether; NBS=N-bromosuccinimide; Ph=phenyl; TBAF-t-butylammonium fluoride; TBDMS/TBS-t-butyl dimethylsilyl; TFA=Trifluoroacetic/trifluoroacetate;
THF=Tetrahydrofuran; TLC=Thin-layer chromatography; TMS=Trimethylsilyl; Ts=Toluenesulfonyl (tolyl); TSA=p-toluenesulfonic acid. Abbreviations for alkyl/cycloalkyl groups: Me=methyl, Et=ethyl, nPr=n-propyl, iPr=isopropyl, nBu=n-butyl, t-Bu=tertiary butyl, cPr=cyclopropyl, cBu=cyclobutyl, cPen=cyclopentyl, cHex=cyclohexyl, cHept=cycloheptyl.

Miyaura coupling. Compounds of formula (I) can also be obtained by reacting a 2-chloropyrimidine (3) and a thiazole-substituted aniline (4) in the presence of Pd catalyst. Thiaz-

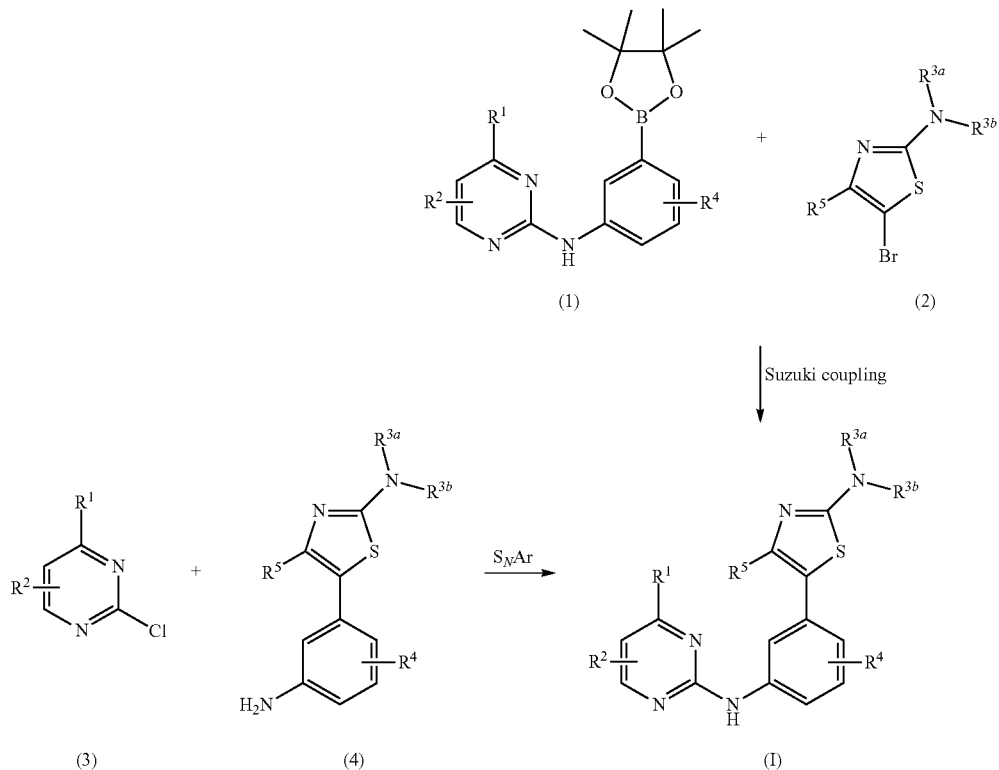

Compounds of formula (I) may be prepared by Suzuki coupling of the boronic ester (1) with a thiazole bromide (2). Boronic ester (1) can be obtained by reacting a 2-chloropyrimidine (3) and a 3-bromoaniline to form the corresponding N-(3-bromophenyl)-pyrimidine-2-amine, followed by Miyaura coupling.

ole-substituted anilines (4), in turn, may be formed under Suzuki coupling conditions using a bromothiazole and an aniline boronic ester, or a nitrophenyl boronic ester, followed by reduction of the nitro group to an amino group using standard conditions such as Pd-catalyzed hydrogenation.

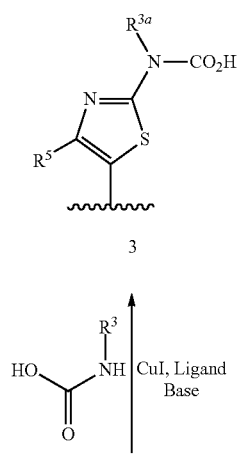

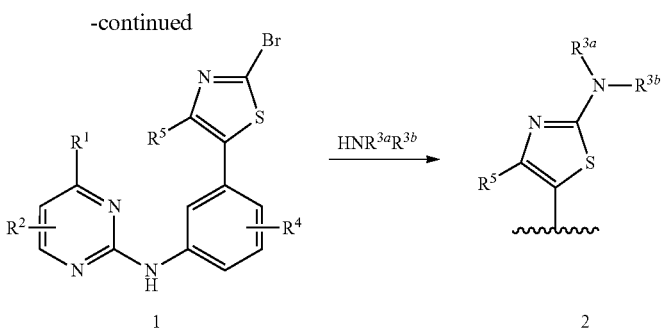
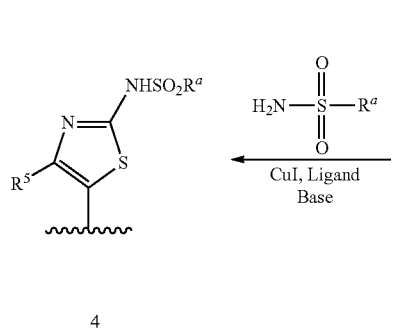
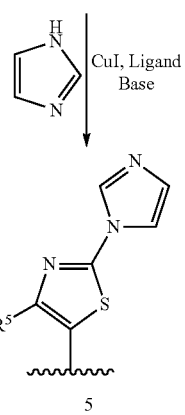

Compounds of formula (I) may also be prepared from compound (1) (e.g., Intermediates XI and XVIII described herein). S$_N$Ar displacement of affords compound (2). Copper catalyzed cross-coupling of bromothiazole (1) with amides, sulfonamides and imidazole provides compounds (3), (4) and (5), respectively.

SCHEME 3

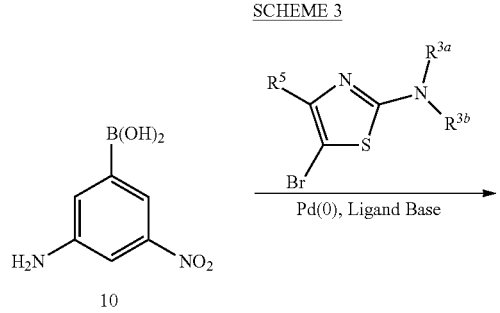

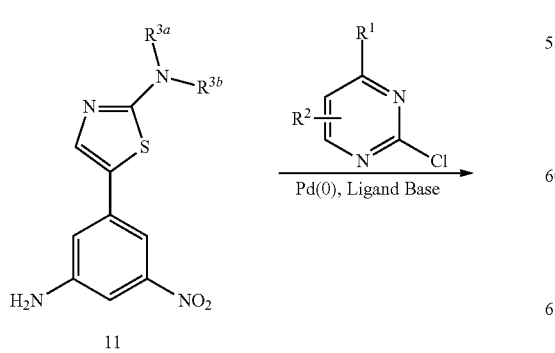

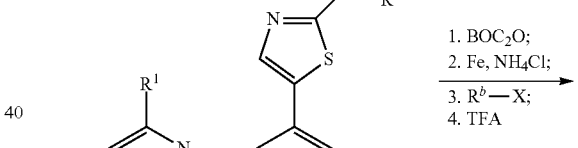
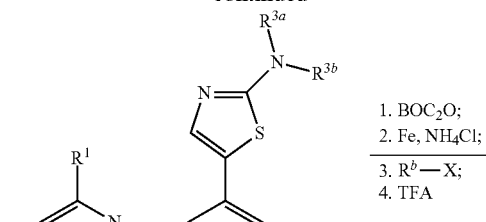
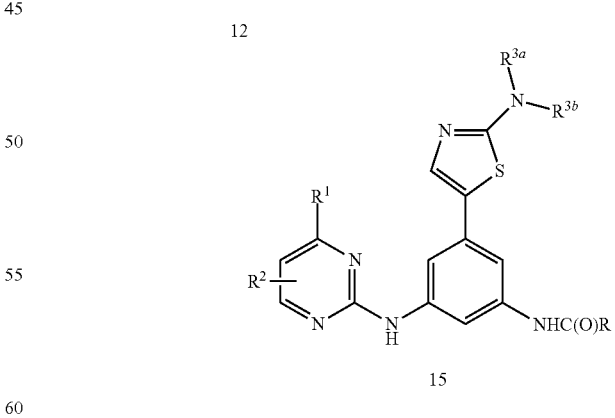

Palladium catalyzed cross coupling reaction of (3-amino-5-nitrophenyl)boronic acid (10) with heteroaryl bromides yields compound (11). Palladium catalyzed amination of compound (11) with a 2-chloropyrimidine results in the nitro compound (12). BOC protection and subsequent reduction of the nitro group provides the corresponding aniline 14. Treatment of 14 with acyl chlorides or isocyanates followed by deprotection provided compounds with the general structure of 15.

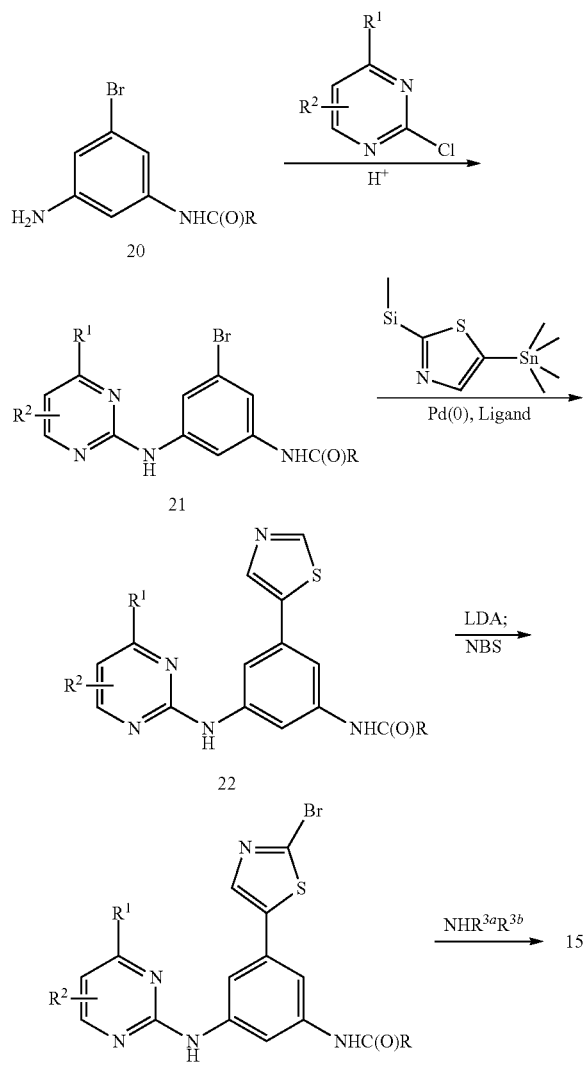

SCHEME 4

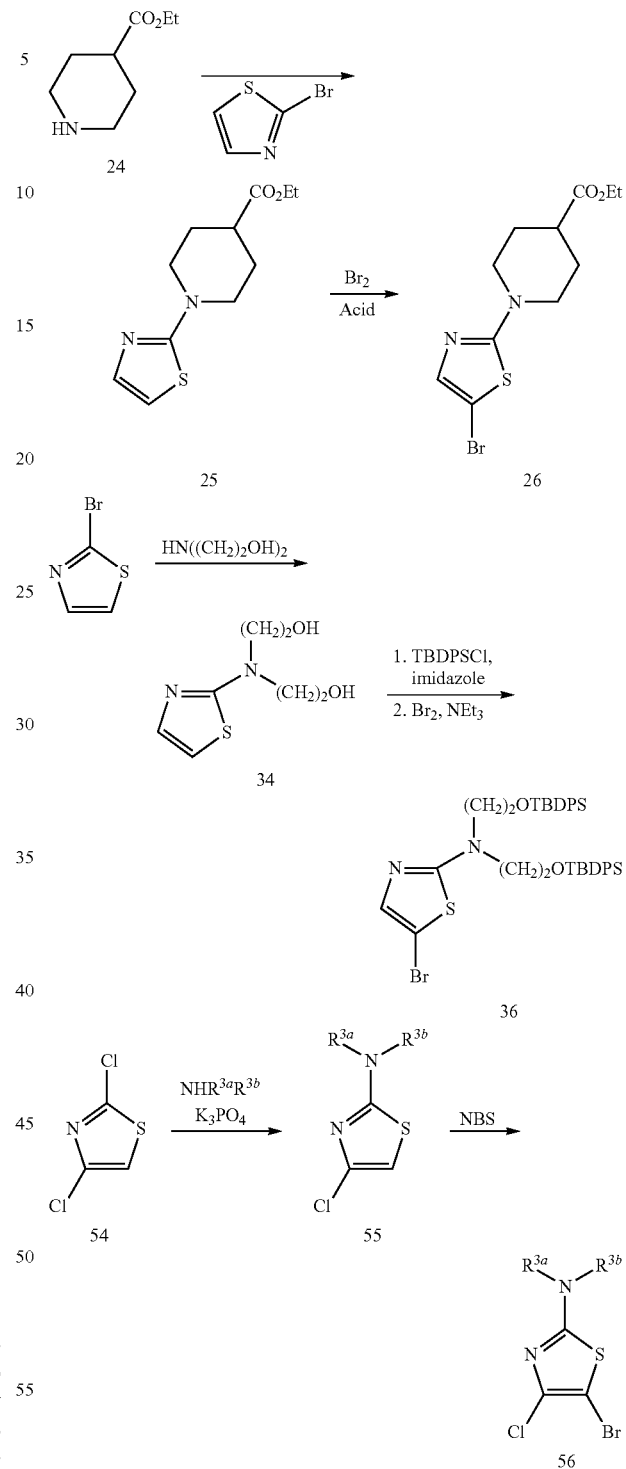

SCHEME 5

Compound (15) may also be prepared as depicted above. Bromoaniline (20) is prepared by bromination of commercially available 1,3-dinitrobenzene (16), which is reduced to provide 3-bromo-5-nitro-aniline. The aniline is subsequently capped via acylation or reaction with substituted isocyanates to yield corresponding amide/urea. An Fe-mediated reduction of nitro arene enables an $S_NAr$ reaction with a 2-chloropyrimidine to form compound (21). A palladium(0) catalyzed coupling of bromide (21) with known compound 2-(trimethylsilyl)-5-(trimethylstannanyl)-1,3-thiazole (for preparation, see: Dondoni, A.; Mastellari, A. R.; Medici, A.; Negrini, E.; Pedrini, P. *Synthesis* 1986, 9, 757-760) provides compound (22). Lithiation of thiazole (22) and exposure to NBS provides bromide (23). Displacement of the bromide by amines provides compound (15).

Examples of preparation of fuctionalized 5-bromo-1,3-thiazole are depicted in the above Scheme. $S_NAr$ of ethyl 4-piperidinecarboxylate (24) affords aminothiazole (25), which is brominated to give bromothiazole (26). 2-Bromo-1,3-thiazole is reacted with bis(2-hydroxyethyl)amine to provide adduct (34). Alcohol 34 is bis-silyl protected, then brominated to provide bromide (36). 2,4-Dichloro-1,3-thiazole

(54) undergoes nucleophilic substitution to provide the tertiary amine (55), which is brominated to provide (56).

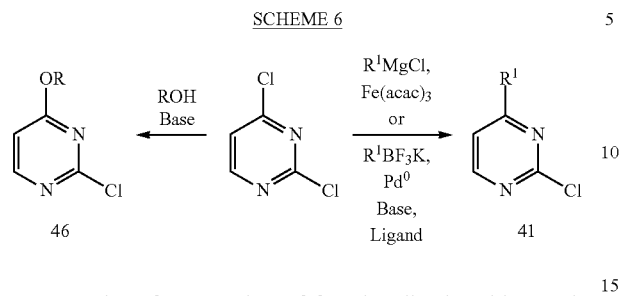

Examples of preparation of functionalized 2-chloropyrimidine are shown in the above Scheme. Starting from 2,4-dichloropyrimidine, iron catalyzed Grignard addition or a palladium catalyzed boronate coupling affords 4-substituted chloropyrimidine compound (41). Base mediated $S_NAr$ reaction with substituted alcohol nucleophiles provides chloropyrimidine compound (46).

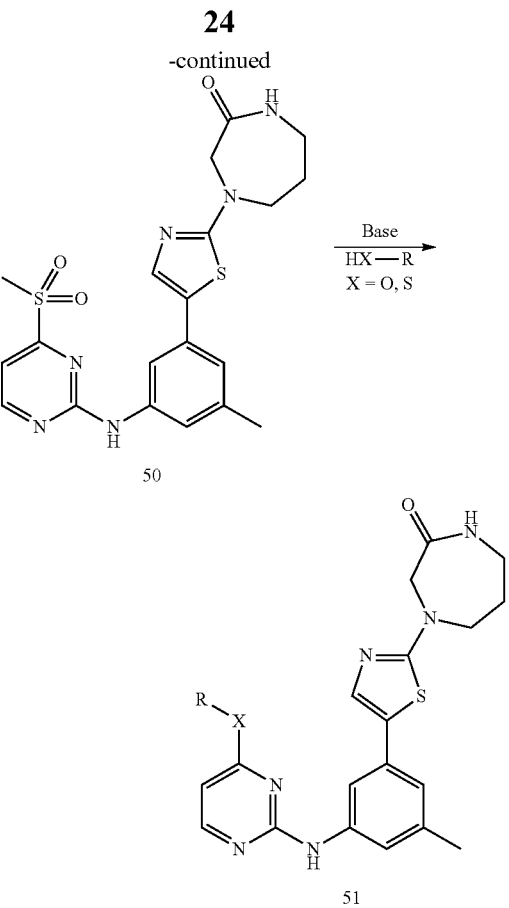

Additional manipulation of substitution at the 4-position of pyrimidine is illustrated in the above Scheme. Palladium catalyzed amination of Intermediate XX with 2-chloro-4-methylthiopyrimidine yields the coupled product (49). Oxidation of the thioether (49) with mCPBA results in sulfone (50). Base mediated $S_NAr$ of sulfone 50 with thiols or diols results in compounds with the general structure 51.

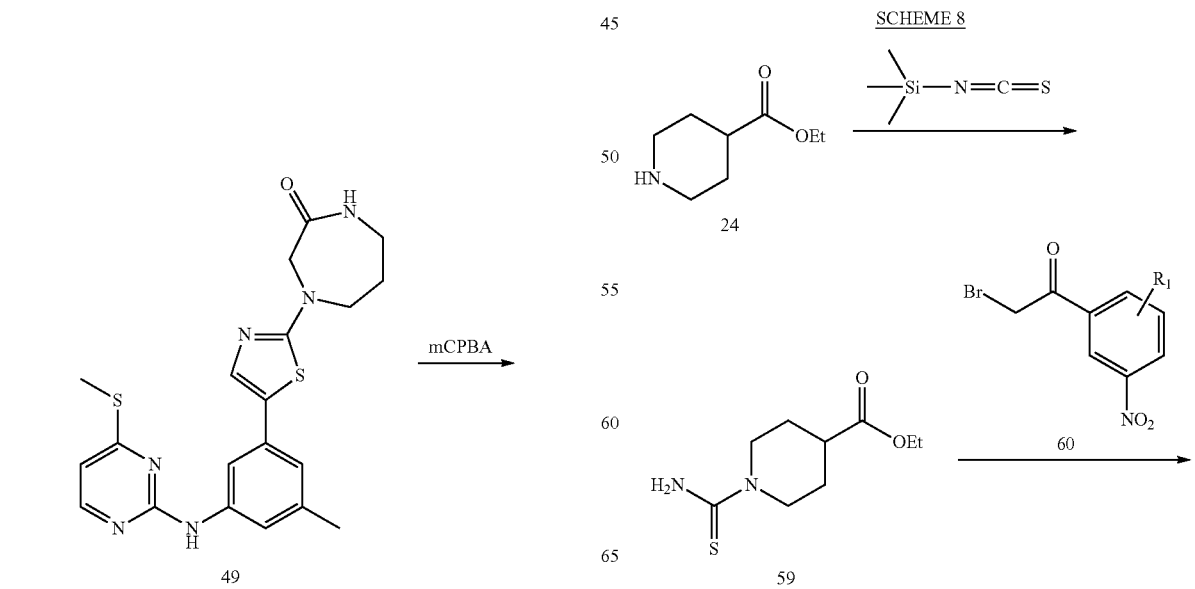

-continued

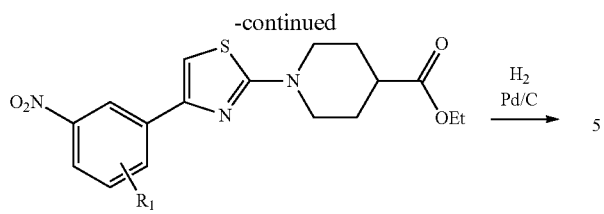

61

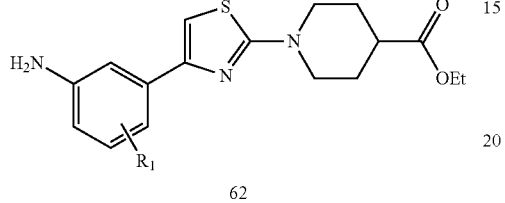

62

The amino ester (24) is transformed into the thiourea (59) with trimethylsilylisothiocyanate. Condensation with alpha-bromoketone (60) affords nitro-thiazole intermediate (61), which is reduced to the corresponding aniline by hydrogenation.

PREPARATION OF INTERMEDIATES

INTERMEDIATE III: N-(3-bromo-5-methylphenyl)-4-(trifluoromethyl)pyrimidin-2-amine

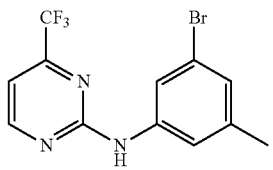 [SMILES: Cc1cc(Br)cc(Nc2nccc(C(F)(F)F)n2)c1]

A solution of 3-bromo-5-methylaniline (162.5 g, 873.66 mmol) in 1,4-dioxane (2 L) was prepared, and 2-chloro-4-(trifluoromethyl)pyrimidine (182 g, 994.54 mmol) and methanesulfonic acid (97.5 g, 1.02 mol) were added sequentially. The resulting solution was heated to reflux overnight. The resulting mixture was cooled and concentrated in vacuo. The residue was diluted with 2 L of water, then adjusted to pH 7-8 with aqueous sodium bicarbonate solution, followed by extraction with EtOAc (2×2 L) The organic layers were combined, washed with water (2×2 L), dried over anhydrous sodium sulfate and concentrated in vacuo. This resulted in N-(3-bromo-5-methylphenyl)-4-(trifluoromethyl)pyrimidin-2-amine (200 g, 602 mmol, 69%) as a light yellow solid. MS (ESI): [M+3]$^+$334.0. $^1$H NMR (400 MHz, CDCl$_3$): δ 8.68 (d, J=4.9 Hz, 1H); 7.79 (s, 1H); 7.30 (s, 2H); 7.10-7.06 (m, 2H); 2.36 (s, 3H).

INTERMEDIATE IV: N-[3-methyl-5-(4,4,5,5-tetramethyl-1,3,2-dioxaborolan-2-yl)phenyl]-4-(trifluoromethyl)pyrimidin-2-amine

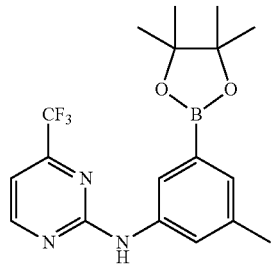 [SMILES: Cc1cc(Nc2nccc(C(F)(F)F)n2)cc(B2OC(C)(C)C(C)(C)O2)c1]

To a solution of Intermediate III (250 g, 753.01 mmol) in 1,4-dioxane (3 L) was added 4,4,5,5-tetramethyl-2-(4,4,5,5,5-tetramethyl-1,3,2-dioxaborolan-2-yl)-1,3,2-dioxaborolane (225 g, 885.83 mmol), KOAc (225 g, 2.30 mol) and Pd(dppf)Cl$_2$ (19 g, 25.23 mmol). The resulting solution was heated to reflux overnight. The solid was filtered. The filtrate was decolorized by passing through a silica gel column. The fractions were collected and concentrated in vacuo. This resulted in 110 g pure and 150 g crude product. The crude product was decolorized again with active carbon to get 125 g of pure product. This resulted in N-[3-methyl-5-(4,4,5,5-tetramethyl-1,3,2-dioxaborolan-2-yl)phenyl]-4-(trifluoromethyl)pyrimidin-2-amine (235 g, 620 mmol, 82%) as a white solid. MS APCI: [M+H]$^+$ m/z 380. $^1$H NMR (400 MHz, CDCl$_3$, ppm): 1.350 (12H, s), 2.386 (3H, s), 6.993-7.006 (1H, d, J=5.2 Hz), 7.385-7.427 (2H, s), 7.636 (1H, s), 7.753 (1H, s), 8.608-8.621 (1H, d, J=5.2 Hz).

INTERMEDIATE V: N-[3-methyl-5-(1,3-thiazol-5-yl)phenyl]-4-(trifluoromethyl)pyrimidin-2-amine

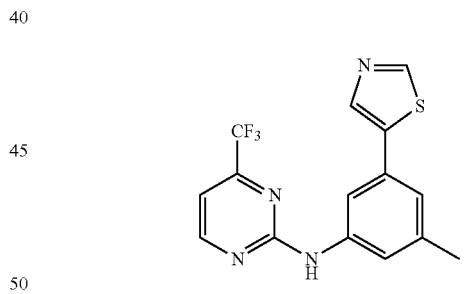

To a solution of Intermediate IV (80 g, 211.08 mmol) in 1,4-dioxane (800 mL) was added 5-bromo-1,3-thiazole (28 g, 171.78 mmol), Pd(dppf)Cl$_2$ (8 g, 10.62 mmol) and a solution of sodium carbonate (44.7 g, 421.70 mmol) in water (447 mL). The resulting solution was heated to reflux for 1 hour. Then it was allowed to cool and concentrated in vacuo. The residue was diluted with EtOAc (500 mL) and filtered. The filtrate was washed with brine (2×300 mL) and water (2×300 mL). The organic layer was dried over anhydrous sodium sulfate and concentrated in vacuo. The crude product was recrystallized from EtOAc:DCM in the ratio of 1:5 to get 34 g of product. The mother liquor was applied onto a silica gel column and eluted with dichloromethane/ethyl acetate (2:1). This resulted in N-[3-methyl-5-(1,3-thiazol-5-yl)phenyl]-4-(trifluoromethyl)pyrimidin-2-amine (42 g, 125 mmol, 73%) as a pale yellow solid. MS APCI: [M+H]$^+$ m/z 337. $^1$H NMR (400 MHz, CD$_3$COCD$_3$, ppm): 2.413 (3H, s), 7.250-7.263 (2H, m), 7.636 (1H, s), 8.204-8.213 (2H, m), 8.834-8.846 (1H, d, J=4.8 Hz), 8.970 (1H, s), 9.210 (1H, br).

INTERMEDIATE VI: N-(3-bromophenyl)-4-(trifluoromethyl)pyrimidin-2-amine

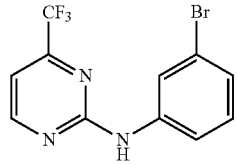 [SMILES: FC(F)(F)c1ccnc(Nc2cccc(Br)c2)n1]

Step 1:

A solution of 3-bromoaniline (250 g, 1.46 mol) in 1,4-dioxane (2.5 L) was prepared, and 2-chloro-4-(trifluoromethyl)pyrimidine (267 g, 1.47 mol) and methanesulfonic acid (155 g, 1.61 mol) were added sequentially. The resulting solution was heated to 100° C. overnight. The resulting mixture was cooled and concentrated in vacuo. The residue was adjusted to pH 7-8 with aqueous sodium bicarbonate solution. The solid was filtered, and the filtrate was extracted with EtOAc (4×500 mL) the organic layers were combined, washed with water (2×2 L), dried over anhydrous sodium sulfate and concentrated in vacuo. This resulted in N-(3-bromophenyl)-4-(trifluoromethyl)pyrimidin-2-amine (200 g, 629 mmol, 43%) as a light yellow solid. MS APCI: [M+3]$^+$ m/z 319. $^1$H NMR (500 MHz, CDCl$_3$): δ 8.68 (d, J=4.9 Hz, 1H); 7.95 (s, 1H); 7.53-7.50 (m, 1H); 7.44 (br s, 1H); 7.22 (m, 2H); 7.08 (d, J=4.9 Hz, 1H).

INTERMEDIATE VII: N-[3-(4,4,5,5-tetramethyl-1,3,2-dioxaborolan-2-yl)phenyl]-4-(trifluoromethyl)pyrimidin-2-amine

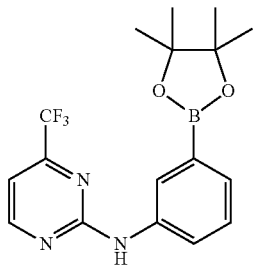 [SMILES: CC1(C)OB(c2cccc(Nc3nccc(C(F)(F)F)n3)c2)OC1(C)C]

Step 1: To a solution of Intermediate VI (200 g, 631 mmol) in 1,4-dioxane (2 L) was added 4,4,5,5-tetramethyl-2-(4,4,5,5-tetramethyl-1,3,2-dioxaborolan-2-yl)-1,3,2-dioxaborolane (177 g, 697 mmol), KOAc (187 g, 1.91 mol) and Pd(dppf)Cl$_2$ (24 g, 32 mmol). The resulting solution was heated to 100° C. for 2 h. The reaction was allowed to cool, and the solid was filtered. The filtrate was concentrated in vacuo. The residue was applied onto a silica gel column and eluted with ethyl acetate/petroleum ether (1:10). This resulted in N-[3-methyl-5-(4,4,5,5-tetramethyl-1,3,2-dioxaborolan-2-yl)phenyl]-4-(trifluoromethyl)pyrimidin-2-amine (140 g, 384 mmol, 61%) as a white solid. MS APCI: [M+H]$^+$ m/z 366. $^1$H NMR (400 MHz, DMSO-d6, ppm): 1.300 (12H, s), 7.237-7.249 (1H, m), 7.331-7.342 (2H, m), 7.882-7.910 (1H, m), 8.000 (1H, s), 8.796-8.806 (1H, m), 10.130 (1H, s).

INTERMEDIATE VIII: N-[3-(1,3-thiazol-5-yl)phenyl]-4-(trifluoromethyl)pyrimidin-2-amine

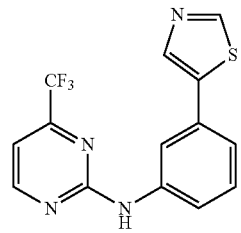 [SMILES: FC(F)(F)c1ccnc(Nc2cccc(-c3cncs3)c2)n1]

Pd(dppf)Cl$_2$ (1.01 g, 1.23 mmol) and Intermediate VII (9.0 g, 25 mmol) were combined in a flask and were evacuated and back-filled with nitrogen (×3). Added 2-Me THF (90 mL), 5-bromothiazole (4.45 g, 27.1 mmol), and aqueous sodium carbonate (24.7 mL, 49.3 mmol) sequentially. Sealed the flask and heated to 80° C. for 15 h. The brown solution was allowed to cool to rt, then diluted with water and EtOAc. The layers were separated, and the aqueous portion was extracted with EtOAc (2×). The combined organic portions were washed with saturated aqueous NaHCO$_3$, then Brine, then dried over Na$_2$SO$_4$ and concentrated in vacuo. Trituration with CH$_2$Cl$_2$ and collection of the beige solid via filtration provided 5.94 g of the desired product. The mother liquor was concentrated in vacuo and subsequent purification via silica gel column chromatography (CH$_2$Cl$_2$-40% EtOAc:CH$_2$Cl$_2$) provided an additional 1.41 g of the desired product. In total, N-[3-(1,3-thiazol-5-yl)phenyl]-4-(trifluoromethyl)pyrimidin-2-amine (7.35 g, 22.8 mmol, 93%) was isolated as a beige solid. MS APCI: [M+H]$^+$ m/z 323. $^1$H NMR (600 MHz, DMSO-d6, ppm) δ 10.32 (s, 1H), 9.06 (s, 1H), 8.82 (d, J=4.8 Hz, 1H), 8.20 (d, J=8.2 Hz, 1H), 8.20 (s, 1H), 7.64 (d, J=7.5 Hz, 1H), 7.40-7.31 (m, 2H), 7.27 (d, J=4.9 Hz, 1H).

INTERMEDIATE X: 4-(3-iodo-5-nitrophenyl)morpholine

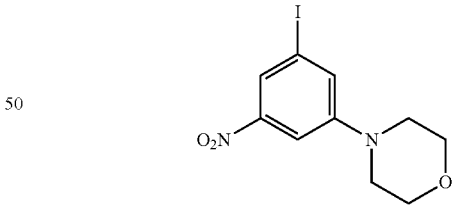

To a solution of 1-fluoro-3-iodo-5-nitrobenzene (4.0 g, 15 mmol) in DMSO (7.5 mL) was added morpholine (3.26 mL, 37.5 mmol), and the mixture (which instantly became purple) was heated to 130° C. for 30 min in the microwave. Purification was attempted by directly loading the mixture onto a CombiFlash column (80 g; load neat w/CH$_2$Cl$_2$ rinse; 100:0 to 60:40 hexanes:EtOAc over 35 minutes) but the mixture crashed at the top of the column and not all the mixture could be loaded. Nonetheless, after an inital spike in pressure, purification was possible, and the residual material was purified in a second purification (24 g; load w/CH$_2$Cl$_2$; 100:0 to 60:40 hexanes:EtOAc over 20 minutes). Concentration of the combined fractions from the two purifications provided 4-(3-iodo-5-nitrophenyl)morpholine (4.01 g, 12.0 mmol, 80%) as a bright yellow solid. $^1$H NMR (400 MHz, CDCl$_3$): δ 7.99 (s, 1H); 7.67 (s, 1H); 7.47 (s, 1H); 3.89 (s, 4H); 3.26 (s, 4H).

INTERMEDIATE XI: N-[3-(2-bromo-1,3-thiazol-5-yl)-5-methylphenyl]-4-(trifluoromethyl)-pyrimidin-2-amine

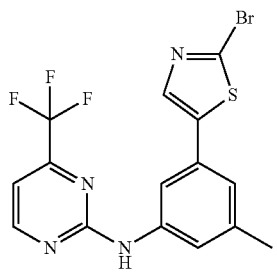 [SMILES: Cc1cc(Nc2nccc(C(F)(F)F)n2)cc(-c2cnc(Br)s2)c1]

Lithium diisopropylamide (11.4 mL, 20.5 mmol) was cooled to −70° C. Intermediate V (2.3 g, 6.8 mmol) in THF (23 mL) was added slowly over 15 minutes, keeping the temperature at −65° C. The reaction was allowed to stir for 30 minutes following the addition and then bromine (0.53 mL, 10.3 mmol) was added. The reaction was stirred for 30 minutes and then quenched with 20 mL of water and warmed to room temperature. The reaction was diluted with EtOAc (50 mL). The layers were separated and the organic portion was washed with Na$_2$SO$_3$ (10% aqueous), brine, dried over MgSO$_4$ and concentrated in vacuo. Purification via column chromatography (ISCO, dry load with silica gel, Hexane-50% EtOAc:Hexane) to provide N-[3-(2-bromo-1,3-thiazol-5-yl)-5-methylphenyl]-4-(trifluoromethyl)pyrimidin-2-amine (1.88 g, 4.53 mmol, 66%). MS APCI: [M+1, M+3]$^+$ m/z 414.8, 416.8. $^1$H NMR (600 MHz, cdcl3) δ 8.64 (d, J=4.9 Hz, 1H), 7.88 (s, 1H), 7.74 (s, 1H), 7.33 (s, 1H), 7.05 (t, J=6.4 Hz, 1H), 7.01 (s, 1H), 2.38 (s, 3H).

INTERMEDIATE XVIII: N-[3-(2-bromo-1,3-thiazol-5-yl)phenyl]-4-(trifluoromethyl)pyrimidin-2-amine

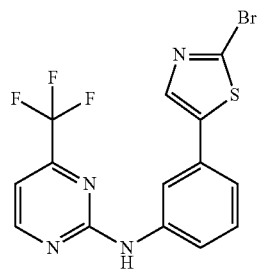

To a solution of N,N-diisopropylamine (0.164 mL, 1.153 mmol) in THF (2 mL) at 0° C., under nitrogen, was added n-butyllithium (0.439 mL, 1.098 mmol) dropwise (2 min.). The mixture was stirred at 0° C. for 15 min. and cooled to −78° C. A solution of N-[3-(1,3-thiazol-5-yl)phenyl]-4-(trifluoromethyl)pyrimidin-2-amine (Intermediate VIII, 118 mg, 0.366 mmol) in THF (1 mL) was then added and the resulting orange solution was stirred at the same temperature for 30 min. Bromine (0.021 mL, 0.403 mmol) was then added dropwise (2 min.). After 1 h, a ~60% conversion was observed. Bromine (0.019 mL, 0.366 mmol) was added, and the mixture was stirred for 30 min. at the same temperature and quenched by the addition of 25% aqueous NH$_4$OAc. The aqueous layer was extracted with EtOAc (3×). The combined organics were washed with brine, dried (Na$_2$SO$_4$) and concentrated in vacuo to give an amber gum (147 mg). Chromatography on silica gel using the CombiFlash R$_f$ System (5-25% EtOAc/hexane) afforded N-[3-(2-bromo-1,3-thiazol-5-yl)phenyl]-4-(trifluoromethyl)pyrimidin-2-amine (92 mg, 0.229 mmol, 63% yield) as a pale yellow gum. MS (+ESI): [M+1]$^+$=401. $^1$H NMR (400 MHz, Acetone-d6): δ 9.35 (s, 1H); 8.86 (d, J=4.9 Hz, 1H); 8.34 (s, 1H); 7.96 (s, 1H); 7.83 (d, J=8.3 Hz, 1H); 7.47 (t, J=7.9 Hz, 1H); 7.38 (d, J=7.8 Hz, 1H); 7.28 (d, J=4.9 Hz, 1H).

INTERMEDIATE XIX(1): 3-methyl-5-(4,4,5,5-tetramethyl-1,3,2-dioxaborolan-2-yl)aniline

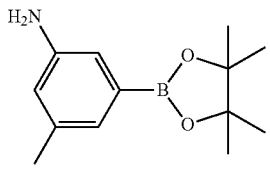 [SMILES: Cc1cc(N)cc(B2OC(C)(C)C(C)(C)O2)c1]

Dioxane (720 mL) in a 1 L three-necked round bottom flask was degassed for 30 min. 3-Bromo-5-methylaniline (60 g, 193 mmol), (bispinacolato)diboron (96 g, 377 mmol), potassium acetate (42.7 g, 435 mmol), X-Phos (8.3 g, 17.41 mmol) and Pd$_2$dba$_3$ (3.99 g, 4.35 mmol) were added to the degassed solvent under N$_2$ (g). After stirring for 10 min at room temperature, the system was heated to an internal temperature of 80° C. After ca. 4 hours, the heating mantle was removed and replaced with an ice water bath. The reaction mixture was cooled to 30° C., and was then filtered through a pad of celite (washing with 500 mL of MTBE). This was transferred to a 4 L separatory funnel containing 500 mL pH 8 phosphate buffer, 500 mL brine, and an additional 500 mL of MTBE. The layers were cut and the organic washed with 1 L of a 1:1 mixture of brine and water. The aqueous layers were combined and were sequentially back extracted with a second 500 mL portion of MTBE. The combined organics were treated with 100 g of MgSO$_4$ and the resulting mixture stirred for 20 min. This was then filtered and concentrated in vacuo. The resultant residue was purified by flash chromatography (Biotage, 0-25% ethyl acetate in hexanes) to yield 3-methyl-5-(4,4,5,5-tetramethyl-1,3,2-dioxaborolan-2-yl)aniline (66 g, 255 mmol, 88%) as a light orange solid. MS APCI: [M+H]$^+$ m/z 234.2.

INTERMEDIATE XX: 4-[5-(3-amino-5-methylphenyl)-1,3-thiazol-2-yl]-1,4-diazepan-2-one

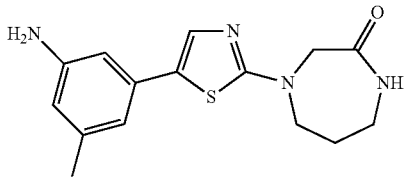 [SMILES: Cc1cc(N)cc(-c2cnc(N3CCCNC(=O)C3)s2)c1]

Step 1: Into a 5000-mL 4-necked round-bottom flask was placed a solution of 2-ethoxy-2-oxoethanaminium chloride (500 g, 3.58 mol) in water (2000 mL). To the mixture were added sodium bicarbonate (301 g, 3.58 mol) in several batches and acrylonitrile (228 g, 4.30 mol). The resulting solution was stirred overnight at 60-70° C. The reaction mixture was cooled and extracted with 3×2000 mL of ethyl acetate. The organic layers were combined, dried over anhydrous sodium sulfate and concentrated under vacuum. The crude product was purified by distillation under reduced pressure (10 mmHg) and the fraction was collected at 140-145° C. This resulted in 362.5 g (65%) of ethyl 2-(2-cyanoethylamino)acetate as a yellow oil.

Step 2:
Into 5000 ml 4-necked round-bottom flask was placed a solution of ethyl 2-(2-cyanoethylamino)acetate (1450 g, 9.29 mol) in chloroform (3300 mL), then added (Boc)₂O (2229 g, 10.22 mol). After stirred overnight at room temperature, the resulting mixture was concentrated under vacuum. This resulted in 2400 g (crude) of ethyl 2-(tert-butoxycarbonyl)acetate as a yellow oil.

Step 3: A mixture of ethyl 2-(tert-butoxycarbonyl)acetate (800 g, 3.12 mol), ethanol (6000 mL), Rany-Ni (400 g) and ammonia (500 mL) was stirred for 5 h at room temperature under a hydrogen atmosphere. The solid was filtered out. The filtrate was concentrated under vacuum. This resulted in 710 g (87%) of ethyl 2-(tert-butoxycarbonyl)acetate as yellowish brown oil.

Step 4: Into a 3000-mL 4-necked round-bottom flask was placed a solution of ethyl 2-(tert-butoxycarbonyl)acetate (910 g, 3.50 mol) in methanol (9100 mL), then added MeONa (189 g, 3.50 mol). The reaction mixture was heated to reflux for 1.5 hr, cooled to room temperature and concentrated under vacuum. The residue was diluted with 6000 mL of DCM, washed with brine, dried and concentrated under vacuum. The residue was purified by flash chromatography to afford 502.4 g (67%) of tert-butyl 3-oxo-1,4-diazepane-1-carboxylate as a yellow solid. ¹H NMR (400 MHz, CDCl₃) δ 1.50 (s, 9H), 1.92-1.94 (t, J=3.2 Hz, 2H), 3.29-3.33 (m, 2H), 3.62 (s, 2H), 4.06 (s, 2H), 5.75 (s, 1H).

Step 5: tert-Butyl 3-oxo-1,4-diazepane-1-carboxylate (141.0 g, 658 mmol) in DCM (349 mL) was treated with trifluoroacetic acid (279 mL, 3.6 mol) maintaining the temperature at 10° C. throughout the addition and the solution was stirred overnight. The solvent was removed and the residue was azeotroped with toluene/methanol (1:1). The oil was then stirred in isopropyl acetate (300 mL), which induced crystallation. A white solid was isolated and dried. The solid (195 g, 256 mmol) was dissolved in DMSO (155 mL) followed by 2,5-dibromothiazole (52 g, 213 mmol) and Hunigs base (83 mL, 926 mmol). The solution was vigourously stirred for 15-20 hours at 100° C. The mixture was treated with 0.75 L of brine. The precipitate was removed by filtration, washed with H₂O and dried under vacuum. The solution that remained was extracted with DCM (3×500 mL) and concentrated. The resulting oil was diluted with 400 mL of brine and extracted again with 2×250 mL DCM. Concentration afforded another 21 g of 4-(5-bromo-1,3-thiazol-2-yl)-1,4-diazepan-2-one and the total mass isolated was 46 g (54%). MS APCI: [M+H]⁺ m/z 278.0.

Step 6: 3-Methyl-5-(4,4,5,5-tetramethyl-1,3,2-dioxaborolan-2-yl)aniline (4 g, 17.16 mmol), 4-(5-bromo-1,3-thiazol-2-yl)-1,4-diazepan-2-one (4.74 g, 17.16 mmol), Pd₂(dba)₃ (0.786 g, 0.858 mmol), X-Phos (0.818 g, 1.716 mmol), and cesium carbonate (11.18 g, 34.3 mmol) were added to a dry flask. The flask was evacuated and backfilled with argon (3×) before adding fully degassed dioxane (55 mL) and water (5.50 mL). The flask was sealed and heated to 90° C. with stirring for 16 hours. The reaction was diluted with ethyl acetate and methanol and filtered through a celite plug, washing several times with ethyl acetate and methanol. The filtrate was dry loaded onto 12 g of silca gel and purified via silica gel chromatography (Biotage, 100% ethyl acetate, then 0-20% methanol in ethyl acetate) to afford 4-[5-(3-amino-5-methylphenyl)-1,3-thiazol-2-yl]-1,4-diazepan-2-one (2.33 g, 7.71 mmol, 45%). MS ESI: [M+H]m/z 303.1 ¹H NMR (500 MHz, DMSO-d₆) δ 7.59 (s, 1H), 7.37 (s, 1H), 6.46 (s, 1H), 6.44 (s, 1H), 6.24 (s, 1H), 5.07 (s, 2H), 4.15 (s, 2H), 3.78 (br s, 2H), 3.21 (br s, 2H), 2.14 (s, 3H), 1.78 (br s, 2H).

EXAMPLE 1

N-{3-[2-(2,8-diazaspiro[4.5]dec-8-yl)-1,3-thiazol-5-yl]-5-methylphenyl}-4-(trifluoromethyl)-pyrimidin-2-amine

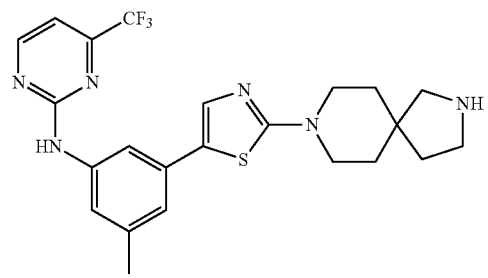 [SMILES: Cc1cc(Nc2nccc(C(F)(F)F)n2)cc(-c2cnc(N3CCC4(CCNC4)CC3)s2)c1]

Step 1: N-[3-(2-bromo-1,3-thiazol-5-yl)-5-methylphenyl]-4-(trifluoromethyl)pyrimidin-2-amine (47 mg, 0.113 mmol) was added to a 5 mL microwave vial along with tert-butyl 2,8-diazaspiro-[4.5]decane-2-carboxylate (81.6 mg, 0.340 mmol), DIEA (99 μl, 0.566 mmol), and n-butanol (600 μL). The vial was sealed and the mixture was allowed to react at 130° C. for 72 hours. The mixture was then cooled to room temperature and DMSO (2 mL) was added along with PS-benzaldehyde (623 mg, 0.679 mmol). The reaction mixture was allowed to stir overnight at room temperature, to scavenge excess amine. The mixture was filtered, washing with DMSO (1 mL) and concentrated under reduced pressure at 50° C. to afford tert-butyl 8-[5-(3-methyl-5-{[4-(trifluoromethyl)pyrimidin-2-yl]amino}phenyl)-1,3-thiazol-2-yl]-2,8-diazaspiro[4.5]decane-2-carboxylate, which was used in the following reaction without further purification.

Step 2: The residue from step 1 was dissolved in 2 mL of 1:1 TFA:DCM and was allowed to stir for 1 hour at room temperature. The reaction mixture was concentrated under reduced pressure at 40° C. The residue was dissolved in 1 mL of DMSO and purified by mass triggered reverse phase HPLC (5-95% acetonitrile in water, 0.1% formic acid) to afford N-{3-[2-(2,8-diazaspiro[4.5]dec-8-yl)-1,3-thiazol-5-yl]-5-methylphenyl}-4-(trifluoromethyl)pyrimidin-2-amine as the formate salt (27.5 mg, 51%). $^1$H NMR (600 MHz, DMSO) δ 10.16 (s, 1H), 8.79 (d, J=4.8 Hz, 1H), 7.82 (s, 1H), 7.46 (s, 1H), 7.29 (s, 1H), 7.24 (d, J=4.9 Hz, 1H), 6.96 (s, 1H), 3.51-3.39 (m, 4H), 3.16 (s, 2H), 2.95 (s, 2H), 2.25 (s, 3H), 1.77 (t, J=6.3 Hz, 2H), 1.62 (m, J=7.8 Hz, 12.4 Hz, 4H). APCI [M+H]$^+$ m/z 475.1. rhSYK activity=+++

The following examples were prepared in an analogous manner to that described in Example 1.

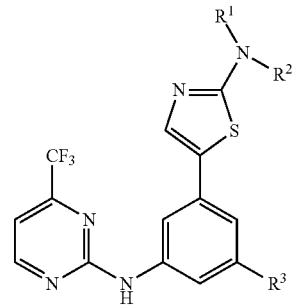

| Ex. | R$^1$ | R$^2$ | R$^3$ | rhSYK Activity | [M + H]+ Obs'd | Form(s) |
|---|---|---|---|---|---|---|
| 2 | H | —CH$_2$CH$_2$OH | H | +++ | 382.1 | Free Base |
| 3 | —CH$_2$CH$_2$—OH | —CH$_2$CH$_2$OH | H | +++, +++ | 426.1 | Free Base, Mesylate Salt |
| 4 | CH$_3$ | —CH$_2$CH$_2$OH | H | +++ | 396.1 | Free Base |
| 5 | H | —CH$_2$CH$_2$OCH$_3$ | H | +++ | 396.1 | Free Base |
| 6 | nBu | —CH$_2$CH$_2$OH | H | +++ | 438.3 | Free Base |
| 7 | CH$_3$ | —CH$_2$CH(Ph)OH | H | +++ | 472.1 | Free Base |
| 8 | —CH$_2$-2-pyridyl | —CH$_2$CH$_2$OH | H | +++ | 473.1 | Free Base |
| 9 | H | —CH$_2$CH(Et)OH | H | +++ | 410.0 | Free Base |
| 10 | H | —CH(Et)CH$_2$OH | H | +++ | 410.0 | Free Base |
| 11 | H | —CH(CH$_2$OH)$_2$ | H | +++ | 412.0 | Free Base |
| 12 | H | 3-OH-4-tetrahydrofuranyl (3R,4S) | H | +++ | 424.0 | Free Base |
| 13 | H | —CH$_2$CH(CHF$_2$)OH | H | +++ | 432.0 | Free Base |
| 14 | H | —CH(CH$_2$OH)-4-tetrahydropyranyl | H | +++ | 466.1 | Free Base |
| 15 | H | —(CH$_2$)$_3$OH | H | +++ | 396.1 | Free Base |
| 16 | H | —CH$_2$C(CH$_3$)$_2$CH$_2$OH | H | +++ | 424.2 | Free Base |
| 17 | H | —CH$_2$CH$_2$-(1-OH)—cPen | H | +++ | 450.2 | Free Base |
| 18 | H | —(CH$_2$)$_4$OH | H | +++ | 410.1 | Free Base |
| 19 | H | 4-OH—cHex (trans) | H | +++ | 436.1 | Free Base |
| 20 | H | —CH(iPr)CH$_2$OH | H | +++ | 424.1 | Free Base |
| 21 | H | CH$_3$ | H | +++ | 352.0 | Free Base* |
| 22 | H | —CH$_2$-(1-Me)-5-imidazolyl | H | +++ | 432.1 | Free Base |
| 23 | H | —C(CH$_3$)$_2$CH$_2$OH | H | +++ | 410.0 | Free Base |
| 24 | H | —CH$_2$CO$_2$H | H | +++ | 396.0 | Free Base |
| 25 | allyl | —CH$_2$C=CH$_2$ | H | +++ | 418.1 | Free Base |
| 26 | —CH$_2$Ph | —(CH$_2$)$_6$OH | H | ++ | 528.2 | Free Base |
| 27 | CH$_3$ | —(CH$_2$)$_2$OH | CH$_3$ | +++ | 410.0 | Free Base |
| 28 | H | —(CH$_2$)$_2$OH | CH$_3$ | +++ | 396.1 | Free Base |
| 29 | H | —CH$_2$C(CH$_3$)$_2$OH | H | +++ | 410.0 | Free Base |
| 30 | CH$_3$ | 4-(CO$_2$CH$_3$)Ph | H | ++ | 486.1 | Free Base |
| 31 | H | —CH$_2$-5-pyrimidinyl | H | +++ | 430.1 | Free Base |
| 32 | H | —CH(CH$_3$)CH$_2$OH | H | +++ | 396.1 | Free Base |
| 33 | CH$_3$ | —CH$_2$-2-pyridyl | H | +++ | 443.2 | Free Base |
| 34 | H | —(CH$_2$)$_2$OEt | H | +++ | 410.1 | Free Base |
| 35 | H | —(CH$_2$)$_2$-4-imidazolyl | H | +++ | 432.1 | Free Base |
| 36 | CH$_3$ | 3-tetrahydrofuranyl | H | +++ | 422.1 | Free Base |
| 37 | H | —CH$_2$-2-pyridyl | H | +++ | 429.1 | Free Base |
| 38 | H | —CH$_2$CHF$_2$ | H | +++ | 402.5 | Free Base |
| 39 | H | —CH$_2$-3-pyridyl | H | +++ | 429.1 | Free Base |
| 40 | H | —CH$_2$CH$_2$-2-thienyl | H | ++ | 448.1 | Free Base |
| 41 | H | —CH$_2$-1,2,3-triazol-4-yl | H | +++ | 419.1 | Free Base |
| 42 | H | —CH(Me)Et | H | +++ | 394.1 | Free Base |
| 43 | H | cPen | H | ++ | 406.2 | Free Base |
| 44 | H | —CH$_2$CH$_2$—SCH$_3$ | H | +++ | 412.1 | Free Base |
| 45 | H | —CH$_2$-3-tetrahydrofuranyl | H | +++ | 422.1 | Free Base |
| 46 | H | —CH$_2$CH$_2$-(4-OH)Ph | H | ++ | 458.1 | Free Base |
| 47 | H | —(CH$_2$)$_3$-(2-oxo)-1-pyrrolidinyl | H | +++ | 463.1 | Free Base |
| 48 | CH$_3$ | —CH$_2$Ph | H | ++ | 442.2 | Free Base |
| 49 | cPen | —CH$_2$CH$_2$OH | H | ++ | 450.2 | Free Base |

-continued

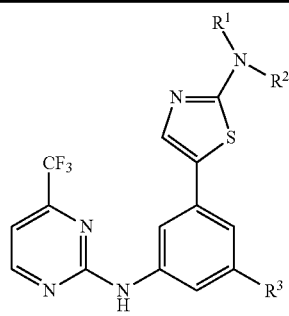

| Ex. | R¹ | R² | R³ | rhSYK Activity | [M + H]+ Obs'd | Form(s) |
|---|---|---|---|---|---|---|
| 50 | H | —CH₂CH(OH)CH₂OCH₃ | H | +++ | 426.2 | Free Base |
| 51 | H | —CH₂CH₂-(2-oxo)-1-pyrrolidinyl | H | +++ | 449.1 | Free Base |
| 52 | nPr | —CH₂CH₂OH | H | +++ | 424.2 | Free Base |
| 53 | H | —CH₂-(1-Me)-3-pyrrolidinyl | H | +++ | 435.2 | Free Base |
| 54 | H | —(CH₂)₂-(4-OMe)Ph | H | ++ | 472.1 | Free Base |
| 55 | H | —CH(Me)Ph | H | ++ | 442.2 | Free Base |
| 56 | H | —CH(CH₃)CH₂-2-pyrazinyl | H | +++ | 458.3 | Free Base |
| 57 | H | —CH₂-3-(1-piperidinyl)Ph | H | + | 511.3 | Free Base |
| 58 | H | 5-CH₂NH₂-2-Me-4-pyrimidinyl | H | +++ | 459.3 | Free Base |
| 59 | H | —CH₂-3-piperidinyl | H | +++ | 435.3 | Free Base |
| 60 | H | —CH₂CH₂-(2-CF₃)—Ph | H | + | 511.3 | Free Base |
| 61 | H | —CH₂-4-tetrahydropyranyl | H | +++ | 436.6 | Free Base |
| 62 | H | —CH₂-(1-Me)-4-pyrazolyl | H | +++ | 432.3 | Free Base |
| 63 | H | —CH₂CH₂-(3,5-diMe)-1-pyrazolyl | H | ++ | 460.3 | Free Base |
| 64 | H | —CH₂-(2-F-3-CF₃)—Ph | H | ++ | 514.5 | Free Base |
| 65 | H | (R) —CH(Me)—cHex | H | + | 448.6 | Free Base |
| 66 | H | (R) —CH₂-(1-Et)-2-pyrrolidinyl | H | +++ | 449.6 | Free Base |
| 67 | H | —CH₂-(1,5-diMe)-3-pyrazolyl | H | +++ | 446.6 | Free Base |
| 68 | H | (S) —CH₂-(1-Et)-2-pyrrolidinyl | H | ++ | 449.4 | Free Base |
| 69 | H | —CH₂-(1,3-diMe)-5-pyrazolyl | H | +++ | 446.3 | Free Base |
| 70 | H | —CH₂-(3-NMe₂)-3-tetrahydrothienyl | H | +++ | 481.3 | Free Base |
| 71 | H | (S) —CH₂-2-tetrahydrofuranyl | H | +++ | 422.6 | Free Base |
| 72 | H | —CH₂CH₂OCH₂CH₂OH | H | +++ | 426.5 | Free Base |
| 73 | H | (R) —CH(CH₂OH)CH₂OCH₂Ph | H | ++ | 502.4 | Free Base |
| 74 | H | (S) —CH(CH₂OH)—nBu | H | +++ | 438.5 | Free Base |
| 75 | H | —CH₂-(3-Me)-2-thienyl | H | + | 447.9 | Free Base |
| 76 | H | —CH₂-(3-(1-pyrazolyl))—Ph | H | +++ | 494.3 | Free Base |
| 77 | Et | —(CH₂)₃NH₂ | H | ++ | 437.4 | Free Base |
| 78 | H | —CH₂-(3-Ph)-4-pyrazolyl | H | ++ | 494.3 | Free Base |
| 79 | H | —CH₂-(1,3,5-triMe)-4-pyrazolyl | H | +++ | 460.3 | Free Base |
| 80 | H | CH(CH₂OH)CH₂CH₂SCH₃ | H | +++ | 456.3 | Free Base |
| 81 | H | —CH₂-(1-Me)-4-imidazolyl | H | +++ | 432.3 | Free Base |
| 82 | H | 3-OH—cHex | H | +++ | 436.3 | Free Base |
| 83 | H | —CH₂-(5-Me)-3-isoxazolyl | H | +++ | 433.3 | Free Base |
| 84 | H | —CH(Et)CH₂OH | CH₃ | +++, +++ | 424.0 | Formate Salt, TFA Salt |
| 85 | H | —CH₂-3-pyridyl | CH₃ | +++, +++ | 443.0 | Free Base, Formate Salt |
| 86 | H | —CH₂-4-pyridyl | CH₃ | +++ | 443.0 | Formate Salt |
| 87 | H | —CH₂-(1-Me)-5-imidazolyl | CH₃ | +++ | 446.1 | Formate Salt |
| 88 | H | —CH₂-(1,5-diMe)-3-pyrazolyl | CH₃ | +++ | 460.0 | Formate Salt |

-continued

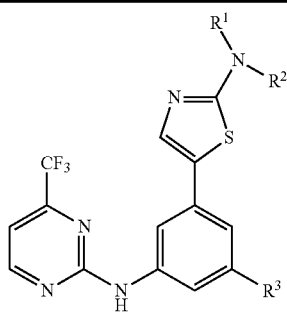

| Ex. | R¹ | R² | R³ | rhSYK Activity | [M + H]+ Obs'd | Form(s) |
|---|---|---|---|---|---|---|
| 89 | H | —CH₂-imidazo[1,2-a]pyridin-2-yl | CH₃ | ++ | 482.0 | Formate Salt |
| 90 | CH₃ | —CH₂CH₂-3-indolyl | CH₃ | ++ | 509.1 | Formate Salt |
| 91 | H | —CH₂-(4-CH₂CH₂CO₂CH₃)Ph | CH₃ | ++ | 528.1 | Formate Salt |
| 92 | H | —CH₂-(4-(4-morpholinylmethyl)-Ph | CH₃ | + | 271.1 *** | Formate Salt |
| 93 | H | —CH₂CH₂-4-imidazolyl | CH₃ | +++, +++ | 446.1 | Formate Salt, TFA Salt |
| 94 | H | —CH₂-(1-Me)-4-imidazolyl | CH₃ | +++ | 446.1 | Formate Salt |
| 95 | H | —CH₂CH(OH)CHF₂ | CH₃ | +++ | 446.0 | Formate Salt |
| 96 | H | —CH₂CH₂-2-pyrazinyl | CH₃ | +++ | 458.0 | Formate Salt |
| 97 | H | —CH₂-(5-Me)-3-isoxazolyl | CH₃ | +++ | 447.0 | Formate Salt |
| 98 | H | (cis) —CH₂-(4-NH₂)—cHex | CH₃ | +++, +++ | 463.1 | Formate Salt, TFA Salt |
| 99 | H | —CH(CH₃)-3-pyridyl | CH₃ | +++ | 457.1 | Formate Salt |
| 100 | H | —CH₂-(1-Me)-4-pyrazolyl | CH₃ | +++ | 446.0 | Formate Salt |
| 101 | CH₃ | —CH₂-(1-Me)-4-pyrazolyl | CH₃ | +++ | 460.1 | Formate Salt |
| 102 | CH₃ | —CH₂-2-benzoxazolyl | CH₃ | ++ | 497.0 | Formate Salt |
| 103 | H | —CH₂-(1-Me)-1,2,4-triazol-5-yl | CH₃ | +++ | 447.1 | Formate Salt |
| 104 | H | —CH₂-4-isothiazolyl | CH₃ | +++ | 449.0 | Formate Salt |
| 105 | H | —CH₂-1,2,5-thiadiazol-3-yl | CH₃ | +++ | 450.0 | Formate Salt |
| 106 | H | —CH₂CH₂-1,2,4-triazol-5-yl | CH₃ | +++ | 447.1 | Formate Salt |
| 107 | H | —CH₂CH₂-2-furanyl | CH₃ | +++ | 446.1 | Formate Salt |
| 108 | H | —CH₂CH₂-2-thienyl | CH₃ | ++ | 462.0 | Formate Salt |
| 109 | H | —CH₂CH₂-2-thiazolyl | CH₃ | +++ | 463.0 | Formate Salt |
| 110 | H | —CH₂CH₂-4-thiazolyl | CH₃ | +++ | 463.0 | Formate Salt |
| 111 | H | —CH₂CH₂-(3,5-diMe)-4-pyrazolyl | CH₃ | +++ | 474.1 | Formate Salt |
| 112 | H | —CH₂CH₂-3-indolyl | CH₃ | +++ | 495.1 | Formate Salt |
| 113 | H | —CH₂-(1-Me)-3-piperidinyl | CH₃ | +++ | 463.2 | Formate Salt |
| 114 | H | —(CH₂)₃-(3-oxo-2,4-dihydro)-4-pyrazolyl | CH₃ | +++ | 476.1 | Formate Salt |
| 115 | H | —CH₂CH₂-4-piperidinyl | CH₃ | +++ | 464.1 | Formate Salt |

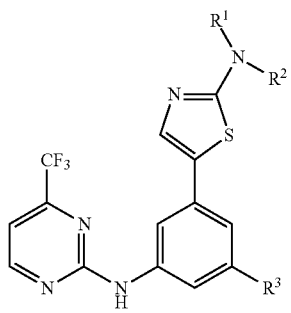

| Ex. | R¹ | R² | R³ | rhSYK Activity | [M + H]+ Obs'd | Form(s) |
|---|---|---|---|---|---|---|
| 116 | H | —CH$_2$CH$_2$-(1-Me-4-OH)-4-piperidinyl | CH$_3$ | +++ | 493.1 | Free Base |
| 117 | H | —CH$_2$CH(OH)-4-pyridyl | CH$_3$ | ++ | 473.1 | Free Base |
| 118 | H | —CH$_2$CH$_2$-4-pyridyl | CH$_3$ | +++ | 457.1 | Free Base |

*HCl salt of the amine was used
**APCI [M + 2H]⁺ m/z observed
***APCI [M/2 + H]⁺ m/z observed

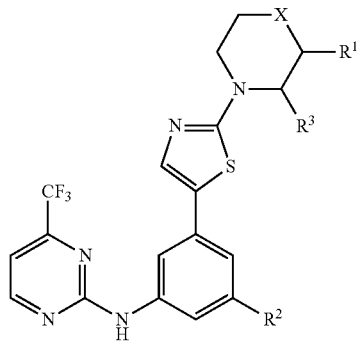

| Ex. | X | R¹ | R² | R³ | rhSYK Activity | [M + H]+ Obs'd | Form(s) |
|---|---|---|---|---|---|---|---|
| 119 | O | H | H | H | +++ | 408.1 | Free Base |
| 120 | O | CH$_2$CH$_2$OH | H | H | +++ | 452.3 | Free Base |
| 121 | O | CF$_3$ | H | H | ++ | 476.1 | Free Base |
| 122 | O | H | CH$_3$ | H | +++ | 422.0 | Formate Salt |
| 123 | NH | =O | H | H | + | 421.1 | Free Base |
| 124 | NH | =O | H | CH$_3$ | +++ | 435.1 | Free Base |
| 125 | N-(3-CO$_2$H)Ph | H | H | H | +++ | 527.1 | Free Base |
| 126 | N—CO$_2$CH$_2$—CH=CH$_2$ | H | H | CH$_2$OH | ++ | 521.1 | Free Base |
| 127 | N—C(O)CH$_2$OCH$_3$ | H | H | H | +++ | 479.1 | Free Base |
| 128 | N—C(O)-6-indolyl | H | CH$_3$ | H | +++ | 564.1 | Formate Salt |

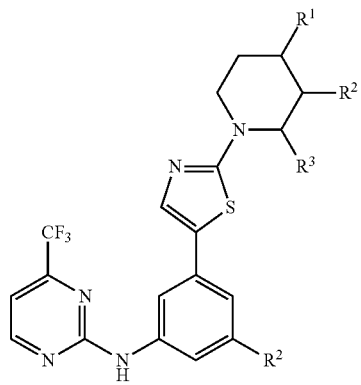

| Ex. | R¹ | R² | R³ | R⁴ | rhSYK Activity | [M + H]+ Obs'd | Form(s) |
|---|---|---|---|---|---|---|---|
| 129 | OH | H | H | H | +++ | 422.1 | Free Base |
| 130 | —CH₂OH | H | H | H | +++ | 436.1 | Free Base |
| 131 | H | OH | H | H | +++ | 422.1 | Free Base |
| 132 | H | H | CH₂OH | H | +++ | 436.3 | Free Base |
| 133 | Ph | OH | H | H | ++ | 498.3 | Free Base |
| 134 | H | —CH₂OH | H | H | +++ | 436.3 | Free Base |
| 135 | H | C(CH₃)₂OH | H | H | +++ | 464.3 | Free Base |
| 136 | —OCH₂C(O)NH—cPr | H | H | H | ++ | 519.1 | Free Base |
| 137 | 4-Ph-1,2,3-triazol-1-yl | H | H | H | ++ | 549.1 | Free Base |
| 138 | —CH₂NHCO₂—tBu | H | H | H | + | 535.2 | Free Base |
| 139 | H | OH | CH₂OH | H | +++ | 452.1 | Free Base |
| 140 | F | H | H | H | ++ | 424.2 | Free Base |
| 141 | —CH₂CH₂OH | H | H | H | +++ | 450.2 | Free Base |
| 142 | H | CH₂CH₂OH | H | H | +++ | 450.2 | Free Base |
| 143 | NH₂ | H | H | H | +++ | 421.2 | Free Base |
| 144 | H | CF₃ | H | H | ++ | 474.1 | Free Base |
| 145 | OCH₂C(O)NH—tBu | H | H | CH₃ | + | 549.1 | Formate Salt |
| 146 | 4-(SO₂Me)Ph | H | H | CH₃ | + | 574.1 | Formate Salt |
| 147 | H | 3-Me-1,2,4-oxadiazol-5-yl | H | CH₃ | ++ | 502.1 | Formate Salt |
| 148 | —CH₂CONH₂ | H | H | CH₃ | +++ | 477.1 | Formate Salt |
| 149 | H | —CH₂-1-imidazolyl | H | CH₃ | +++ | 250.6*** | Formate Salt |
| 150 | CH₂CH₂NHC(O)CH₃ | H | H | CH₃ | +++ | 505.1 | Formate Salt |
| 151 | R¹ + R² complete a benzene ring | | CH₂CO₂H | H | +++ | 512.2 | Free Base |
| 152 | R¹ + R² complete a benzene ring | | H | H | ++ | 454.2 | Free Base |
| 153 | R¹ + R² form —CH₂N(CH3)CH₂— | | H | CH₃ | +++ | 475.1 | Formate Salt |

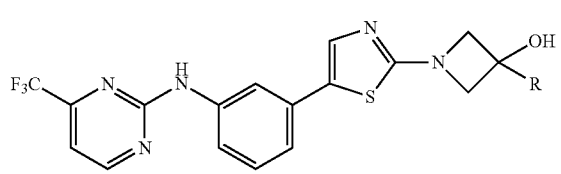

| Example | R | rhSYK Activity | [M + H]+ Obs'd | Form(s) |
|---|---|---|---|---|
| 154 | CH₃ | +++ | 408.1 | Free Base* |
| 155 | CF₃ | ++ | 462.1 | Free Base* |

*HCl salt of the amine was used

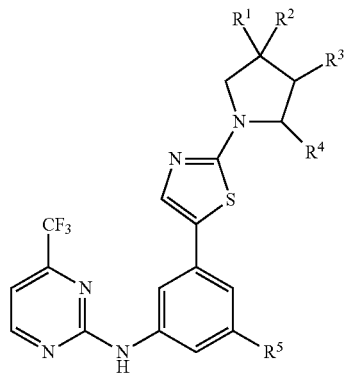

| Ex | R¹ | R² | R³ | R⁴ | R⁵ | rhSYK Activity | [M + H]+ Obs'd | Form(s) |
|---|---|---|---|---|---|---|---|---|
| 156 | R¹ + R³ form a bond | H | — | H | H | +++ | 390.1 | Free Base |
| 157 | OH (cis) | H | OH | H | H | +++ | 424.1 | Free Base |
| 158 | OH | H | H | H | H | +++ | 408.1 | Free Base |
| 159 | OH | Ph | H | H | H | ++ | 484.1 | Free Base |
| 160 | 4-Cl—Ph | (CH₂)₂OH | H | H | H | + | 546.1 | Free Base |
| 161 | H | H | H | Ph | H | ++ | 468.2 | Free Base |
| 162 | NH₂ | H | H | H | H | +++ | 407.2 | Free Base |
| 163 | NH₂ (S) | H | H | H | H | +++ | 407.3 | Free Base |
| 164 | R¹+ R² form —OCH₂CH₂O— | | H | H | CH3 | +++ | 463.2 | Formate Salt |
| 165 | R₁ + R₃ form —CH(CH₂OH)NHCH2— | | — | H | CH₃ | +++ | 477.1 | Formate Salt |

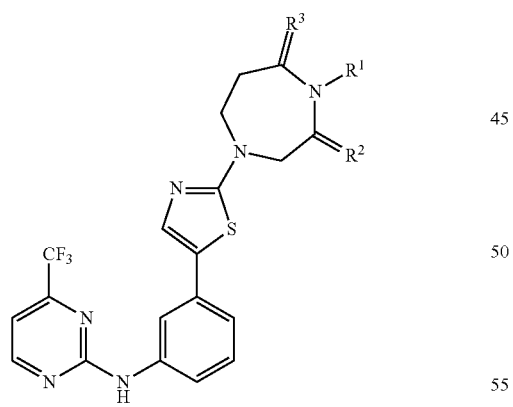

| Ex. | R¹ | R² | R³ | rhSYK Activity | [M + H]+ Obs'd | Form(s) |
|---|---|---|---|---|---|---|
| 166 | H | O | H,H | +++ | 435.1 | Free Base |
| 167 | H | H,H | H,H | +++ | 421.1 | Free Base |
| 168 | H | H,H | O | +++ | 435.1 | Free Base |
| 169 | —C(O)CH3 | H,H | H,H | +++ | 463.1 | Free Base |
| 170 | CH3 | H,H | O | +++ | 449.1 | Free Base |

| Ex. | R¹ | R² | rhSYK Activity | [M + H]+ Obs'd | Form(s) |
|---|---|---|---|---|---|
| 171 | H | (N-bicyclic group with CH₂OH) | +++ | 434.1 | Free Base |
| 172 | CH₃ | (hexahydropyrrolo-pyrazine) | +++ | 461.1 | Formate Salt |
| 173 | CH₃ | (imidazo-pyrazine) | +++ | 457.7 | Free Base |
| 174 | CH₃ | (imidazo-pyrazine isomer) | +++ | 457.7 | Free Base |

EXAMPLE 175

3-[5-(3-{[4-(trifluoromethyl)pyrimidin-2-yl]amino}phenyl)-1,3-thiazol-2-yl]-1,3-oxazolidin-2-one

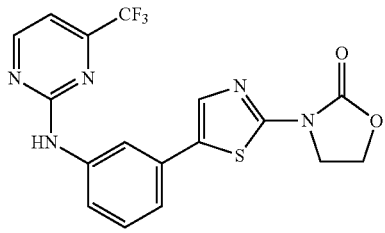 [SMILES: O=C1OCCN1c1ncc(-c2cccc(Nc3nccc(C(F)(F)F)n3)c2)s1]

To N-[3-(2-bromo-1,3-thiazol-5-yl)phenyl]-4-(trifluoromethyl)pyrimidin-2-amine (180 mg, 0.449 mmol) were added copper iodide (17.09 mg, 0.090 mmol), K₂CO₃ (124 mg, 0.897 mmol), 1,3-oxazolidin-2-one (78 mg, 0.897 mmol) and dioxane. N,N-dimethylethane-1,2-diamine (7.91 mg, 0.090 mmol) was added and the reaction was allowed to stir at 110° C. for 4 hours. The reaction mixture was diluted with ethyl acetate washed with brine, dried over Na₂SO₄ and concentrated in vacuo. The product was purified by column chromatography on silica gel (50-70% ethyl acetate/hexane) to afford 3-[5-(3-{[4-(trifluoromethyl)pyrimidin-2-yl]amino}phenyl)-1,3-thiazol-2-yl]-1,3-oxazolidin-2-one (98 mg, 54%) as an off-white solid. APCI [M+H]⁺ m/z 408.0. ¹H NMR (500 MHz, CDCl₃): δ 8.71 (d, J=4.9 Hz, 1H); 8.08 (s, 1H); 7.69 (s, 1H); 7.51 (d, J=8.1 Hz, 1H); 7.43-7.38 (m, 2H); 7.30 (s, 1H); 7.11 (d, J=4.9 Hz, 1H); 4.68 (t, J=8.1 Hz, 2H); 4.39 (t, J=8.1 Hz, 2H). rhSYK activity=+++.

The following examples were prepared in an analogous manner of that described in Example 175.

| Example | R¹ | R² | rhSYK Activity | [M + H]+ Observed | Form(s) |
|---|---|---|---|---|---|
| 177 | H | —NHSO₂CH₃ | +++ | 416.1 | Free Base |
| 178 | H | 1-imidazolyl | +++ | 389.1 | Free Base |
| 179 | H | 2-oxo-1-imidazolidinyl | +++ | 407.1 | Free Base |
| 180 | CH₃ | 2-oxo-3-oxazolidinyl | +++ | 422.0 | Free Base |

EXAMPLE 181

N-[3-(2-amino-1,3-thiazol-5-yl)phenyl]-4-(trifluoromethyl)pyrimidin-2-amine

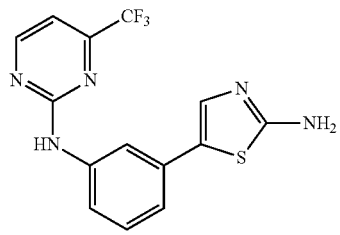 [SMILES: Nc1ncc(-c2cccc(Nc3nccc(C(F)(F)F)n3)c2)s1]

Step 1: A sealable reaction tube was charged with, palladium (II) acetate (6.15 mg, 0.027 mmol), butyldi-1-adamantylphosphine (19.64 mg, 0.055 mmol) and THF (4 mL) and was stirred for 10 minutes under nitrogen. N-[3-(4,4,5,5-tetramethyl-1,3,2-dioxaborolan-2-yl)phenyl]-4-(trifluoromethyl)pyrimidin-2-amine (200 mg, 0.548 mmol) (Intermediate VII), tert-butyl (5-bromo-1,3-thiazol-2-yl)carbamate (199 mg, 0.712 mmol), potassium fluoride (95 mg, 1.643 mmol) and Water (1.333 mL) were then successively added. The tube was capped and the mixture was stirred at 75° C. for 17 hours, cooled to room temperature and quenched by the addition of 25% aqueous NH$_4$OAc. The aqueous layer was extracted twice with ethyl acetate. The combined organic fractions were washed with water and brine, dried over Na$_2$SO$_4$ and concentrated. The product was purified by column chromatography on silica gel (ethyl acetate/hexane) to afford tert-butyl[5-(3-{[4-(trifluoromethyl)pyrimidin-2-yl]amino}phenyl)-1,3-thiazol-2-yl]carbamate (65.1 mg, 27.2%) as a beige solid. APCI [M+H]$^+$ m/z 382

Step 2:

To a suspension of tert-butyl[5-(3-{[4-(trifluoromethyl)pyrimidin-2-yl]amino}phenyl)-1,3-thiazol-2-yl]carbamate (56 mg, 0.128 mmol) in CH$_2$Cl$_2$ (2 mL) at room temperature, under nitrogen, was added trifluoroacetic acid (0.197 mL, 2.56 mmol). The mixture was stirred at room temperature for 17 hours and concentrated to dryness. The residue was partitioned between ethyl acetate and 5% NaHCO$_3$. The aqueous layer was extracted twice with ethyl acetate and the combined organic fractions were washed with water and brine, dried over Na$_2$SO$_4$ and concentrated. The product was purified by column chromatography on silica gel (ethyl acetate/dichloromethane) to afford N-[3-(2-amino-1,3-thiazol-5-yl)phenyl]-4-(trifluoromethyl)-pyrimidin-2-amine (30.1 mg, 69.7%) as a beige solid. APCI [M+H]$^+$ m/z 338.1 $^1$H NMR (400 MHz, Acetone-d6): δ 9.21 (br s, 1H); 8.82 (d, J=4.9 Hz, 1H); 8.12 (s, 1H); 7.67 (d, J=8.2 Hz, 1H); 7.37 (s, 1H); 7.33 (t, J=8.0 Hz, 1H); 7.24 (d, J=4.9 Hz, 1H); 7.18 (d, J=7.8 Hz, 1H); 6.48-6.41 (m, 2H). rhSYK activity=+++

EXAMPLE 182

2-oxo-2-{[5-(3-{[4-(trifluoromethyl)pyrimidin-2-yl]amino}phenyl)-1,3-thiazol-2-yl]amino}ethyl acetate

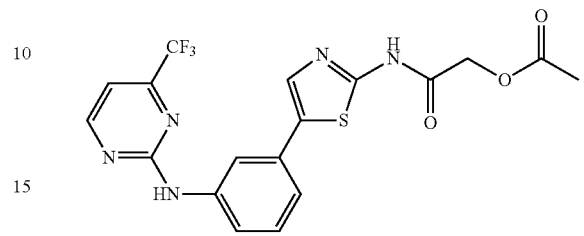

To a suspension of N-[3-(2-amino-1,3-thiazol-5-yl)phenyl]-4-(trifluoromethyl)pyrimidin-2-amine (26 mg, 0.077 mmol) in CH$_2$Cl$_2$ (1 mL) at room temperature, under nitrogen, was added Hunig's Base (0.040 mL, 0.231 mmol) and acetoxyacetyl chloride (9.11 µL, 0.085 mmol) dropwise. The heterogenous mixture was stirred at room temperature for 17 hours, diluted with a large amount of 2-methyl THF, and washed with 5% aqueous NaHCO$_3$, water and brine. The organic fraction was dried over Na$_2$SO$_4$ and concentrated to give a beige solid. The solid was dissolved in DMSO (2 mL) and purified by reverse phase chromatography (MeCN/30 mM NH$_4$HCO$_3$ 40-80%) to afford 2-oxo-2-{[5-(3-{[4-(trifluoromethyl)pyrimidin-2-yl]amino}phenyl)-1,3-thiazol-2-yl]amino}ethyl acetate (Example 182, 8.3 mg, 25%). APCI [M+H]$^+$ m/z 438.0. $^1$H NMR (400 MHz, DMSO-d6): δ 11.71 (br s, 1H); 10.29 (s, 1H); 8.85 (d, J=4.9 Hz, 1H); 8.06 (s, 1H); 7.77 (s, 1H); 7.63 (d, J=8.1 Hz, 1H); 7.36 (t, J=7.9 Hz, 1H); 7.32-7.26 (m, 2H); 4.75 (s, 2H); 2.13 (s, 3H). rhSYK activity=+++

EXAMPLE 183

2-hydroxy-N-[5-(3-{[4-(trifluoromethyl)pyrimidin-2-yl]amino}phenyl)-1,3-thiazol-2-yl]acetamide

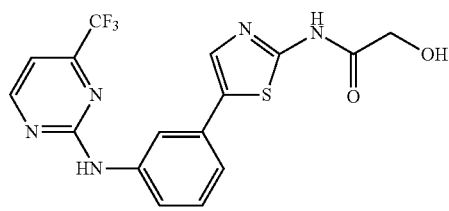 [SMILES: O=C(CO)Nc1ncc(-c2cccc(Nc3nccc(C(F)(F)F)n3)c2)s1]

To a suspension of 2-oxo-2-{[5-(3-{[4-(trifluoromethyl)pyrimidin-2-yl]amino}phenyl)-1,3-thiazol-2-yl]amino}ethyl acetate 1 (8.3 mg, 0.019 mmol) in MeOH (1 mL) at room temperature, under nitrogen, was added potassium carbonate (5.25 mg, 0.038 mmol). The mixture was stirred at room temperature for 18 hours. The mixture was filtered through celite and concentrated to dryness. The product was purified by column chromatography on silica gel (ethanol/ethyl acetatee) to afford 2-hydroxy-N-[5-(3-{[4-(trifluoromethyl)pyrimidin-2-yl]amino}phenyl)-1,3-thiazol-2-yl]acetamide (2.3 mg, 30.7%) as a beige solid. APCI [M+H]$^+$ m/z 396.0. $^1$H NMR (400 MHz, DMSO): δ 11.86 (s, 1H); 10.31 (s, 1H); 8.86 (d, J=4.9 Hz, 1H); 8.12 (s, 1H); 7.82 (s, 1H); 7.65 (d, J=8.0 Hz, 1H); 7.42-7.23 (m, 3H); 5.55 (t, J=6.3 Hz, 1H); 4.18 (d, J=6.0 Hz, 2H). rhSYK activity=+++

EXAMPLE 184

N-(3-[2-(3-oxo-1,4-diazepan-1-yl)-1,3-thiazol-5-yl]-5-{[4-(trifluoromethyl)pyrimidin-2-yl]amino}phenyl)acetamide

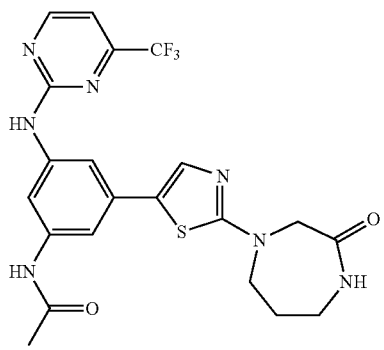 [SMILES: CC(=O)Nc1cc(Nc2nccc(C(F)(F)F)n2)cc(-c2cnc(N3CCCNC(=O)C3)s2)c1]

Step 1:

4-(5-Bromo-1,3-thiazol-2-yl)-1,4-diazepan-2-one (Step 5 of Intermediate XX, 1.96 g, 7.10 mmol), (3-amino-5-nitrophenyl)boronic acid (1.291 g, 7.10 mmol), tetrakis-(triphenylphosphine)palladium(0) (0.410 g, 0.355 mmol), 1,2-dimethoxyethane (42 mL) and 2M aqueous sodium carbonate (10.65 mL, 21.29 mmol) were successively introduced in a high pressure reaction vessel. The headspace was flushed with nitrogen, the vessel capped and the mixture was stirred at 100° C. for 18 h. The reaction was then cooled to room temperature and 25% aqueous ammonium acetate was added. The aqueous layer was extracted with ethyl acetate (3×). The combined organics were washed with brine, dried over sodium sulfate, and concentrated under reduced pressure. Purification via CombiFlash (ethanol/ethyl acetate) afforded 590 mg (1.77 mmol, 25% yield) of 4-[5-(3-amino-5-nitrophenyl)-1,3-thiazol-2-yl]-1,4-diazepan-2-one as a yellow solid. MS APCI: [M+H]+ m/z 334.1.

Step 2:

4-[5-(3-Amino-5-nitrophenyl)-1,3-thiazol-2-yl]-1,4-diazepan-2-one (482 mg, 1.446 mmol), XantPhos (251 mg, 0.434 mmol), cesium carbonate (942 mg, 2.89 mmol), palladium (II) acetate (64.9 mg, 0.289 mmol), dioxane (10 mL) and 2-chloro-4-(trifluoromethyl)pyrimidine (0.174 mL, 1.446 mmol) were successively added in a sealable reaction tube under nitrogen. The tube was sealed and the mixture was stirred at 125° C. for 5 hours. The reaction mixture was cooled to room temperature, partitioned between 25% aqueous ammonium acetate and ethyl acetate. The aqueous layer was extracted twice with ethyl acetate and three times with 2-methyltetrahydrofuran. The combined organic layers were washed with brine, dried over sodium sulfate, and concentrated under reduced pressure. Purification via CombiFlash (ethanol/dichloromethane) afforded 4-[5-(3-nitro-5-{[4-(trifluoromethyl)pyrimidin-2-yl]amino}phenyl)-1,3-thiazol-2-yl]-1,4-diazepan-2-one as an amber gum. MS APCI: [M+H]+ m/z 480.1.

Step 3:

To a suspension of 4-[5-(3-nitro-5-{[4-(trifluoromethyl)pyrimidin-2-yl]amino}phenyl)-1,3-thiazol-2-yl]-1,4-diazepan-2-one (410 mg, 0.855 mmol) in tetrahydrofuran (4.5 mL) at room temperature, under nitrogen, were successively added triethylamine (0.179 mL, 1.28 mmol), N,N-dimethylpyridin-4-amine (10.45 mg, 0.086 mmol) and di-tert-butyl dicarbonate (205 mg, 0.941 mmol). The mixture was stirred at room temperature for 60 h after which a yellow solution was obtained. The mixture was diluted with ethyl acetate, washed with water and brine, dried over sodium sulfate, and concentrated under reduced pressure. The resulting residue was purified via CombiFlash (ethanol/dichloromethane) to provide 316 mg (0.545 mmol, 64% yield) of tert-butyl{3-nitro-5-[2-(3-oxo-1,4-diazepan-1-yl)-1,3-thiazol-5-yl]phenyl}[4-(trifluoromethyl)pyrimidin-2-yl]carbamate as a yellow solid. MS APCI: [M+H]m/z 580.1.

Step 4:

To a suspension of tert-butyl {3-nitro-5-[2-(3-oxo-1,4-diazepan-1-yl)-1,3-thiazol-5-yl]phenyl}[4-(trifluoromethyl)pyrimidin-2-yl]carbamate (314 mg, 0.542 mmol) in ethanol (9 mL) at room temperature under nitrogen, was added iron (605 mg, 10.84 mmol) and a saturated aqueous solution of ammonium chloride (0.25 mL). The mixture was stirred at 40° C. for 30 minutes. N,N'-dimethylformamide (5 mL) was added and the mixture was stirred at 40° C. for 3 hours. An additional portion of iron (300 mg, 5.4 mmol) and saturated aqueous solution of ammonium chloride (1.1 mL) were then added and the resulting mixture was stirred at 40° C. for 2 hours. The reaction was then cooled to room temperature, and concentrated under reduced pressure to remove volatiles. The resulting suspension was filtered through celite, rinsing successively with N,N'-dimethylformamide, ethyl acetate, dichloromethane, and 2-methyltetrahydrofuran. The filtrate was concentrated to remove the volatiles, then diluted with ethyl acetate, washed with water (5×), brine (1×), dried over sodium sulfate, and concentrated to provide a beige solid. This solid was swished in 1:1 ethyl acetate/hexane, the solids collected by filtration, rinsed successively with 1:1 ethyl acetate/hexane and hexane, and dried to afford 250 mg (0.46 mmol, 85%) of tert-butyl {3-amino-5-[2-(3-oxo-1,4-diazepan-1-yl)-1,3-thiazol-5-yl]phenyl}[4-(trifluoromethyl)pyrimidin-2-yl]carbamate as a beige solid.

Step 5:

To a suspension of tert-butyl {3-amino-5-[2-(3-oxo-1,4-diazepan-1-yl)-1,3-thiazol-5-yl]phenyl}[4-(trifluoromethyl)pyrimidin-2-yl]carbamate (125 mg, 0.227 mmol) in dichloromethane (2.5 mL) at room temperature, under nitrogen, was added triethylamine (0.079 mL, 0.569 mmol) and acetyl chloride (0.024 mL, 0.341 mmol). The mixture was stirred at room temperature for 18 h after which time a solution was obtained. The mixture was diluted with ethyl acetate and washed with water and brine, and dried over sodium sulfate. Silica gel (1 g) was added and the solution concentrated to dryness. The resulting solid was purified by silica gel chromatography (ethanol/dichloromethane eluant) to afford 80 mg (0.135 mmol, 60% yield) of tert-butyl {3-(acetylamino)-5-[2-(3-oxo-1,4-diazepan-1-yl)-1,3-thiazol-5-yl]phenyl}[4-(trifluoromethyl)pyrimidin-2-yl]carbamate as an off-white solid.

Step 6:

To a solution of tert-butyl {3-(acetylamino)-5-[2-(3-oxo-1,4-diazepan-1-yl)-1,3-thiazol-5-yl]phenyl}[4-(trifluoromethyl)pyrimidin-2-yl]carbamate (79 mg, 0.134 mmol) in dichloromethane (1 mL) at room temperatrue, under nitrogen, was added trifluoroacetic acid (1 mL, 13 mmol). The mixture was stirred at room temperature for 1 h and concentrated to dryness. The residue was partitioned between ethyl acetate and 5% aqueous sodium bicarbonate. The solid product precipitated in the two phases. The organic layer was concentrated to dryness and the residue was transferred into the aqueous with a small amount of EtOH. The resulting aqueous suspension was filtered, the solids collected, and washed with water, a small amount of ethanol, then hexane, and dried to afford 48 mg (0.098 mmol, 73% yield) of N-(3-[2-(3-oxo-1,4-diazepan-1-yl)-1,3-thiazol-5-yl]-5-{[4-(trifluoromethyl)pyrimidin-2-yl]amino}phenyl)acetamide as an off-white solid. MS APCI: [M+H]$^+$ m/z 492.1. $^1$H NMR (400 MHz, d6-dmso): δ 10.25 (s, 1H); 9.98 (s, 1H); 8.82 (d, J=4.9 Hz, 1H); 7.75 (m, 2H); 7.61 (br t, J=5.0 Hz, 1H); 7.43-7.37 (m, 2H); 7.28 (d, J=4.9 Hz, 1H); 4.19 (s, 2H); 3.81 (m, 2H); 3.24 (m, 2H); 2.05 (s, 3H); 1.80 (m, 2H). rhSyk=+++.

EXAMPLE 185

1-ethyl-3-(3-[2-(3-oxo-1,4-diazepan-1-yl)-1,3-thiazol-5-yl]-5-{[4-(trifluoromethyl)pyrimidin-2-yl]amino}phenyl)urea

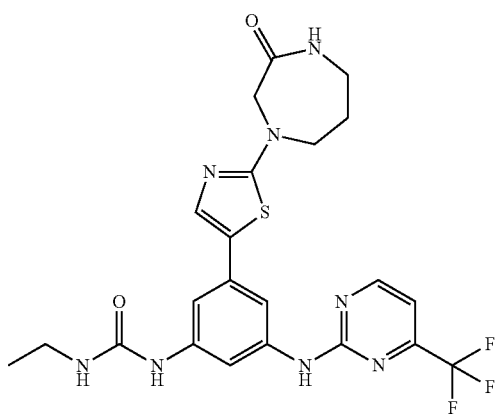 [SMILES: CCNC(=O)Nc1cc(Nc2nccc(C(F)(F)F)n2)cc(-c2cnc(N3CCCNC(=O)C3)s2)c1]

The title compound was prepared in an analogous manner of that described in Example 184. [M+H]+ observed 521.1. rhSyk=+++.

EXAMPLE 186

N-(3-{2-[2-Hydroxyethyl)(methyl)amino]-1,3-thiazol-5-yl}-5-{[4-(trifluoromethyl)pyrimidin-2-yl]amino}) phenyl)acetamide

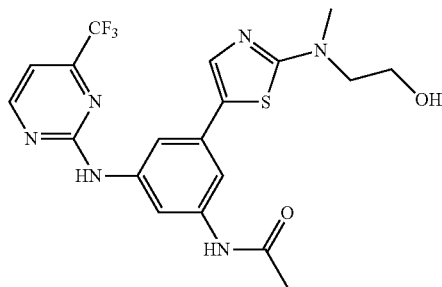 [SMILES: CC(=O)Nc1cc(Nc2nccc(C(F)(F)F)n2)cc(-c2cnc(N(C)CCO)s2)c1]

Step 1:

1,3-Dinitrobenzene (25 g, 149 mmol) was dissolved in sulfuric acid (44.5 mL, 835 mmol) and NBS (31.8 g, 178 mmol) was added. The mixture was stirred at 60° C. for 2 days. The reaction was cooled to ambient temperature and the mixture was poured into ice water to form a precipitate. The product was collected by filtration, washed with water and hexanes to yield 35.1 g (142 mmol, 96%) of 1-bromo-3,5-dinitrobenzene as a beige solid.

Step 2:

1-Bromo-3,5-dinitrobenzene (14.77 g, 59.8 mmol) was dissolved in methanol (150 mL) and toluene (374 mL) and a solution of sodium hydrosulfide (10.06 g, 179 mmol) in water (10 mL) and methanol (150 mL) was added dropwise over a period of 60 minutes. The reaction was stirred at 80° C. for 3 hours. The reaction mixture was cooled to room temperature and then extracted 3 times with ethyl acetate. The organic layers were combined, washed with brine, dried with MgSO$_4$, filtered, and concentrated under reduced pressure. The crude material required no further purification to yield 12.93 g (59.6 mmol, 100%) of 3-bromo-5-nitroaniline.

Step 3:

3-Bromo-5-nitroaniline (6.45 g, 29.7 mmol) was dissolved in dichloromethane (149 mL) and pyridine (2.88 mL, 35.7 mmol). The solution was cooled to 0° C. and then, acetyl chloride (2.325 mL, 32.7 mmol) was added dropwise. The reaction mixture was stirred at 0° C. for 1 hour. The reaction was diluted with water and dichloromethane and the organic phase was dried over sodium sulfate and was concentrated to dryness. N-(3-bromo-5-nitrophenyl)acetamide was isolated as a beige powder (7.86 g, 30 mmol, 100%) and was of sufficient purity to carry forward without further purification.

Step 4:

N-(3-bromo-5-nitrophenyl)acetamide (4 g, 15.44 mmol) was dissolved in ethanol (154 mL) and saturated NH$_4$Cl(aq) (2 mL). Iron (2.59 g, 46.3 mmol) was added to the solution the reaction mixture was heated to 80° C. for 30 minutes. Upon completion, the reaction was cooled to room temperature and filtered through a short pad of silica gel (ethyl acetate wash). The organic was dried over sodium sulfate, filtered, and concentrated under reduced pressure. N-(3-amino-5-bromophenyl)acetamide was isolated as a beige foam (3.25 g, 14.19 mmol, 92%).

Step 5:

To a solution of N-(3-amino-5-bromophenyl)acetamide (3.25 g, 14.19 mmol) and 2-chloro-4-(trifluoromethyl)pyrimidine (2.054 mL, 17.03 mmol) in dioxane (8.5 mL) under nitrogen, was added pTsOH (2.70 g, 14.19 mmol). The reaction was stirred at 100° C. for 18 h, cooled to at room temperature. Solvent was removed under reduced pressure and the resultant residue was diluted with sat. NaH-CO$_3$ (aq) and DCM. The organic was dried over sodium sulfate and was concentrated to dryness. Purified by flash chromatography (1:1 to 0:100 hexanes:ethyl acetate) to yield N-(3-bromo-5-{[4-(trifluoromethyl)pyrimidin-2-yl]amino}phenyl)acetamide (2.71 g, 7.22 mmol, 51%) as a beige powder. MS APCI: [M+H]m/z 377.0.

Step 6:

N-(3-bromo-5-{[4-(trifluoromethyl)pyrimidin-2-yl]amino}phenyl)acetamide (150 mg, 0.400 mmol), 2-(trimethylsilyl)-5-(trimethylstannanyl)-1,3-thiazole (141 mg, 0.440 mmol) (prepared using literature procedure: Dondoni, A.; Mastellari, A. R.; Medici, A.; Negrini, E.; Pedrini, P. *Synthesis* 1986, 9, 757-760) and Pd(Ph$_3$P)$_4$ (46.2 mg, 0.040 mmol) were placed in a nitrogen purged microwave vial. Dioxane (2 mL) was added and the resultant solution was purged for 10 minutes with nitrogen gas. The reaction mixture was heated to 90° C. for 15 h. Note: Under the reaction conditions the TMS group is removed. The reaction mixture was concentrated and directly purified by column chromatography to yield 130 mg of N-[3-(1,3-thiazol-5-yl)-5-{[4-(trifluoromethyl)pyrimidin-2-yl]amino}phenyl]acetamide (0.343 mmol, 86%) as a yellow powder.

Step 7:

A microwave vial containing N-[3-(1,3-thiazol-5-yl)-5-{[4-(trifluoromethyl)pyrimidin-2-yl]amino}phenyl]acetamide (50 mg, 0.132 mmol) in THF (659 μL) was cooled to −78° C. in a dry ice-acetone bath. To the solution was added a stock solution of LDA prepared from the addition of n-BuLi (3.47 μL, 1.52 M, 0.527 mmol) over diisopropylamine (54.7 mg, 0.540) in THF at −78° C. After stirring the suspension for 20 minutes, a solution of NBS (94 mg, 0.527 mmol) in THF (1 mL) was added. The resulting yellow suspension was stirred at −78° C. for 1 h, after which the bath was removed. Once at room temperature, the reaction was treated with sat. NaHCO₃(aq) and the phases were separated. The aqueous was extracted 3 times with ethyl acetate. Organic layers were combined, washed with brine, dried with MgSO₄, filtered and concentrated under reduced pressure. The residual solid was purified by flash chromatography to yield N-[3-(2-bromo-1,3-thiazol-5-yl)-5-{[4-(trifluoromethyl)pyrimidin-2-yl]amino}phenyl]-acetamide as a beige powder (29 mg, 0.063 nmol, 48%).

Step 8:

N-[3-(2-Bromo-1,3-thiazol-5-yl)-5-{[4-(trifluoromethyl)pyrimidin-2-yl]amino}phenyl]-acetamide (521 mg, 1.137 mmol) was dissolved in Butan-1-ol (2.27 mL). 2-(methylamino)-ethanol (100 μL, 1.251 mmol) was added and the reaction was stirred at 130° C. for 15 h. The reaction was cooled to room temperature and the product was titurated by the addition of diethyl ether. N-(3-{2-[(2-Hydroxyethyl)(methyl)amino]-1,3-thiazol-5-yl}-5-{[4-(trifluoromethyl)-pyrimidin-2-yl]amino}phenyl)acetamide was collected by filtration (diethyl ether wash) to yield 280 mg (0.619 mmol, 54%). MS APCI: [M+H]⁺ m/z 453.1. ¹H NMR (400 MHz, Acetone): δ 9.24 (d, J=12.1 Hz, 1H); 8.81 (d, J=4.9 Hz, 1H); 7.96 (s, 1H); 7.87 (s, 1H); 7.57 (s, 1H); 7.43 (s, 1H); 7.23 (d, J=4.9 Hz, 1H); 3.83 (t, J=5.6 Hz, 2H); 3.67 (t, J=5.6 Hz, 2H); 3.20 (s, 3H); 2.11 (s, 3H).

rhSYK activity=+++

The following examples were prepared in an analogous manner of that described in Example 186.

| Example | R¹ | R² | rhSYK Activity | [M + H]+ Obs'd | Form(s) |
|---------|-----|-----|----------------|----------------|---------|
| 187 | —C(O)CH₃ | H | +++ | 439.1 | Free Base |
| 188 | —C(O)NHEt | H | +++ | 468.1 | Free Base |
| 189 | H | CH₃ | +++ | 411.1 | Free Base |
| 190 | H | H | +++ | 397.1 | Free Base |

EXAMPLE 191

1-[5-(3-{[4-(trifluoromethyl)pyrimidin-2-yl]amino}phenyl)-1,3-thiazol-2-yl]piperidine-4-carboxamide

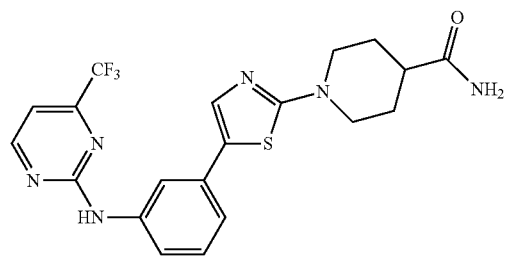 [SMILES: NC(=O)C1CCN(c2ncc(-c3cccc(Nc4nccc(C(F)(F)F)n4)c3)s2)CC1]

Step 1:

A mixture of 2-bromo-1,3-thiazole (522 mg, 3.18 mmol) and ethyl piperidine-4-carboxylate (1 g, 6.36 mmol) was heated to 100° C. neat overnight, then cooled to room temperature. The residue was dissolved in dichloromethane and directly purified by CombiFlash (0-40% ethyl acetate/hexanes) to provide 654 mg (2.7 2 mmol, 86% yield) of ethyl 1-(1,3-thiazol-2-yl)piperidine-4-carboxylate as a colorless oil.

Step 2:

Bromine (0.14 mL, 2.7 mmol) was weighed into a vial and then diluted with acetic acid (1 mL). This solution was added dropwise (over 10 minutes) to a solution of ethyl 1-(1,3-thiazol-2-yl)piperidine-4-carboxylate (650 mg, 2.7 mmol) in acetic acid (12.5 mL). The mixture was then diluted with ethyl acetate (100 mL) and washed with water (100 mL) and brine (100 mL). The organic layer was dried over sodium sulfate and concentrated in vacuo to provide 840 mg (2.63 mmol, 97% yield) of ethyl 1-(5-bromo-1,3-thiazol-2-yl)piperidine-4-carboxylate as a green oil.

Step 3:

A mixture of (3-nitrophenyl)boronic acid (188 mg, 1.13 mmol), ethyl 1-(5-bromo-1,3-thiazol-2-yl)piperidine-4-carboxylate (300 mg, 0.94 mmol), palladium(II) acetate (10.5 mg, 0.047 mmol), and tris(2-methylphenyl)phosphane (286 mg, 0.94 mmol) in 1,2-dimethoxyethane (1.9 mL) and 2M aqueous sodium carbonate (0.7 mL, 1.4 mmol) was heated to 100° C. in the microwave for 30 minutes. After cooling to room temperature, the mixture was diluted with ethyl acetate (100 mL) and washed with 1:1 water:brine (50 mL). The organic layer was dried over sodium sulfate and concentrated in vacuo. Purification by CombiFlash (0-40% ethyl acetate/hexanes) provided 79 mg (0.22 mmol, 23% yield) of ethyl 1-[5-(3-nitrophenyl)-1,3-thiazol-2-yl]piperidine-4-carboxylate as a yellow solid.

Step 4:

To a solution of ethyl 1-[5-(3-nitrophenyl)-1,3-thiazol-2-yl]piperidine-4-carboxylate (75 mg, 0.21 mmol) in ethyl acetate (1.9 mL) and acetic acid (0.19 mL) was added 10% palladium on carbon (22 mg, 0.021 mmol), and the mixture was stirred under an atmosphere of hydrogen (balloon) for 3 hours. The mixture was filtered through celite, washing with ethyl acetate and the filtrate concentrated under reduced pressure. Purification by CombiFlash (30-70% ethyl acetate:hexanes) provided 60 mg (0.18 mmol, 87% yield) of ethyl 1-[5-(3-aminophenyl)-1,3-thiazol-2-yl]piperidine-4-carboxylate.

Step 5:

To a solution of ethyl 1-[5-(3-aminophenyl)-1,3-thiazol-2-yl]piperidine-4-carboxylate (42 mg, 0.13 mmol) in dioxane (1.3 mL) was added 2-chloro-4-(trifluoromethyl)pyrimidine (23 mg, 1.3 mmol) and 4-methylbenzenesulfonic acid (24 mg, 0.127 mmol), resulting in the instant formation of a suspension. The mixture was heated to 100° C. and N,N-dimethylformamide (0.5 mL) was added to afford a homogenous mixture. The solution was heated at 100° C. for an additional 2 hours. Thus the mixture was the cooled to room temperature, diluted with ethyl acetate (30 mL), and washed with saturated aqueous sodium bicarbonate (30 mL) and brine (30 mL). The aqueous fractions were further extracted with ethyl acetate (30 mL). The combined organic extracts were dried over sodium sulfate and concentrated under reduced pressure. Purification by CombiFlash (30-100% ethyl acetate:hexanes) provided 22 mg (0.046 mmol, 36% yield) of ethyl 1-[5-(3-{[4-(trifluoromethyl)pyrimidin-2-yl]amino}phenyl)-1,3-thiazol-2-yl]piperidine-4-carboxylate as a white solid.

Step 6:

To a solution of ethyl 1-[5-(3-{[4-(trifluoromethyl)pyrimidin-2-yl]amino}phenyl)-1,3-thiazol-2-yl]piperidine-4-carboxylate (22 mg, 0.046 mmol) in tetrahydrofuran (0.5 mL) and methanol (0.5 mL) was added 1M aqueous lithium hydroxide (0.5 mL, 0.5 mmol) and the mixture was heated to 90° C. for 90 minutes. The mixture was cooled to room temperature, diluted with 2-methyltetrahydrofuran (30 mL), and, washed with 1 N aqueous hydrochloric acid (30 mL) and brine (30 mL). The aqueous layers were further extracted with 2-methyltetrahydrofuran (30 mL). The combined organic extracts were dried over sodium sulfate and concentrated in vacuo to provide 1-[5-(3-{[4-(trifluoromethyl)pyrimidin-2-yl]amino}phenyl)-1,3-thiazol-2-yl]piperidine-4-carboxylic acid as a white solid. MS APCI: [M+H]$^+$ m/z 450.1.

Step 7:

To a solution of 1-[5-(3-{[4-(trifluoromethyl)pyrimidin-2-yl]amino}phenyl)-1,3-thiazol-2-yl]piperidine-4-carboxylic acid (15 mg, 0.033 mmol) in N,N-dimethylformamide (0.33 mL) was added ammonium chloride (5.4 mg, 0.10 mmol), diisopropylethylamine (23 µL, 0.13 mmol) and then (1H-benzotriazol-1-yloxy)(tripyrrolidin-1-yl)phosphonium hexafluorophosphate (35 mg, 0.067 mmol). After stirring for 90 minutes at room temperature, the mixture was diluted with EtOAc (30 mL), then washed with 1:1 saturated aqueous sodium bicarbonate:brine (2×30 mL). The aqueous fractions were further extracted with EtOAc (30 mL). The combined organic extracts were dried over sodium sulfate, and concentrated under reduced pressure. Purification by reverse phase HPLC provided 7 mg (0.016 mmol, 47% yield) of 1-[5-(3-{[4-(trifluoromethyl)pyrimidin-2-yl]amino}phenyl)-1,3-thiazol-2-yl]piperidine-4-carboxamide. MS APCI: [M+H]$^+$ m/z 449.1. $^1$H NMR (400 MHz, DMSO): δ 10.26 (s, 1H); 8.84 (d, J=4.9 Hz, 1H); 8.01 (s, 1H); 7.57-7.49 (m, 2H); 7.35-7.26 (m, 3H); 7.16 (d, J=7.7 Hz, 1H); 6.85 (s, 1H); 3.93 (d, J=12.8 Hz, 2H); 3.14-2.98 (m, 2H); 2.42-2.31 (m, 1H); 1.91-1.69 (m, 2H); 1.69-1.55 (m, 2H). rhSyk=+++.

EXAMPLES 192/193

1-(5-{3-[(4-methylpyrimidin-2-yl)amino]phenyl}-1,3-thiazol-2-yl)piperidine-4-carboxamide; 1-(5-{3-[(4-methylpyrimidin-2-yl)amino]phenyl}-1,3-thiazol-2-yl)piperidine-4-carboxylic acid

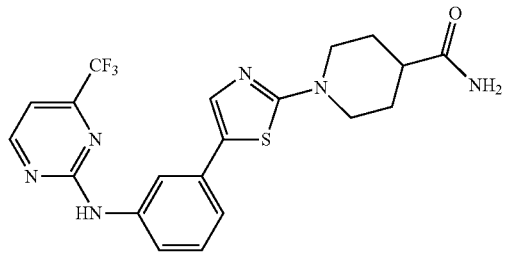

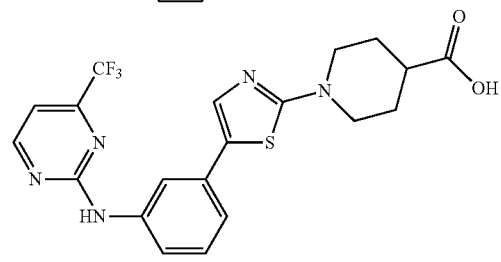

The title compounds were prepared in an analogous manner of that described in Example 191. [M+H]+ Observed 395.1 (Example 192) and 396.1 (Example 193). rhSyk=++ for both compounds.

EXAMPLE 194

2,2'-({5-[3-(morphpholin-4-yl)-5-{[4-(trifluoromethyl)pyrimidin-2-yl]amino}phenyl]-1,3-thiazol-2-yl}imino)diethanol

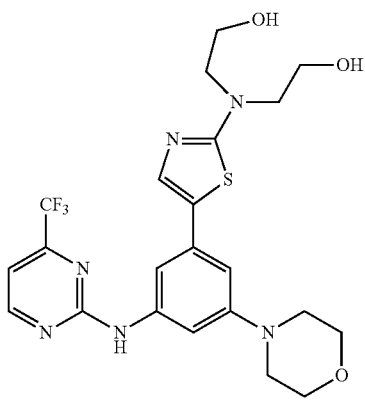 [SMILES: OCCN(CCO)c1ncc(-c2cc(Nc3nccc(C(F)(F)F)n3)cc(N3CCOCC3)c2)s1]

Step 1:

In a sealable tube were added 4-(3-iodo-5-nitrophenyl)morpholine (Intermediate X, 1.0 g, 2.99 mmol), 4,4,4',4',5,5,5',5'-octamethyl-2,2'-bi-1,3,2-dioxaborolane (0.84 g, 3.29 mmol), potassium acetate (1.11 g, 11.3 mmol), 1,1'-bis (diphenylphosphino)ferrocenepalladium(II) dichloride dichloromethane complex (0.073 g, 0.09 mmol) and dimethylsulfoxide (17 mL) at room temperature, under nitrogen. The tube was capped and the mixture was irradiated in the microwave at 125° C. for 30 minutes, cooled to room temperature and poured into water (200 mL). The mixture was extracted with ethyl acetate (3×). The combined organics were washed with 1:1 brine/water (2×) and brine, dried over sodium sulfate, filtered, and concentrated under reduced pressure to provide 1.13 g (quantitative) of 4-[3-nitro-5-(4,4,5,5-tetramethyl-1,3,2-dioxaborolan-2-yl)phenyl]morpholine as a brown residue.

Step 2:

In a sealable tube were successively added diethanolamine (3.46 mL, 35.8 mmol) and 2-bromothiazole (1.538 mL, 17.07 mmol), under nitrogen. The tube was sealed and the mixture was irradiated in the microwave at 130° C. for 30 min. The residue was dissolved in 5:95 ethanol:dichloromethane and chromatographed on silica (CombiFlash, 5-20%, ethanol in dichloromethane) to afford 2,2'-(1,3-thiazol-2-ylimino)diethanol (795 mg, 4.22 mmol, 24.74% yield) as a pale oil.

Step 3:

To a solution of 2,2'-(1,3-thiazol-2-ylimino)diethanol (1.27 g, 6.75 mmol) and imidazole (2.296 g, 33.7 mmol) in DMF (28 mL) at room temperature, under nitrogen, was added tert-butyldiphenylchlorosilane (4.16 mL, 16.19 mmol) dropwise. The mixture was stirred at room temperature for 18 h and poured into 5% aqueous $NaHCO_3$. The aqueous layer was extracted with ethyl acetate (3×). The combined organics were washed with water (3×) and brine, dried ($Na_2SO_4$) and concentrated to give a pale oil (5.7 g). Chromatography on silica (CombiFlash, 5-25% ethyl acetate in hexane) afforded N,N-bis(2-{[tert-butyl(diphenyl)silyl]oxy}ethyl)-1,3-thiazol-2-amine (3.89 g, 5.85 mmol, 87% yield) as a pale gum.

Step 4:

To a solution of N,N-bis(2-{[tert-butyl(diphenyl)silyl]oxy}ethyl)-1,3-thiazol-2-amine (3.88 g, 5.83 mmol) and triethylamine (1.252 mL, 8.98 mmol) in chloroform (2 mL) at room temperature, under nitrogen, was added bromine (0.463 mL, 8.98 mmol) dropwise (5 min.). The mixture was stirred at room temperature for 2 h, diluted with chloroform, washed successively with 5% aqueous $NaHCO_3$, 10% aqueous $Na_2S_2O_3$ and brine, dried ($Na_2SO_4$) and concentrated to give an amber oil (4.6 g). Chromatography (CombiFlash, 0-20% ethyl acetate in hexanes) afforded 5-bromo-N,N-bis(2-{[tert-butyl(diphenyl)silyl]oxy}ethyl)-1,3-thiazol-2-amine (3.56 g, 4.79 mmol, 82% yield) as off-white crystals.

Step 5:

4-[3-nitro-5-(4,4,5,5-tetramethyl-1,3,2-dioxaborolan-2-yl)phenyl]morpholine (1.137 g, 3.40 mmol) in DME (11 mL), 5-bromo-N,N-bis(2-{[tert-butyl(diphenyl)silyl]oxy}ethyl)-1,3-thiazol-2-amine (2.11 g, 2.84 mmol), 1,1'-bis(diphenylphosphino)ferrocene-palladium(II)-dichloride dichloromethane complex (0.116 g, 0.142 mmol) and sodium carbonate (2M, 4.25 mL, 8.51 mmol) were successively introduced in a reaction tube, under nitrogen. The tube was sealed and the mixture was irradiated at 125° C. for 30 min. under microwaves and cooled to room temperature. The reaction was quenched by the addition of 25% aqueous $NH_4OAc$. Ethyl acetate was added and the mixture was filtrated through Celite (emulsion). The aqueous layer was extracted with ethyl acetate (3×). The combined organics were washed with water and brine, dried ($Na_2SO_4$) and concentrated to give a brown residue (2.9 g). Chromatography on silica (CombiFlash, 0-10% ethyl acetate in dichloromethane) afforded N,N-bis(2-{[tert-butyl-(diphenyl)silyl]oxy}ethyl)-5-[3-(morpholin-4-yl)-5-nitrophenyl]-1,3-thiazol-2-amine (1.01 g, 1.159 mmol, 40.9% yield) as a deep yellow gum.

Step 6:

To a solution of N,N-bis(2-{[tert-butyl(diphenyl)silyl]oxy}ethyl)-5-[3-(morpholin-4-yl)-5-nitrophenyl]-1,3-thiazol-2-amine (999 mg, 1.147 mmol) in ethyl acetate (10 mL) and acetic acid (1.000 mL) at R.T., under nitrogen, was added palladium on carbon (122 mg, 0.115 mmol). The mixture was purged 3 times alternating between vacuum and $H_2$. The reaction mixture was stirred under 1 atm $H_2$ for 2 h. The system was evacuated with vacuum and purged 3 times alternating between vacuum and $N_2$, and 3 mL DCM were added. The mixture was filtered through a pad of celite. The pad was rinsed with ethyl acetate and the filtrate concentrated. Residual AcOH was azeotroped with toluene (3×) to give 5-[3-amino-5-(morpholin-4-yl)phenyl]-N,N-bis(2-{[tert-butyl(diphenyl)silyl]oxy}ethyl)-1,3-thiazol-2-amine as a yellow gum (958 mg, 1.139 mmol, 99%).

Step 7:

5-[3-Amino-5-(morpholin-4-yl)phenyl]-N,N-bis(2-{[tert-butyl(diphenyl)silyl]oxy}ethyl)-1,3-thiazol-2-amine (936 mg, 1.113 mmol) in dioxane (8 mL), 2-chloro-4-(trifluoromethyl)-pyridimidine (0.134 mL, 1.113 mmol), 9,9-dimethyl-4,5-bis(diphenylphosphino)xanthene (193 mg, 0.334 mmol), cesium carbonate (725 mg, 2.225 mmol), and palladium(II) acetate (50.0 mg, 0.223 mmol) were successively added in a sealable reaction tube under nitrogen. The tube was sealed and the mixture was heated in an oil bath at 100° C. for 12 hr and then was cooled to room temperature. The reaction mixture was partitioned between 25% $NH_4OAc$ and ethyl acetate and filtered through a pad of celite. The cake was rinsed with ethyl acetate and the organic layer was washed with water and brine, dried ($Na_2SO_4$) and concentrated to give a brown gum (1.3 g). Chromatography on silica (CombiFlash, 20-50%, ethyl acetate in hexane) afforded N-[3-{2-[bis(2-{[tert-butyl(diphenyl)silyl]oxy}ethyl)amino]-1,3-thiazol-5-yl}-5-(morpholin-4-yl)phenyl]-4-(trifluoromethyl)pyrimidin-2-amine (481 mg, 0.487 mmol, 43.8% yield) as a brown foam.

Step 8:

To a solution of N-[3-{2-[bis(2-{[tert-butyl(diphenyl)silyl]oxy}ethyl)amino]-1,3-thiazol-5-yl}-5-(morpholin-4-yl)phenyl]-4-(trifluoromethyl)pyrimidin-2-amine (470 mg, 0.476 mmol) in THF (2.5 mL) at room temperature, under nitrogen, was added TBAF (2.380 mL, 2.380 mmol). The mixture was stirred for 45 min., poured in water and extracted with ethyl acetate (3×). The combined organics were washed with water and brine, dried ($Na_2SO_4$) and concentrated to give a yellow solid (476 mg). Chromatography on silica (CombiFlash, 0-35%, ethanol in dichloromethane) afforded 2,2'-({5-[3-(morpholin-4-yl)-5-{[4-(trifluoromethyl)pyrimidin-2-yl]amino}phenyl]-1,3-thiazol-2-yl}imino)diethanol (201 mg, 0.394 mmol, 83% yield) as an off-white solid. MS ESI: [M+H]+ m/z 511.1. $^1$H NMR (400 MHz, Acetone): δ 9.09 (s, 1H); 8.81 (d, J=4.9 Hz, 1H); 7.59-7.57 (m, 1H); 7.48-7.45 (m, 2H); 7.22 (d, J=4.9 Hz, 1H); 6.82-6.79 (m, 1H);

4.42 (t, J=5.4 Hz, 1H); 3.86 (t, J=5.5 Hz, 4H); 3.81 (t, J=4.6 Hz, 4H); 3.71 (t, J=5.4 Hz, 4H); 3.24-3.20 (m, 4H). rhSYK activity=+++

EXAMPLE 195

4-(5-({3-[(4-cyclobutylpyrimidin-2-yl)amino]-5-methylphenyl}-1,3-thiazol-2-yl)-1,4-diazepan-2-one

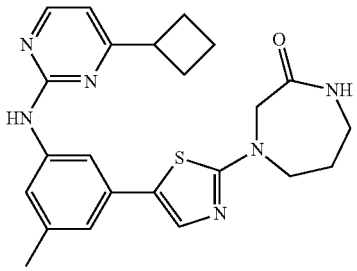 [SMILES: Cc1cc(Nc2nccc(C3CCC3)n2)cc(-c2cnc(N3CCCNC(=O)C3)s2)c1]

Step 1:

2,4-Dichloropyrimidine (250 mg, 1.68 mmol) and ferric acetylacetonate (30 mg, 0.08 mmol) were taken up in tetrahydrofuran (3.4 ml) and the reaction was cooled to −78° C. Cyclobutylmagnesium chloride (3.4 ml of 0.5 M, 1.68 mmol) was added dropwise and the mixture was stirred at −78° C. for 30 min. The mixture was quenched with aqueous ammonium chloride and extracted with ethyl acetate. The combined organic fractions were washed with aqueous sodium hydrogen carbonate, dried over magnesium sulfate, filtered, and the solvent was evaporated under reduced pressure. The residue was purified by Combiflash (0-5% ethyl acetate in hexanes) to provide 121 mg (0.72 mmol, 43%) of 2-chloro-4-cyclobutylpyrimidine as a colorless oil. MS APCI: [M+H]$^+$ m/z 169.1.

Step 2:

2-Chloro-4-cyclobutylpyrimidine (50 mg, 0.297 mmol), 4-[5-(3-amino-5-methylphenyl)-1,3-thiazol-2-yl]-1,4-diazepan-2-one (Intermediate XX, 90 mg, 0.297 mmol), Pd$_2$(dba)$_3$ (27.2 mg, 0.030 mmol), XPhos (70.7 mg, 0.148 mmol), and potassium carbonate (82 mg, 0.593 mmol) were combined in t-amyl alcohol (0.99 ml). The mixture was purged with argon for 5 minutes, capped, and stirred at 90° C. overnight. The mixture was then cooled to room temperature and loaded directly on the column and was purified by silica gel chromatography (10% methanol/dichloromethane) to provide 98 mg (0.22 mol, 76% yield) of 4-(5-{3-[(4-cyclobutylpyrimidin-2-yl)amino]-5-methylphenyl}-1,3-thiazol-2-yl)-1,4-diazepan-2-one as a tan solid. MS APCI: [M+H]$^+$ m/z 435.2. $^1$H NMR (600 MHz, d6-DMSO) δ 9.48 (s, 1H), 8.32 (d, J=4.8 Hz, 1H), 7.92 (s, 1H), 7.55 (dd, J=4.8 Hz, 5.4 Hz, 1H), 7.43 (s, 1H), 7.38 (s, 1H), 6.88 (s, 1H), 6.66 (d, J=5.4 Hz, 1H), 4.14 (s, 2H), 3.75 (m, 2H), 3.52 (m, 1H), 3.18 (m, 2H), 2.33-2.23 (m, 4H), 2.24 (s, 3H), 2.02 (m, 1H), 1.88 (m, 1H), 1.76 (m, 2H). rhSYK activity=+++

EXAMPLES 196/197

4-(5-{3-[(4-cyclohexylpyrimidin-2-yl)amino]-5-methylphenyl}-1,3-thiazol-2-yl)-1,4-diazepan-2-one; 4-(5-{3-[(4-cyclopentylpyrimidin-2-yl)amino]-5-methylphenyl}-1,3-thiazol-2-yl)-1,4-diazepan-2-one

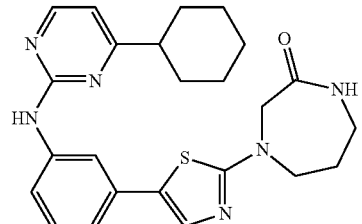

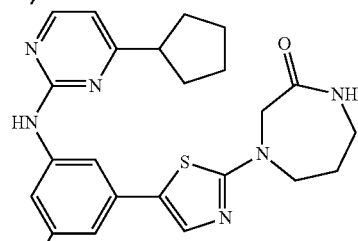

The title compounds were prepared in an analogous manner of that described in Example 195 using aniline Intermediate XX in step 2 and known or commercially available Grignard reagents in step 1. [M+H]+ Observed: 463.2 (Example 196) 449.2 (Example 197). rhSYK activity=+++ for both compounds.

EXAMPLE 198

4-(5-{3-[(4-cyclopropylpyrimidin-2-yl)amino]-5-methyphenyl}-1,3-thiazol-2-yl)-1,4-diazepan-2-one

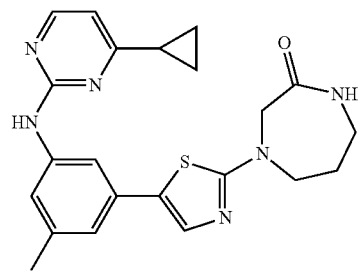 [SMILES: Cc1cc(Nc2nccc(C3CC3)n2)cc(-c2cnc(N3CCCNC(=O)C3)s2)c1]

Step 1:

2,4-Dichloropyrimidine (15 g, 101 mmol), cyclopropylboronic acid (8.65 g, 101 mmol), PdCl$_2$(dppf)-CH$_2$Cl$_2$ adduct (8.22 g, 10.07 mmol), and potassium phosphate (53.4 g, 252 mmol) were combined in a 1 L flask. THF (503 mL) was added and the suspension was heated to reflux with stirring overnight. The reaction was then cooled to room temperature, concentrated to ~100 mL under reduced pressure, extracted with ethyl acetate, washed with sat NaHCO$_3$, brine, dried over anhydrous sodium sulfate, filtered and concentrated under reduced pressure. The residue was purified by column chromatography on silica gel eluting with EtOAc/Hexanes to give 2-chloro-4-cyclopropylpyrimidine (10.124 g, 58.3 mmol, 58% yield) as an 89:11 mixture with EtOAc.

Step 2:

In an oven-dried vial was added 4-[5-(3-amino-5-methylphenyl)-1,3-thiazol-2-yl]-1,4-diazepan-2-one (Intermediate XX, 77 mg, 0.26 mmol), 2-chloro-4-cyclopropylpyrimidine (44 mg, 0.26 mmol), potassium carbonate (70 mg, 0.51 mmol), XPhos (61 mg, 0.13 mmol), and Pd$_2$(dba)$_3$ (23 mg, 0.025 mmol). The tube was evacuated and backfilled with argon 3×. Degassed t-amyl alcohol (0.85 ml) was added, and the tube was sealed and heated to 90° C. for 15 h. The mixture was then cooled to room temperature and purified by Combiflash (0-70% ethyl acetate/hexanes followed by 0-20% methanol/dichloromethane) to provide 77 mg (0.18 mmol, 72%) of 4-(5-{3-[(4-cyclopropylpyrimidin-2-yl)amino]-5-methylphenyl}-1,3-thiazol-2-yl)-1,4-diazepan-2-one as a yellow foam. MS APCI: [M+H]$^+$ m/z 421.2. $^1$H NMR (500 MHz, CDCl$_3$) δ 8.16 (d, J=5.6 Hz, 1H), 7.75 (s, 1H), 7.44 (s, 2H), 7.13 (s, 1H), 6.91 (s, 1H), 6.65 (d, J=5.5 Hz, 1H), 6.00 (s, 1H), 4.27 (d, J=13.9 Hz, 2H), 3.98-3.79 (m, 2H), 3.38 (dd, J=5.6 Hz, 11.2 Hz, 2H), 2.33 (s, 3H), 2.04 (d, J=4.0 Hz, 3H), 1.26 (t, J=7.3 Hz, 2H), 1.11 (dd, J=3.2 Hz, 8.3 Hz, 2H). rhSyk=+++.

EXAMPLE 199

4-(5-{3-[(4-ethenylpyrimidin-2-yl)amino]-5-methylphenyl}-1,3-thiazol-2-yl)-1,4-diazepan-2-one

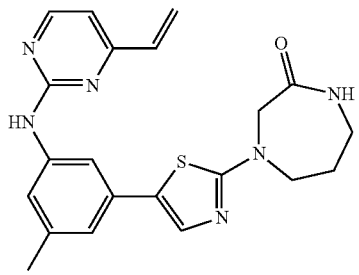 [SMILES: C=Cc1ccnc(Nc2cc(C)cc(-c3cnc(N4CCCNC(=O)C4)s3)c2)n1]

Step 1:

A mixture of 2,4-dichloropyrimidine (4.4 g, 29.5 mmol), potassium vinyltrifluoroborate (4.58 g, 32.5 mmol), PdCl$_2$(dppf)-CH$_2$Cl$_2$ (1.21 g, 1.48 mmol) and triethylamine (4.12 mL, 29.5 mmol) in nPrOH (148 mL) was purged with nitrogen for 15 min, heated to 100° C. for 5 h, and cooled to room temperature. The mixture was treated with water and extracted with EtOAc (×3). The combined organics were washed with brine, dried (sodium sulfate), concentrated, and purified by flash chromotography to afford 2-chloro-4-ethenylpyrimidine as a colorless oil. $^1$H NMR (500 MHz, CDCl$_3$) δ 8.56 (d, J=5.1, 1H), 7.21 (d, J=5.1, 1H), 6.70 (dd, J=10.6, 17.4, 1H), 6.57-6.51 (m, 1H), 5.79 (dd, J=0.8, 10.6, 1H).

Step 2:

2-Chloro-4-ethenylpyrimidine (250 mg, 1.78 mmol), 4-[5-(3-amino-5-methylphenyl)-1,3-thiazol-2-yl]-1,4-diazepan-2-one (Intermediate XX, 538 mg, 1.78 mmol), potassium carbonate (490 mg, 3.56 mmol), Pd$_2$(dba)$_3$ (163 mg, 0.18 mmol), and XPhos (420 mg, 0.89 mmol) were added to an oven-dried vessel which was purged and flushed with argon. t-Amyl alcohol (5 ml) was added and the reaction mixture was heated at 90° C. for 18 h. The mixture was then cooled to room temperature, diluted with water and brine and extracted with ethyl acetate (3×). The organic layers were dried over magnesium sulfate and concentrated under reduced pressure. The residual orange oil was purified via silica gel column chromatography (0-10% methanol/dichloromethane) to provide 188 mg of 4-(5-{3-[(4-ethenylpyrimidin-2-yl)amino]-5-methylphenyl}-1,3-thiazol-2-yl)-1,4-diazepan-2-one as a yellow-orange solid. MS APCI: [M+H]$^+$ m/z 407.1. $^1$H NMR (500 MHz, CDCl$_3$) δ 8.37 (d, 1H, J=4.9 Hz), 7.77 (s, 1H), 7.50 (s, 1H), 7.42 (s, 1H), 7.24 (s, 1H), 6.89 (s, 1H), 6.68 (d, 1H, J=5.2 Hz), 6.67-6.46 (m, 2H), 5.65 (m, 1H, J=9.1 Hz), 4.26 (m, 2H), 3.85 (m, 2H), 3.32 (m, 2H), 2.33 (s, 3H), 1.99 (m, 2H). rhSyk=+++.

EXAMPLE 200

4-(5-{3-[(5-chloropyrimidin-2-yl)amino]-5-methylphenyl}-1,3-thiazol-2-yl)-1,4-diazepan-2-one

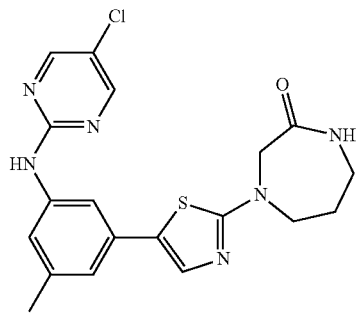 [SMILES: Cc1cc(Nc2ncc(Cl)cn2)cc(-c2cnc(N3CCCNC(=O)C3)s2)c1]

A sealed tube was charged with a stir bar, 4-[5-(3-amino-5-methylphenyl)-1,3-thiazol-2-yl]-1,4-diazepan-2-one (100 mg, 0.331 mmol), 2,5-dichloropyrimidine (49.3 mg, 0.331 mmol), potassium carbonate (91 mg, 0.661 mmol), Pd$_2$ dba$_3$ (30.3 mg, 0.033 mmol), and XPhos (79 mg, 0.165 mmol). The tube was evacuated and backfilled with argon three times. Fully degassed t-amyl alcohol (1.1 ml) was added, the tube was sealed and heated at 90° C. for overnight. The slurry was then cooled to room temperature, diluted with methanol, absorbed onto 2 g of silica, and purified via silica gel chromatography (0-20% methanol in ethyl acetate) to afford 4-(5-{3-[(5-chloropyrimidin-2-yl)amino]-5-methylphenyl}-1,3-thiazol-2-yl)-1,4-diazepan-2-one (66 mg, 0.159 mmol, 48.1% yield) as a bright yellow solid. MS APCI: [M+H]$^+$ m/z 415.1. $^1$H NMR (500 MHz, DMSO) δ 9.80 (s, 1H), 8.55 (s, 2H), 7.60 (s, 2H), 7.46 (s, 1H), 7.41 (s, 1H), 6.93 (s, 1H), 4.16 (m, 2H), 3.78 (m, 2H), 3.20 (m, 2H), 2.26 (s, 3H), 1.78 (m, 2H). rhSyk=+++.

The following examples were prepared in an analogous manner of that described in Example 200.

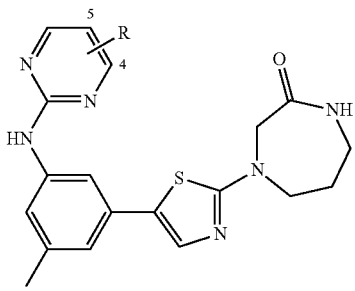

| Example | R | rhSYK Activity | [M + H]+ Obs'd | Form(s) |
|---|---|---|---|---|
| 201 | 5-F | +++ | 399.1 | Free Base |
| 202 | 5-cPr | +++ | 421.2 | Free Base |
| 203 | 5-Me | +++ | 395.1 | Free Base |
| 204 | 4-CN | +++ | 406.1 | Free Base |
| 205 | 4-OMe | +++ | 411.1 | Free Base |
| 206 | 4-iPr | +++ | 423.2 | Free Base |
| 207 | 4-Et | +++ | 409.2 | Free Base |
| 208 | 4-OCH$_2$Ph | +++ | 487.1 | Free Base |
| 209 | H | +++ | 380.8 | Free Base |

EXAMPLE 210

4-(5-{3-[(5-chloro-4-methoxypyrimidin-2-yl)amino]-5-methylphenyl}-1,3-thiazol-2-yl)-1,4-diazepan-2-one

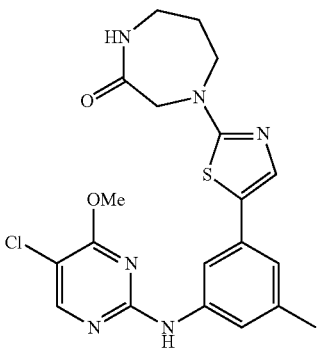 [SMILES: COc1nc(Nc2cc(C)cc(-c3cnc(N4CCCNC(=O)C4)s3)c2)ncc1Cl]

Step 1:
Sodium methoxide (295 mg, 5.45 mmol) was taken up in methanol (13.6 ml) and 2,4,5-trichloropyrimidine (500 mg, 2.73 mmol) was added. The mixture was stirred at room temperature overnight. The resulting mixture was concentrated under reduced pressure. The resulting residue was diluted with diethyl ether, washed with 1:1 water:saturated aqueous ammonium chloride. The organic layer was dried over magnesium sulfate, filtered, and concentrated under reduced pressure. Purification by Combiflash (0-10% diethyl ether/hexanes) afforded 280 mg (1.56 mmol, 57%) of 2,5-dichloro-4-methoxypyrimidine as a white solid.

Step 2:
A sealed tube was charged with a stir bar, 4-[5-(3-amino-5-methylphenyl)-1,3-thiazol-2-yl]-1,4-diazepan-2-one (Intermediate XX, 75 mg, 0.248 mmol), 2,5-dichloro-4-methoxypyrimidine (44 mg, 0.248 mmol), potassium carbonate (69 mg, 0.496 mmol), Pd$_2$(dba)$_3$ (23 mg, 0.025 mmol), and XPhos (59 mg, 0.124 mmol). The tube was evacuated and backfilled with argon three times. Fully degassed t-amyl alcohol (0.83 ml) was added and the tube was sealed and heated at 90° C. for overnight. The resulting slurry was diluted with methanol, absorbed onto 1.5 g of silica, and purified via silica gel chromatography (0-20% methanol in ethyl acetate) to afford 44 mg (1.0 mmol, 40% yield) of 4-(5-{3-[(5-chloro-4-methoxypyrimidin-2-yl)amino]-5-methylphenyl}-1,3-thiazol-2-yl)-1,4-diazepan-2-one as a light yellow solid. MS APCI: [M+H]m/z 445.1. $^1$H NMR (500 MHz, dmso) δ 9.72 (s, 1H), 8.30 (s, 1H), 7.77 (s, 1H), 7.59 (t, J=5.0 Hz, 1H), 7.48 (s, 1H), 7.30 (s, 1H), 6.95 (s, 1H), 4.15 (s, 2H), 4.05 (s, 3H), 3.78 (m, 2H), 3.21 (m, 2H), 2.26 (s, 3H), 1.77 (m, 2H). rhSyk=+++

EXAMPLE 211

4-(5-{3-[(5-Chloro-4-methylpyrimidin-2-yl)amino]-5-methylphenyl}-1,3-thiazol-2-yl)-1,4-diazepan-2-one

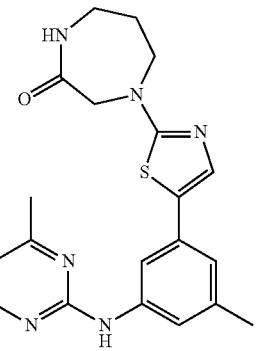

Step 1:
2,4,5-Trichloropyrimidine (250 mg, 1.36 mmol) and ferric acetylacetonate (24 mg, 0.07 mmol) were taken up in tetrahydrofuran (2.7 ml) and the reaction was cooled to −78° C. Methylmagnesium bromide (0.45 ml of 3 M in THF, 1.36 mmol) was added dropwise and the mixture was stirred at −78° C. for one hour. The mixture was quenched with aqueous ammonium chloride and extracted with ethyl acetate. The combined organic fractions were dried over magnesium sulfate, filtered, and the solvent was evaporated under reduced pressure. The resulting residue was purified by Combiflash (0-10% diethylether in hexanes) to provide 2,5-dichloro-4-methylpyrimidine (99 mg, 0.61 mmol, 45%) as a white solid. MS APCI: [M+H]$^+$ m/z 163.0.

Step 2:
A sealed tube was charged with a stir bar, 4-[5-(3-amino-5-methylphenyl)-1,3-thiazol-2-yl]-1,4-diazepan-2-one (Intermediate XX, 75 mg, 0.25 mmol), 2,5-dichloro-4-methylpyrimidine (40 mg, 0.25 mmol), potassium carbonate (69 mg, 0.50 mmol), Pd$_2$(dba)$_3$ (23 mg, 0.025 mmol), and XPhos (59 mg, 0.124 mmol). The tube was evacuated and backfilled with argon three times. Fully degassed t-amyl alcohol (0.83 ml) was added and the tube was sealed and heated at 90° C. for overnight. The resulting slurry was diluted with methanol, absorbed onto 1.5 g of silica, and purified via silica gel chromatography (0-20% methanol in ethyl acetate) to afford 54 mg (0.126 mmol, 51% yield) of 4-(5-{3-[(5-Chloro-4-methylpyrimidin-2-yl)amino]-5-methylphenyl}-1,3-thiazol-2-yl)-1,4-diazepan-2-one as a yellow solid. MS APCI: [M+H]$^+$ m/z 429.1. $^1$H NMR (500 MHz, dmso) δ 9.73 (s, 1H), 8.42 (s, 1H), 7.74 (s, 1H), 7.59 (t, J=5.0 Hz, 1H), 7.46 (s, 1H), 7.37 (s, 1H), 6.91 (s, 1H), 4.16 (s, 2H), 3.78 (m, 2H), 3.21 (m, 2H), 2.44 (s, 3H), 2.26 (s, 3H), 1.78 (m, 2H). rhSyk=+++

EXAMPLE 212

4-{5-[3-methyl-5-({4-[(3R)-pyrrolidin-3-yloxy]pyrimidin-2-yl}amino)phenyl]-1,3-thiazol-2-yl}-1,4-diazepan-2-one

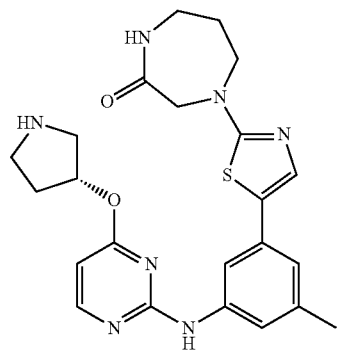 [SMILES: Cc1cc(Nc2nccc(O[C@@H]3CCNC3)n2)cc(-c2cnc(N3CCCNC(=O)C3)s2)c1]

Step 1:
2,4-Dichloropyrimidine (3.95 g, 26.5 mmol), tert-butyl (3R)-3-hydroxypyrrolidine-1-carboxylate (4.14 g, 22.11 mmol), and cesium carbonate (18 g, 55.3 mmol) were taken up in DMSO (44 ml). The reaction mixture was heated to 140° C. for 40 min, cooled to room temperature, and diluted with ethyl acetate. The mixture was washed with water (×2) and brine. The combined organics were dried over sodium sulfate, concentrated, and purified by Combiflash (ethyl acetate/hexanes) to afford tert-butyl (3R)-3-[(2-chloropyrimidin-4-yl)oxy]pyrrolidine-1-carboxylate.

Step 2:
To a stirred solution of the 4-[5-(3-amino-5-methylphenyl)-1,3-thiazol-2-yl]-1,4-diazepan-2-one (Intermediate XX, 165 mg, 0.55 mmol) and tert-butyl (3R)-3-[(2-chloropyrimidin-4-yl)oxy]pyrrolidine-1-carboxylate (164 mg, 0.55 mmol) in dioxane (2.7 ml) was added AcOH (66 µl, 1.15 mmol). The mixture was heated to 120° C. for 5 h, treated with additional portion of AcOH (66 µl, 1.15 mmol), and left to stir overnight. Additional AcOH (66 µl, 1.15 mmol) was then added and the resultant mixture was left to stir overnight. The mixture was then cooled to room temperature, diluted with saturated sodium bicarbonate solution, and extracted with ethyl acetate (×3). The combined organics were washed with brine, dried over sodium sulfate, concentrated, and purified by Combiflash. (ethyl acetate/hexanes) to afford 80 mg (0.14 mmol, 26% yield) of tert-butyl (3R)-3-{[2-({3-methyl-5-[2-(3-oxo-1,4-diazepan-1-yl)-1,3-thiazol-5-yl]phenyl}amino)pyrimidin-4-yl]oxy}pyrrolidine-1-carboxylate.

Step 3:
tert-Butyl (3R)-3-{[2-({3-methyl-5-[2-(3-oxo-1,4-diazepan-1-yl)-1,3-thiazol-5-yl]-phenyl}amino)pyrimidin-4-yl]oxy}pyrrolidine-1-carboxylate (80 mg, 0.14 mmol) was taken up in dichloromethane (1 mL). The mixture was treated with trifluoroacetic acid (0.2 mL, 2.6 mmol) and left to stir for 1 hour. The reaction was neutralized with saturated aqueous sodium bicarbonate, and extracted with ethyl acetate (×3). The combined organics were washed with brine, dried over sodium sulfate, concentrated, and purified by Combiflash (methanol/dichloromethane) to provide 4-{5-[3-methyl-5-({4-[(3R)-pyrrolidin-3-yloxy]-pyrimidin-2-yl}amino)phenyl]-1,3-thiazol-2-yl}-1,4-diazepan-2-one. MS APCI: [M+H]⁺ m/z 466.1. ¹H NMR (500 MHz, DMSO-d6) δ 9.53 (s, 1H), 8.22 (d, J=5.6, 1H), 7.63 (m, 2H), 7.49 (s, 1H), 7.38 (s, 1H), 6.96 (s, 1H), 6.25 (d, J=5.6, 1H), 5.56 (s, 1H), 4.16 (s, 2H), 4.10 (s, 1H), 3.80 (s, 2H), 3.44-3.05 (m, 5H), 2.27 (s, 3H), 2.21 (m, 1H), 2.06 (m, 1H), 1.77 (m, 2H). rhSyk=+++

The following examples were prepared in an analogous manner of that described in Example 212.

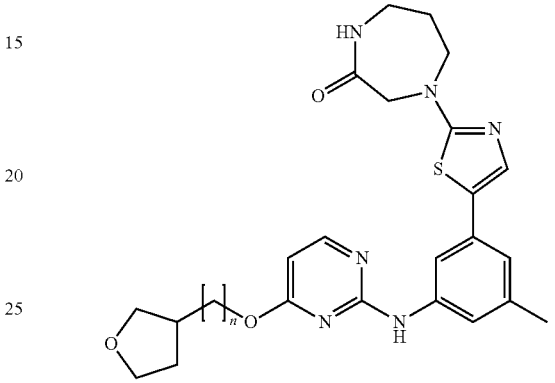

| Example | n | rhSYK Activity | [M + H]+ Obs'd | Form(s) |
|---|---|---|---|---|
| 213 | 1 | +++ | 480.8 | Free Base |
| 214 | 0 | +++ | 466.8 | Free Base |

EXAMPLE 215

4-[5-(3-methyl-5-{[4-(piperidin-4-yloxy)pyrimidin-2-yl]amino}phenyl)-1,3-thiazol-2-yl]-1,4-diazepan-2-one

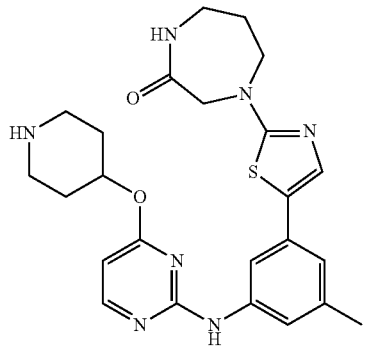 [SMILES: Cc1cc(Nc2nccc(OC3CCNCC3)n2)cc(-c2cnc(N3CCCNC(=O)C3)s2)c1]

Step 1:
To tert-butyl 4-hydroxypiperidine-1-carboxylate (389 mg, 1.933 mmol) and 2,4-dichloropyrimidine (240 mg, 1.611 mmol) in N,N-dimethylformamide (6.4 mL) was added cesium carbonate (1050 mg, 3.22 mmol) and the mixture was heated at 80° C. for 1 hour and then to 70° C. overnight. The reaction was then cooled to ambient temperature, diluted with ethyl acetate, and washed with water (3×) and brine (1×). The organic layer was dried, filtered, and concentrated under reduced pressure. The residue was purified by column chromatography on silica gel (0-50% ethyl acetate/hexanes) to provide 410 mg (1.3 mmol, 81%) of tert-butyl 4-[(2-chloropyrimidin-4-yl)oxy]piperidine-1-carboxylate as white solid. MS APCI: [M+H]+ m/z 314.2.

Step 2:

To 4-[5-(3-amino-5-methylphenyl)-1,3-thiazol-2-yl]-1,4-diazepan-2-one (Intermediate XX, 59 mg, 0.19 mmol) in a scintillation vial was added dioxane (0.97 ml), cesium carbonate (126 mg, 0.39 mmol), and tert-butyl 4-[(2-chloropyrimidin-4-yl)oxy]piperidine-1-carboxylate (67 mg, 0.21 mmol). The system was purged and flushed with argon (3×) before adding XantPhos (17 mg, 0.029 mmol) and palladium (II) acetate (5 mg, 0.021 mmol). The system was purged and flushed with argon (3×) before sealing the system and heating to 100° C. overnight. The reaction was cooled to room temperature, filtered through celite and diluted with water. The organic layer was separated, dried over sodium sulfate, and concentrated under reduced pressure. Purification via reverse phase chromatography (10-80% acetonitrile in water, linear gradient) provided tert-butyl 4-{[2-({3-methyl-5-[2-(3-oxo-1,4-diazepan-1-yl)-1,3-thiazol-5-yl]phenyl}amino)pyrimidin-4-yl]oxy}piperidine-1-carboxylate. This material was treated with 2 ml of 1:1 trifluoroacetic acid:dichloromethane solution for 1 hr. The reaction was concentrated to dryness and purified by reverse phase chromatography (5-60% acetonitrile in water) to provide 16 mg (0.027 mmol, 14% yield) of 4-[5-(3-methyl-5-{[4-(piperidin-4-yloxy)pyrimidin-2-yl]amino}phenyl)-1,3-thiazol-2-yl]-1,4-diazepan-2-one as the TFA salt. MS APCI: [M+H]+ m/z 480.2. 1H NMR (500 MHz, dmso) δ 9.70-9.49 (m, 1H), 8.72-8.37 (m, 2H), 8.34-8.08 (m, 1H), 7.70-7.61 (m, 1H), 7.61-7.54 (m, 1H), 7.54-7.47 (m, 1H), 7.41-7.33 (m, 1H), 6.96-6.91 (m, 1H), 6.41-6.13 (m, 1H), 5.42-5.15 (m, 1H), 4.17 (s, 2H), 3.96-3.65 (m, 2H), 3.36-3.14 (m, 2H), 3.14-2.93 (m, 2H), 2.27 (s, 3H), 2.22-2.07 (m, 2H), 2.01-1.84 (m, 1H), 1.84-1.63 (m, 2H), 1.21-1.01 (m, 2H). TFA salt proton was visible. rhSyk=+++.

EXAMPLE 216

4-[5-(3-{[5-fluoro-4-(tetrahydrofuran-3-yloxy)pyrimidin-2-yl]amino}-5-methylphenyl)-1,3-thiazol-2-yl]-1,4-diazepan-2-one

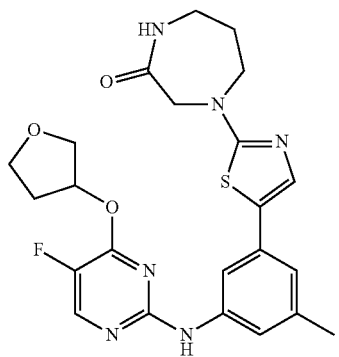 [SMILES: Cc1cc(Nc2ncc(F)c(OC3CCOC3)n2)cc(-c2cnc(N3CCCNC(=O)C3)s2)c1]

Step 1:

A flask was charged with a solution of 2,4-dichloro-5-fluoropyrimidine (1.0 g, 5.99 mmol) in N,N'-dimethylformamide (20 ml). Tetrahydrofuran-3-ol (0.63 m, 7.19 mmol) and cesium carbonate (3.32 g, 10.18 mmol) were added and the resulting mixture was heated to 80° C. overnight. Upon completion, the mixture was diluted with ethyl acetate (20 mL) and washed with 1:1 water:brine (3×40 mL). The organic extracts were dried over sodium sulfate, filtered, and concentrated under reduced pressure. Purification by CombiFlash (ethyl acetate/hexanes) provided 374 mg (1.7 mmol, 29%) of 2-chloro-5-fluoro-4-(tetrahydrofuran-3-yloxy)pyrimidine. MS APCI: [M+H]+ m/z 219.0.

Step 2:

2-Chloro-5-fluoro-4-(tetrahydrofuran-3-yloxy)pyrimidine (70 mg, 0.32 mol), 4-[5-(3-amino-5-methylphenyl)-1,3-thiazol-2-yl]-1,4-diazepan-2-one (Intermediate XX, 97 mg, 0.32 mmol), Pd2(dba)3 (29 mg, 0.032 mmol), XPhos (76 mg, 0.16 mmol) and potassium carbonate (89 mg, 0.64 mmol) were added to a flask. The flask was purged and flushed with argon (3×). Degassed tert-amyl alcohol (1.1 ml) was added, the reaction mixture was purged with nitrogen for 5 min, and then heated to 90° C. overnight. The mixture was cooled to room temperature, diluted with ethyl acetate, treated with water, and extracted with ethyl acetate (×3). The combined organics were washed with brine, dried over sodium sulfate, concentrated, and purified by Combiflash (methanol/dichloromethane eluant) to provide 109 mg (0.23 mmol, 70% yield) of 4-[5-(3-{[5-fluoro-4-(tetrahydrofuran-3-yloxy)pyrimidin-2-yl]amino}-5-methylphenyl)-1,3-thiazol-2-yl]-1,4-diazepan-2-one. MS APCI: [M+H]+ m/z 485.1. 1H NMR (500 MHz, DMSO-d6) δ 9.53 (s, 1H), 8.30 (d, J=2.9 Hz, 1H), 7.59 (t, J=4.8 Hz, 1H), 7.57 (s, 1H), 7.48 (s, 1H), 7.34 (s, 1H), 6.95 (s, 1H), 5.64 (t, J=4.9 Hz, 1H), 4.16 (s, 2H), 3.97-3.73 (m, 6H), 3.21 (m, 2H), 2.32 (m, 1H), 2.26 (s, 3H), 2.10 (m, 1H), 1.77 (s, 2H). rhSyk=++

EXAMPLE 217

4-[5-(3-{[4-(butylsulfanyl)pyrimidin-2-yl]amino}-5-methylphenyl)-1,3-thiazol-2-yl]-1,4-diazepan-2-one

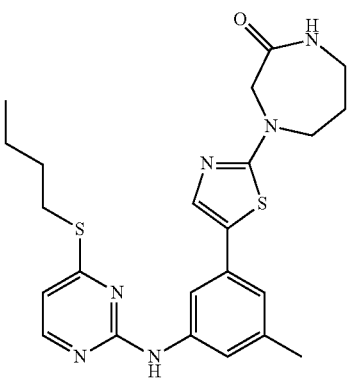 [SMILES: CCCCSc1ccnc(Nc2cc(C)cc(-c3cnc(N4CCCNC(=O)C4)s3)c2)n1]

Step 1:

To an oven-dried vial was added 2-chloro-4-methylthiopyrimidine (0.885 g, 4.13 mmol), intermediate XX (1.25 g, 4.13 mmol), tris-(dibenzylideneacetone)dipalladium(0) (0.379 g, 0.413 mmol), 2-dicyclohexylphosphino-2',4',6'-triisopropylbiphenyl (0.985 g, 2.067 mmol), and potassium carbonate (1.143 g, 8.27 mmol). The vial was evacuated and backfilled with Ar (g) 3×. Degassed t-amyl alcohol (13.78 mL) was added, and the mixture was sealed and heated to 90° C. overnight. After cooling to room temperature, diluted with methanol, added 10 g silica, and concentrated in vacuo. Purified by CombiFlash (100:0 to 0:20 dichloromethane:methanol) to afford 4-[5-(3-methyl-5-{[4-(methylsulfanyl)pyrimidin-2-yl]amino}phenyl)-1,3-thiazol-2-yl]-1,4-diazepan-2- one (0.990 g, 2.321 mmol, 56% yield) as a yellow solid. MS APCI: [M+H]+ m/z 427.1. rhSYK activity=+++.

Step 2:

To 4-[5-(3-methyl-5-{[4-(methylsulfanyl)pyrimidin-2-yl]amino}phenyl)-1,3-thiazol-2-yl]-1,4-diazepan-2-one (0.94 g, 2.204 mmol) stirring in dichloromethane (11 mL) at room temperature was added 3-chloroperbenzoic acid (1.587 g, 7.08 mmol). Stirred for 4 hr. at room temperature, diluted with 10% Na$_2$S$_2$O$_3$ (aq.), and washed with sat. NaHCO$_3$ (aq.) and brine. The organic extracts were dried (Na$_2$SO$_4$), filtered, and concentrated in vacuo. Purified by CombiFlash (100:0 to 0:20 dichloromethane:methanol) to afford impure 4-[5-(3-methyl-5-{[4-(methylsulfonyl)-2-pyrimidinyl]amino}phenyl)-1,3-thiazol-2-yl]-1,4-diazepan-2-one (0.188 g, 0.411 mmol, 18.6% yield) as an orange solid (contaminated with starting material). MS APCI: [M+H]+ m/z 459.1

Step 3:

Sodium bis(trimethylsilyl)amide (164 μL, 1.0 M, 0.164 mmol) was added to a solution of 1-butanethiol (28.1 μL, 0.262 mmol) stirring in DMF (327 μL) at room temperature in an oven-dried vial. Stirred for 15 minutes, then added 4-[5-(3-methyl-5-{[4-(methylsulfonyl)-2-pyrimidinyl]amino}phenyl)-1,3-thiazol-2-yl]-1,4-diazepan-2-one (30 mg, 0.065 mmol). Stirred at room temperature for 30 minutes, diluted with ethyl acetate (10 mL), and washed with 1:1 water:brine (10 mL). The organic extracts were dried (Na$_2$SO$_4$), filtered, and concentrated in vacuo. Purified by CombiFlash (100:0 to 0:20 dichloromethane:methanol) to afford 4-[5-(3-{[4-(butylsulfanyl)pyrimidin-2-yl]amino}-5-methylphenyl)-1,3-thiazol-2-yl]-1,4-diazepan-2-one (14.6 mg, 0.031 mmol, 48% yield) as a white solid. MS APCI: [M+H]+ m/z 469.2. $^1$H NMR (500 MHz, DMSO) δ 9.52 (s, 1H), 8.13 (d, J=5.3 Hz, 1H), 7.60 (dd, J=4.9 Hz, 10.3 Hz, 2H), 7.45 (s, 1H), 7.43 (s, 1H), 6.92 (s, 1H), 6.72 (d, J=5.3 Hz, 1H), 4.16 (s, 2H), 3.84-3.73 (m, 2H), 3.25-3.12 (m, 4H), 2.26 (s, 3H), 1.78 (m, 2H), 1.59 (m, 2H), 1.35 (dd, J=7.4 Hz, 14.9 Hz, 2H), 0.83 (t, J=7.4 Hz, 3H).

rhSYK activity=+++.

The following examples were prepared in an analogous manner of that described in Example 217.

| Ex. | X | R | rhSYK Activity | [M + H]+ Obs'd | Form(s) |
|---|---|---|---|---|---|
| 218 | O | —CH$_2$CH$_2$OH | +++ | 441.1 | Free Base |
| 219 | S | iPr | +++ | 455.1 | Free Base |
| 220 | S | nPr | +++ | 455.1 | Free Base |
| 221 | S | Et | +++ | 441.1 | Free Base |

EXAMPLE 222

4-{5-[3-({4-[(2-hydroxyethyl)sulfanyl]pyrimidin-2-yl}amino)-5-methylphenyl]-1,3-thiazol-2-yl}-1,4-diazepan-2-one

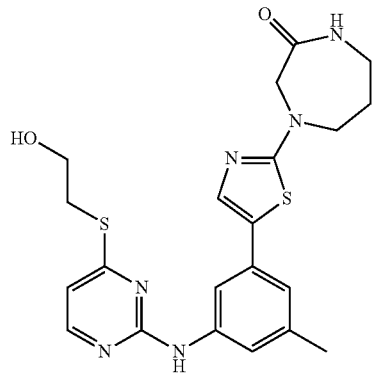 [SMILES: Cc1cc(Nc2nccc(SCCO)n2)cc(-c2cnc(N3CCCNC(=O)C3)s2)c1]

Potassium carbonate (9.95 mg, 0.072 mmol) was added to a solution of 2-mercaptoethanol (18.34 μL, 0.262 mmol) stirring in DMF (327 μL) at room temperature in an oven-dried vial. Stirred for 15 minutes, then added 4-[5-(3-methyl-5-{[4-(methylsulfonyl)-2-pyrimidinyl]amino}phenyl)-1,3-thiazol-2-yl]-1,4-diazepan-2-one (30 mg, 0.065 mmol). Stirred at room temperature for 30 minutes, diluted with ethyl acetate (10 mL), and washed with 1:1 water:brine (10 mL). The organic extracts were dried (Na$_2$SO$_4$), filtered, and concentrated in vacuo. Purified by CombiFlash (100:0 to 0:20 dichloromethane:methanol) to afford 4-{5-[3-({4-[(2-hydroxyethyl)sulfanyl]pyrimidin-2-yl}amino)-5-methylphenyl]-1,3-thiazol-2-yl}-1,4-diazepan-2-one (8.4 mg, 0.018 mmol, 28.1% yield) as a yellow solid. MS APCI: [M+H]+ m/z 457.1. $^1$H NMR (500 MHz, DMSO) δ 9.52 (s, 1H), 8.14 (d, J=5.3 Hz, 1H), 7.58 (d, J=12.2 Hz, 2H), 7.47 (d, J=8.4 Hz, 2H), 6.92 (s, 1H), 6.75 (d, J=5.4 Hz, 1H), 4.97 (t, J=5.4 Hz, 1H), 4.16 (s, 2H), 3.79 (s, 2H), 3.64 (dd, J=6.3 Hz, 11.9 Hz, 2H), 3.29 (s, 1H), 3.21 (s, 2H), 3.15 (d, J=5.2 Hz, 1H), 2.27 (s, 3H), 1.78 (s, 2H). rhSYK activity=+++.

EXAMPLE 223

4-[5-(3-methyl-5-{[4-(methylsulfinyl)pyrimidin-2-yl]amino}phenyl)-1,3-thiazol-2-yl]-1,4-diazepan-2-one

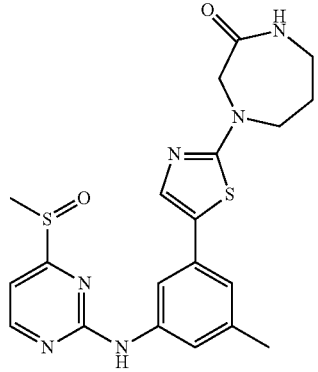 [SMILES: Cc1cc(Nc2nccc(S(C)=O)n2)cc(-c2cnc(N3CCCNC(=O)C3)s2)c1]

To 4-[5-(3-methyl-5-{[4-(methylsulfanyl)pyrimidin-2-yl]amino}phenyl)-1,3-thiazol-2-yl]-1,4-diazepan-2-one (50 mg, 0.117 mmol) stirring in dichloromethane (586 μL) at room temperature was added 3-chloroperbenzoic acid (27.6 mg, 0.123 mmol). Stirred for 3 hr. at room temperature, diluted with 10% Na₂S₂O₃ (aq.), and washed with sat. NaHCO₃ (aq.) and brine. The organic extracts were dried (Na₂SO₄), filtered, and concentrated in vacuo. Purified by reverse phase preparative HPLC (0:100 to 95:5 acetonitrile: water: 0.1% v/v trifluoroacetic acid modifier) to afford 4-[5-(3-methyl-5-{[4-(methylsulfinyl)pyrimidin-2-yl]amino}phenyl)-1,3-thiazol-2-yl]-1,4-diazepan-2-one (3.3 mg, 7.5 µmol, 6.36% yield) as a yellow solid. MS APCI: [M+H]⁺ m/z 443.1. ¹H NMR (500 MHz, CDCl₃) δ 8.67 (d, J=4.9 Hz, 1H), 7.68 (s, 1H), 7.48 (s, 1H), 7.44 (d, J=4.9 Hz, 1H), 7.34-7.29 (m, 1H), 7.19 (s, 1H), 6.96 (s, 1H), 5.93-5.85 (m, 1H), 4.28 (s, 2H), 3.46 (s, 2H), 2.93 (s, 2H), 2.37 (s, 3H), 2.16-2.01 (m, 2H), 1.25 (s, 3H). rhSYK activity=+++.

EXAMPLE 224

N-{3-methyl-5-[2-(morpholin-4-yl)-1,3-thiazol-4-yl]phenyl}-4-(trifluoromethyl)pyrimidin-2-amine

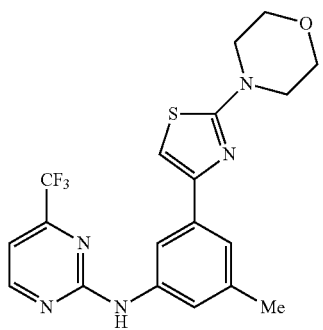 [SMILES: Cc1cc(Nc2nccc(C(F)(F)F)n2)cc(-c2csc(N3CCOCC3)n2)c1]

N-[3-Methyl-5-(4,4,5,5-tetramethyl-1,3,2-dioxaborolan-2-yl)phenyl]-4-(trifluoromethyl)-pyrimidin-2-amine (100 mg, 0.264 mmol), sodium carbonate (33.5 mg, 0.316 mmol), 4-(4-bromo-1,3-thiazol-2-yl)morpholine (79 mg, 0.316 mmol), 2-(dicyclohexylphosphino)-3,6-dimethoxy-2'-4'-6'-tri-1-propyl-1,1'-biphenyl (7.1 mg, 0.01 mmol) and chloro[2-(dicyclohexylphosphino)-3,6-dimethoxy-2'-4'-6'-tri-1-propyl-1,1'-biphenyl][2-(2-aminoethyl)phenyl]palladium(II) (10.5 mg, 0.013 mmol) were placed in a 4-mL vial. The vial was evacuated and back-filled with nitrogen (3×). 1,4-Dioxane (2 mL) and water (0.4 mL) were added and the reaction mixture heated to 80° C. for 16 hours. The reaction mixture was cooled to room temperature and filtered over celite with methanol (~20 mL). Solvent evaporation gave a crude residue which was purified by preparative HPLC Reverse phase (C-18), eluting with acetonitrile/water+0.1% trifluoroacetic acid (eluting with 40-100% MeCN), to give 20 mg (0.037 mmol, 14.2% yield) of N-{3-methyl-5-[2-(morpholin-4-yl)-1,3-thiazol-4-yl]phenyl}-4-(trifluoromethyl)pyrimidin-2-amine trifluoroacetate salt as a yellow solid. MS APCI [M+H]⁺ m/z 422.1. ¹H NMR (500 MHz, d6-DMSO): 2.30 (s, 3H), 3.43 (t, J=4.9 Hz, 4H), 3.72 (t, J=4.9 Hz, 4H), 7.14 (s, 1H), 7.23 (d, J=4.9 Hz, 1H), 7.33 (s, 1H), 7.40 (s, 1H), 8.17 (s, 1H), 8.79 (d, J=4.9 Hz, 1H).

EXAMPLE 225

1-[4-(3-methyl-5-{[4-(trifluoromethyl)pyrimidin-2-yl]amino}phenyl)-1,3-thiazol-2-yl]piperidin-4-ol

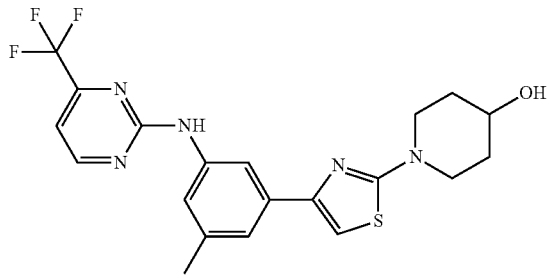 [SMILES: Cc1cc(Nc2nccc(C(F)(F)F)n2)cc(-c2csc(N3CCC(O)CC3)n2)c1]

The title compound, as the TFA salt, was prepared in an analogous manner of that described in Example 224. [M+H]+ Observed: 436.1. rhSYK Activity: ++

EXAMPLE 226

4-[5-(3-methyl-5-{[4-(trifluoromethyl)pyrimidin-2-yl]amino}phenyl)-1,3-thiazol-2-yl]-1,4-diazepan-2-one

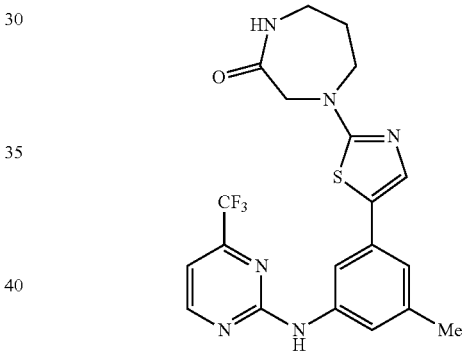

N-[3-Methyl-5-(4,4,5,5-tetramethyl-1,3,2-dioxaborolan-2-yl)phenyl]-4-(trifluoromethyl)-pyrimidin-2-amine (Intermediate IV, 35.4 g, 93 mmol) and 4-(5-bromo-1,3-thiazol-2-yl)-1,4-diazepan-2-one (21.5, 78 mmol) were combined in a 2 L RB flask follwed by DMF (473 mL) and aqueous Na₂CO₃ solution (1 M, 311 mL). The solution was sparged with N₂ for 15 minutes and then [Pd(Ph₃P)₄](3.6 g, 3.11 mmol) was added. The mixture was heated at 85° C. for 12-15 hours. The reaction was cooled to 0° C. and saturated NH₄Cl (500 mL) was added followed by EtOAc (2 L) and DCM (2 L). The aqueous layer was extracted with DCM (1 L) and the combined organic layer was washed with 10% aqueous LiCl solution (1 L) and then dried over Na₂SO₄. The organic layer was concentrated and slurried in MTBE (500 mL) and filtered. The solid was then dissolved in THF (870 mL), degassed and then treated with 300 wt % Silicycle Si-triamine resin at 40° C. for 1 hour. The suspension was then filtered, the residue washed with 40° C. THF (400 mL) and concentrated. A final slurrying in MTBE (200 mL) for 1.5 hours, filtration and drying gave 13.1 g of 4-[5-(3-methyl-5-{[4-(trifluoromethyl)pyrimidin-2-yl]amino}phenyl)-1,3-thiazol-2-yl]-1,4-diazepan-2-one (37%). MS APCI: [M+H]⁺ m/z 449.2. ¹H NMR (600 MHz, DMSO-d6): δ 10.14 (s, 1H), 8.79 (d, J=6.0 Hz, 1H); 7.77 (s, 1H), 7.57 (t, J=4.7 Hz, 1H); 7.44 (s, 1H); 7.34 (s, 1H); 7.23 (d, J=4.9 Hz, 1H); 6.9 (s, 1H), 4.19 (s, 2H); 3.76 (m, 2H); 3.19 (m, 2H); 2.26 (s, 3H), 1.76 (m, 2H). rhSyk=+++

EXAMPLE 227

4-(4-chloro-5-{3-[(4-methoxypyrimidin-2-yl)amino]-5-methylphenyl}-1,3-thiazol-2-yl)-1,4-diazepan-2-one

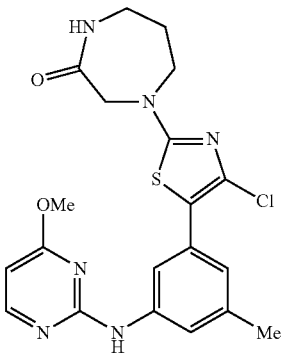 [SMILES: COc1ccnc(Nc2cc(C)cc(-c3sc(N4CCCNC(=O)C4)nc3Cl)c2)n1]

Step 1:
Combined 2,4-dichlorothiazole (405 mg, 2.63 mmol), 3-oxo-1,4-diazepan-1-ium trifluoroacetate (preparation described in Intermediate XX, 600 mg, 2.63 mmol), potassium phosphate tribasic (1395 mg, 6.57 mmol) and DMSO (22.00 ml) in a round bottomed flask, fitted with water-cooled condenser, balloon and septum. The mixture was heated to 150° C. for 7 hours with stirring. The dark solution was diluted with 100 mL 10% IPA/CHCl$_3$, 40 mL water, mL aq. NaHCO$_3$(sat.). The resulting suspension was extracted with 10% IPA/CHCl$_3$, and the organic layers were combined and washed successively with water and brine. The organic fractions were pooled and concentrated to dryness. The residue was then loaded directly onto silica gel and purified by preparative HPLC Normal phase, eluting with CH$_2$Cl$_2$/MeOH (0-30%). The 3rd peak was collected and concentrated to afford 4-(4-chloro-1,3-thiazol-2-yl)-1,4-diazepan-2-one (179 mg, 0.773 mmol, 29.4% yield) as a brown solid.
Step 2:
n-bromosuccinimide (80 mg, 0.449 mmol) was combined with a solution of 4-(4-chloro-1,3-thiazol-2-yl)-1,4-diazepan-2-one (100 mg, 0.432 mmol) in CHCl$_3$ (6 ml) and stirred at 23° C. for 8 minutes. The solution became dark was immediately diluted with ethyl acetate, and washed successively with aq. sodium thiosulfate (sat.), aq. NaHCO$_3$ (sat.) and brine. The organic fraction was dried (Na$_2$SO$_4$), filtered and concentrated to afford 4-(5-bromo-4-chloro-1,3-thiazol-2-yl)-1,4-diazepan-2-one (75 mg, 0.241 mmol, 55.9% yield) as a yellow oil of sufficient purity for subsequent transformations.
Step 3:
To a solution of 3-methyl-5-(4,4,5,5-tetramethyl-1,3,2-dioxaborolan-2-yl)aniline (preparation described in Intermediate XIX (1), 59 mg, 0.253 mmol), 4-(5-bromo-4-chloro-1,3-thiazol-2-yl)-1,4-diazepan-2-one (75 mg, 0.241 mmol), 1,1'-bis(diphenylphosphino)ferrocene-palladium(II)dichloride (35 mg, 0.048 mmol) in dioxane (0.600 mL) was added 2M aqueous sodium carbonate (0.240 mL, 0.480 mmol). The mixture was heated on a reaction block at 100° C. for 3 hours, and subsequently cooled to room temperature. The dark mixture was filtered through a celite plug, which was rinsed with 10% isopropanol in CHCl$_3$. The eluent was concentrated and purified by preparative HPLC Normal phase, eluting with CH$_2$Cl$_2$/MeOH (0-30%). The 3rd peak was collected and concentrated to give 4-[5-(3-amino-5-methylphenyl)-4-chloro-1,3-thiazol-2-yl]-1,4-diazepan-2-one (45 mg, 0.134 mmol, 29.1% yield) as a brown solid.
Step 4:
A sealed tube was charged with a stir bar, 4-[5-(3-amino-5-methylphenyl)-4-chloro-1,3-thiazol-2-yl]-1,4-diazepan-2-one (45 mg, 0.134 mmol), 2-chloro-4-methoxypyrimidine, (20 mg, 0.138 mmol), potassium carbonate (37 mg, 0.268 mmol), Pd$_2$(dba)$_3$ (13 mg, 0.013 mmol), and dicyclohexyl[2',4',6'-tri(propan-2-yl)biphenyl-2-yl]phosphane (X-Phos, 31.8 mg, 0.067 mmol). The tube was evacuated and backfilled with argon three times. Fully degassed t-amyl alcohol (450 µl) was added, the tube was sealed and heated at 80° C. for 16 h with stirring. The reaction mixture was then cooled and filtered through a celite plug, which was rinsed with 10% isopropanol in CHCl$_3$. The eluent was concentrated and purified by preparative HPLC Reverse phase (C-18), eluting with Acetonitrile/Water (30-100%), providing 4-(4-chloro-5-{3-[(4-methoxypyrimidin-2-yl)amino]-5-methylphenyl}-1,3-thiazol-2-yl)-1,4-diazepan-2-one (19 mg, 0.032 mmol, 29.1%) as a TFA salt. APCI: [M+H]$^+$ m/z 440.1. $^1$H NMR (500 MHz, dmso) δ9.65 (s, 1H), 8.19 (d, J=5.7, 1H), 7.90 (s, 1H), 7.66 (s, 1H), 7.50 (s, 1H), 6.98 (s, 1H), 6.29 (d, J=5.7 Hz, 1H), 4.15 (s, 2H), 3.93 (s, 3H), 3.76 (s, 2H), 3.23 (s, 2H), 2.28 (s, 3H), 1.77 (s, 2H). rhSYK activity=+++.

EXAMPLE 228

4-[4-chloro-5-(3-methyl-5-{[4-(trifluoromethyl)pyrimidin-2-yl]amino}phenyl)-1,3-thiazol-2-yl]-1,4-diazepan-2-one

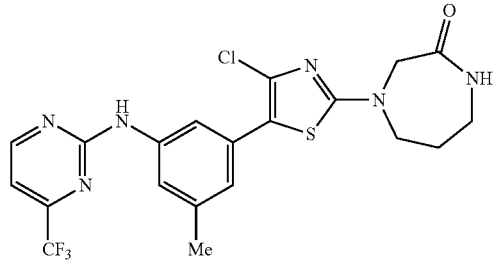 [SMILES: Cc1cc(Nc2nccc(C(F)(F)F)n2)cc(-c2sc(N3CCCNC(=O)C3)nc2Cl)c1]

The title compound was prepared in an analogous manner of that described in Example 227. [M+H]+ Observed: 483.0. rhSYK Activity: +++

EXAMPLE 229

1-[4-(3-{[4-(trifluoromethyl)pyrimidin-2-yl]amino}phenyl)-1,3-thiazol-2-yl]piperidine-4-carboxylic acid

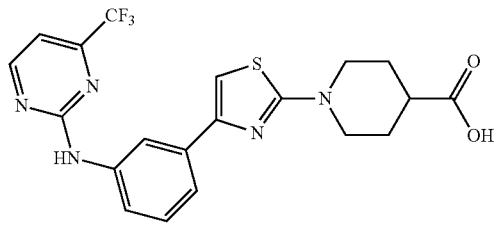 [SMILES: O=C(O)C1CCN(c2nc(-c3cccc(Nc4nccc(C(F)(F)F)n4)c3)cs2)CC1]

Step 1:

A solution of TMS-isothiocyanate (5.4 mL, 38 mmol) and ethyl piperidine-4-carboxylate (5.9 ml, 38 mmol) in tetrahydrofuran (127 ml) was stirred at room temperature for 3 days. The mixture was then diluted with 500 mL ethyl acetate and washed with 500 mL water and 500 mL brine. The aqueous fractions were further extracted with 500 mL ethyl acetate. The combined organic extracts were dried over sodium sulfate and concentrated under reduced pressure. The residue was purified by CombiFlash (40-100% ethyl acetate/hexanes) to provide 1.85 g (7.7 mmol, 20%) of ethyl 1-carbamothioylpiperidine-4-carboxylate as a white solid.

Step 2:

A solution of 2-bromo-1-(3-nitrophenyl)ethanone (621 mg, 2.54 mmol) and ethyl 1-carbamothioylpiperidine-4-carboxylate (500 mg, 2.31 mmol) in ethanol (7.7 mL) was heated to reflux for 16 hours, and then cooled to room temperature. The mixture was concentrated under reduced pressure and the resulting residue purified directly by CombiFlash (0-70% ethyl acetate/hexanes) to provide 457 mg (1.26 mmol, 49% yield) of ethyl 1-[4-(3-nitrophenyl)-1,3-thiazol-2-yl]piperidine-4-carboxylate as a yellow solid.

Step 3:

To a solution of the ethyl 1-[4-(3-nitrophenyl)-1,3-thiazol-2-yl]piperidine-4-carboxylate (457 mg, 1.26 mmol) in ethyl acetae (10 mL) and acetic acetic acid (1 mL) was added 10% palladium on carbon (135 mg, 0.126 mmol) and the mixture was placed under an atmosphere of $H_2$ (balloon). The mixture was stirred for 3 hours was then filtered through celite. The filtrate was concentrated under reduced pressure. The resulting residue was purified by CombiFlash (20-60% ethyl acetate:hexanes) provided 250 mg (0.754 mmol, 60% yield) of ethyl 1-[4-(3-aminophenyl)-1,3-thiazol-2-yl]piperidine-4-carboxylate.

Step 4:

A solution of 2-chloro-4-(trifluoromethyl)pyrimidine (42 mg, 0.23 mmol), ethyl 1-[4-(3-aminophenyl)-1,3-thiazol-2-yl]piperidine-4-carboxylate (76 mg, 0.23 mmol) and 4-methylbenzenesulfonic acid (44 mg, 0.23 mmol) in dioxane (1 mL) was heated to 100° C. overnight. After cooling to room temperature the reaction was concentrated under reduced pressure. The resulting residue was diluted with 30 mL ethyl acetate and washed with 30 mL saturated aqueous sodium bicarbonate and 30 mL brine. The aqueous layers were further extracted with 30 mL ethyl acetate. The combined organic extracts were dried over sodium sulfate and concentrated under reduced pressure. Purification by CombiFlash (10-50% ethyl acetate/hexanes) provided 38 mg (0.08 mmol, 35% yield) of ethyl 1-[4-(3-{[4-(trifluoromethyl)pyrimidin-2-yl]amino}phenyl)-1,3-thiazol-2-yl]piperidine-4-carboxylate as a white solid.

Step 5:

To a solution of ethyl 1-[4-(3-{[4-(trifluoromethyl)pyrimidin-2-yl]amino}phenyl)-1,3-thiazol-2-yl]piperidine-4-carboxylate (38 mg, 0.08 mmol) in tetrahydrofuran (0.5 mL) and methanol (0.5 mL) was added 1M aqueous lithium hydroxide (0.5 mL, 0.5 mmol). The reaction was heated to 50° C. for 2 hours. The mixture was then cooled to room temperature, diluted with 2-methyltetrahydrofuran (30 mL), and washed with 0.1N aqueous hydrochloride acid (30 mL) and brine (30 mL). The aqueous fractions were further extracted with 2-methyltetrahydrofuran (30 mL). The combined organic extracts were dried over sodium sulfate and concentrated under reduced pressure to provide 1-[4-(3-{[4-(trifluoromethyl)pyrimidin-2-yl]amino}phenyl)-1,3-thiazol-2-yl]piperidine-4-carboxylic acid (36 mg, 0.08 mmol, quantitative) as a light blue solid. MS APCI: [M+H]+ m/z 450.1. $^1$H NMR (400 MHz, DMSO): δ 10.23 (s, 1H); 8.82 (d, J=4.9 Hz, 1H); 8.38 (s, 1H); 7.61 (d, J=7.8 Hz, 1H); 7.50 (d, J=7.8 Hz, 1H); 7.32 (t, J=7.8 Hz, 1H); 7.27 (d, J=5.0 Hz, 1H); 7.15 (s, 1H); 6.65 (s, 2H); 3.93 (d, J=12.3 Hz, 2H); 3.22-3.08 (m, 2H); 1.95 (d, J=13.1 Hz, 2H); 1.65 (d, J=14.4 Hz, 2H). rhSyk=++.

EXAMPLE 230

1-[4-(3-{[4-(trifluoromethyl)pyrimidin-2-yl]amino}phenyl)-1,3-thiazol-2-yl]piperidine-4-carboxamide

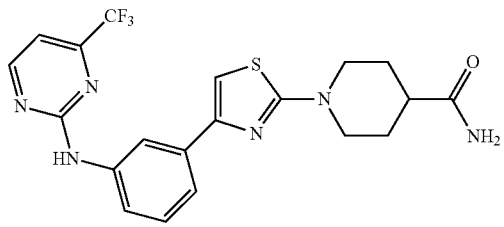 [SMILES: NC(=O)C1CCN(c2nc(-c3cccc(Nc4nccc(C(F)(F)F)n4)c3)cs2)CC1]

To a solution of 1-[4-(3-{[4-(trifluoromethyl)pyrimidin-2-yl]amino}phenyl)-1,3-thiazol-2-yl]piperidine-4-carboxylic acid (36 mg, 0.08 mmol) in N,N-dimethylformamide (0.8 mL) was added ammonium chloride (13 mg, 0.24 mmol), diisopropylethylamine (56 L, 0.32 mmol), and (1H-benzotriazol-1-yloxy)(tripyrrolidin-1-yl)phosphonium hexafluorophosphate (83 mg, 0.16 mmol). The mixture was stirred for 60 minutes at room temperature. The mixture was diluted with ethyl acetate (30 mL), and washed with 1:1 saturated sodium bicarbonate:brine (30 mL), and 1:1 water:brine (30 mL). The aqueous fractions were further extracted with ethyl acetate (30 mL). The combined organic extracts were dried over sodium sulfate and concentrated under reduced pressure. The resulting residue was purified by reverse phase HPLC to provide 8 mg (0.018 mmol, 22% yield) of 1-[4-(3-{[4-(trifluoromethyl)pyrimidin-2-yl]amino}phenyl)-1,3-thiazol-2-yl]piperidine-4-carboxamide as a white solid. MS APCI: [M+H]+ m/z 449.1. $^1$H NMR (400 MHz, DMSO) δ 10.26 (s, 1H), 8.84 (d, J=4.8 Hz, 1H), 8.01 (s, 1H), 7.55-7.51 (m, 2H), 7.35-7.29 (m, 3H), 7.16 (d, J=7.6 Hz, 1H), 6.84 (s, 1H), 3.93 (m, 2H), 3.09 (m, 2H), 2.37 (m, 1H), 1.97-1.70 (m, 2H), 1.62 (m, 2H). rhSyk=++.

EXAMPLE 231/232

1-(4-{3-[(4-methylpyrimidin-2-yl)amino]phenyl}-1,3-thiazol-2-yl)piperidine-4-carboxylic acid 1-(4-({3-[(4-methylpyrimidin-2-yl)amino]phenyl}-1,3-thiazol-2-yl)piperidine-4-carboxamide

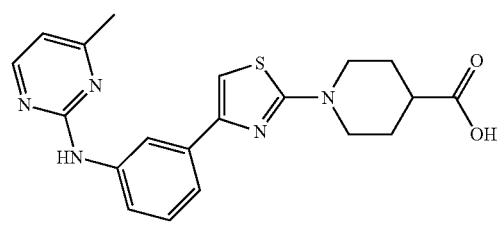

-continued

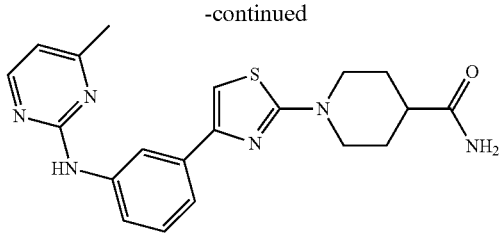

The title compounds were prepared in an analogous manner of that described in Examples 229/230.

| Example | rhSYK Activity | [M + H]+ Obs'd | Form(s) |
|---|---|---|---|
| 231 | ++ | 396.1 | Free Base |
| 232 | ++ | 395.1 | Free Base |

Biological Assay

Homogeneous Time-Resolved Fluorescence (HTRF) Assay for the Recombinant Human SYK Enzyme:

A recombinant GST-hSYK fusion protein was used to measure potency of compounds to inhibit human SYK activity. The recombinant human GST-SYK (Carna Biosciences #08-176) (5 pM final concentration) was incubated with various concentrations of the inhibitor diluted in DMSO (0.1% final concentration) for 10 minutes at room temperature in 15 mM Tris-HCl (pH 7.5), 0.01% tween 20, 2 mM DTT in 384 well plate format. To initiate the reaction the biotinylated substrate peptide (250 nM final concentration) that contains the phosphorylation site for SYK was added with magnesium (5 mM final concentration) and ATP (25 μM final concentration). Final volume of the reaction was 10 μL. Phosphorylation of the peptide was allowed to proceed for 45' at room temperature. To quench the reaction and detect the phosphorylated product, 2 nM of a Europium-atiti-phosphotyrosine antibody (Perkin Elmer #AD0161) and 70 nM SA-APC (Perkin-Elmer #CR130-100) were added together in 15 mM Tris pH 7.5, 40 mM EDTA, 0.01% tween 20. Final volume of the quenching solution was 10 μL. The resulting HTRF signal was measured after 30 minutes on a EnVision (Perkin-Elmer) reader using a time-resolved fluorescence protocol. $IC_{50}$ was determined following 10-dose titration (10 μM to 0.508 nM) and four parameter logistic curve fitting using the Merck Assay Data Analyzer. The rhSYK activity ($IC_{50}$) is expressed as +++ (100 nM or less), ++ (between 100 and 1000 nM), +(between 1 and 10 μM).

What is claimed is:

1. A compound of formula (I) or a pharmaceutically acceptable salt thereof,

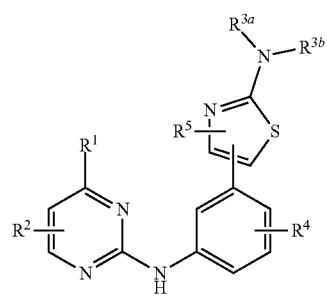

(I)

wherein
$R^1$ is selected from the group consisting of (a) hydrogen, (b) halogen, (c) CN, (d) $C_{1-6}$ alkyl optionally substituted with one or more groups independently selected from the group consisting of $OR^a$ and halogen, (e) $C_{2-6}$ alkenyl, (f) $C_{2-6}$ alkynyl, (g) $C_{3-6}$ cycloalkyl, (h) OH, (i) —O—$C_{1-6}$ alkyl optionally substituted with one or more groups independently selected from (i) aryl, (ii) 5- or 6-membered heteroaryl optionally substituted with one or more groups independently selected from $C_{1-6}$ alkyl, (iii) 4- to 8-membered heterocyclyl optionally substituted with one or more groups independently selected from oxo, halogen, $C_{1-6}$ alkyl, (iv) —$CO_2R^a$, (v) —$CONR^bR^c$, (vi) —$NR^bR^c$, (vii) —NH-heterocycle optionally substituted with alkyl, and (viii) —$OR^a$, (j) —O—X, wherein X is selected from the group consisting of (i) 4- to 8-membered heterocyclyl optionally substituted with one or more groups independently selected from halogen, $C_{1-6}$ alkyl, —$C_{1-6}$ haloalkyl, $COR^a$, $CO_2R^a$, and (ii) $C_{3-6}$ cycloalkyl optionally substituted with one or more groups independently selected from $C_{1-6}$ alkyl, —$OR^a$, benzyl, —$CO_2R^a$, and —$NR^bR^c$, (k) —$S(O)_n$—$C_{1-6}$ alkyl optionally substituted with $OR^a$, (l) —$CO_2R^a$, (m) —$CONR^bR^c$, and (n) —$COR^a$;
$R^2$ is selected from the group consisting of (a) H, (b) halogen, (c) $C_{1-6}$ alkyl, (d) O—$C_{1-6}$ alkyl, (e) $C_{1-6}$ haloalkyl and (f) O—$C_{1-6}$ haloalkyl;
$R^{3a}$ and $R^{3b}$ are independently selected from the group consisting of (a) H, (b) $C_{1-8}$ alkyl optionally substituted with one or more groups independently selected from (i) $OR^a$, (ii) heteroaryl optionally substituted with $C_{1-4}$ alkyl, aryl, (iii) aryl optionally substituted with halogen, $C_{1-4}$ alkyl (optionally substituted with halogen, $CO_2R^a$, $NR^bR^c$), $CO_2R^a$, $OR^a$, $NR^bR^c$, heteroaryl, (iv) $NR^bR^c$, (v) halogen, (vi) heterocyclyl optionally substituted with oxo, $C_{1-4}$ alkyl, $OR^a$, $NR^bR^c$, (vii) $SR^a$, (viii) $C_{3-8}$ cycloalkyl optionally substituted with $OR^a$, $NR^bR^c$, and (ix) $CO_2R^a$, (c) heterocycle optionally substituted with one or more groups independently selected from $OR^a$, (d) $C_{3-8}$ cycloalkyl optionally substituted with one or more groups independently selected from $OR^a$, (e) $C_{3-6}$ alkenyl, (f) heteroaryl optionally substituted with one or more groups independently selected from $C_{1-4}$ alkyl optionally substituted with $NR^bR^c$, (g) —$SO_2R^a$, (h) —$C(O)CH_2OC(O)R^a$, (i) —$C(O)R^a$, (j) —$CO_2R^a$, (k) —$CONR^bR^c$, (l) aryl optionally substituted with $CO_2R^a$, or
$R^{3a}$, $R^{3b}$ and the nitrogen atom to which they are both attached together form a 3- to 8-membered heterocyclic ring having 0-1 additional heteroatom selected from N—$R^x$, O and S;
wherein said ring is optionally substituted with one or more groups independently selected from (a) oxo, (b) $C_{1-4}$ alkyl optionally substituted with (i) $OR^a$, (ii) $NR^bR^c$, (iii) NHC(O)$R^a$, (iv) $NHCO_2R^a$, (v) halogen, (vi) $CO_2R^a$, (vii) $CONR^bR^c$, and (viii) heteroaryl, (c) $OR^a$, (d) heteroaryl optionally substituted with aryl, $C_{1-4}$ alkyl, (e) halogen, (f) aryl optionally substituted with halogen, $SO_2R^a$, (g) —$OCH_2C(O)NHR^b$, (h) $NR^bR^c$, (i) —$C(O)NR^bR^c$, (j) —$CO_2R^a$, or two substituents (including $R^x$) on adjacent ring atoms together with said atoms form a benzene, a $C_{3-8}$cycloalkyl, a 3- to 8-membered heterocycle, or a 5- or 6-membered heteroaryl, each optionally substituted with $R^x$; or two substituents on the same ring atom together with said atom form a $C_{3-8}$cycloalkyl or a 3- to 8-membered heterocycle, each optionally substituted with $R^x$; or $R^{3a}$, $R^{3b}$ and the nitrogen atom to which they are both attached together form a 3- to 8-membered heteroaryl ring having 0-2 additional N, or 0-1 additional N, and 0-1 heteroatom selected from O and S;

$R^4$ is selected from the group consisting of (a) H, (b) halogen, (c) $C_{1-6}$ alkyl, (d) O—$C_{1-6}$ alkyl, (e) $C_{1-6}$ haloalkyl, (f) O—$C_{1-6}$ haloalkyl, (g) OH, (i) $NO_2$, (j) —$NR^bR^c$, (k) $NHC(O)R^a$, (l) $NHC(O)NHR^b$, (m) $NHC(O)NHC(O)NR^bR^c$, (n) $C_{2-6}$ alkenyl, (o) $C_{2-6}$ alkynyl, (p) $C_{3-6}$ cycloalkyl and (q) O-benzyl, $R^5$ is selected from the group consisting of H, halogen and $C_{1-3}$alkyl;

$R^a$ is selected from the group consisting of (a) H, (b) $C_{1-6}$ alkyl optionally substituted with one or more groups independently selected from (i) halogen, (ii) CN, (iii) OH, (iv) —$NR^bR^c$, (v) heterocyclyl optionally substituted with oxo, and (vi) $CO_2H$; and (c) benzyl, $R^b$ and $R^c$ are independently selected from the group consisting of H, $C_{1-6}$ alkyl and $C_{3-6}$cycloalkyl; or $R^b$, $R^c$ and the nitrogen atom to which they are attached together form a 5- or 6-membered heterocycle having 0 or 1 additional heteroatom selected from O, S and N—$R^x$, and optionally substituted with one or more groups independently selected from oxo, $R^x$ is selected from (a) H, (b) —$C(O)C_{1-4}$ alkyl optionally substituted with OH or $OC_{1-4}$ alkyl, (c) —$CO_2C_{1-4}$ alkyl, (d) —$CO_2C_{3-4}$ alkenyl, (e) C(O)-heteroaryl, (f) benzyl, (g) $C_{1-4}$ alkyl optionally substituted with OH, and (h) aryl optionally substituted with $CO_2H$.

2. A compound of claim 1 having the formula (Ia) or a pharmaceutically acceptable salt thereof:

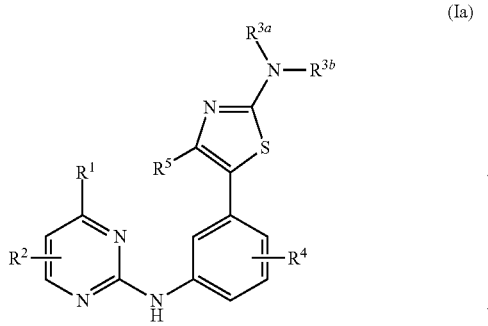

(Ia)

wherein $R^1$, $R^2$, $R^{3a}$, $R^{3b}$, $R^4$ and $R^5$ are as defined in claim 1.

3. A compound of claim 2 or a pharmaceutically acceptable salt thereof, wherein $R^{3a}$ and $R^{3b}$ are independently selected from (a) H, (b) $C_{1-6}$alkyl optionally substituted with one or two groups independently selected from (i) $OR^a$, (ii) phenyl optionally substituted with $OR^a$, $C_{1-3}$ alkyl or $CF_3$, (iii) 5- or 6-membered heterocyclyl optionally substituted with one or two groups selected from oxo, $C_{1-3}$ alkyl, $OR^a$ and $NR^bR^c$, (iv) 5- or 6-membered heteroaryl optionally substituted with one or two methyl groups, (v) $C_{3-6}$cycloalkyl, (vi) $CO_2H$, (vii) $NR^bR^c$, and (viii) $SR^a$, (c) $C_{1-6}$haloalkyl optionally substituted with OH, and (d) $C_{3-6}$cycloalkyl optionally substituted with OH, and (e) phenyl optionally substituted with $CO_2H$ or $CO_2C_{1-4}$alkyl.

4. A compound of claim 3 or a pharmaceutically acceptable salt thereof, wherein $R^{3a}$ is H and $R^{3b}$ is selected from (a) $C_{1-6}$alkyl optionally substituted with one or two groups independently selected from (i) $OR^a$, (ii) phenyl optionally substituted with $OR^a$, $C_{1-3}$ alkyl or $CF_3$, (iii) 5- or 6-membered heterocyclyl optionally substituted with one or two groups selected from oxo, $C_{1-3}$alkyl, $OR^a$ and $NR^bR^c$, (iv) 5- or 6-membered heteroaryl optionally substituted with one or two methyl groups, (v) $C_{3-6}$cycloalkyl, (vi) $CO_2H$, (vii) $NR^bR^c$, and (viii) $SR^a$, and (b) $C_{1-6}$haloalkyl optionally substituted with OH.

5. A compound of claim 2 or a pharmaceutically acceptable salt thereof, wherein $R^{3a}$, $R^{3b}$ and the nitrogen atom to which they are both attached together form a 5- or 6-membered heterocyclic ring having 0-1 additional heteroatom selected from N—$R^x$ and O, wherein said ring is optionally substituted with one or two groups independently selected from (a) oxo, (b) $C_{1-3}$alkyl optionally substituted with OH, $CO_2H$, $CONH_2$, or $NHCOCH_3$, (c) $CF_3$, (d) OH, (e) $CONH_2$, (f) $CO_2H$, and (g) $NH_2$.

6. A compound of claim 5 or a pharmaceutically acceptable salt thereof, wherein $R^{3a}$, $R^{3b}$ and the nitrogen atom to which they are both attached together form a pyrrolidinyl or piperidinyl ring, each being optionally substituted with one or two groups independently selected from (a) oxo, (b) $C_{1-3}$alkyl optionally substituted with OH, $CO_2H$, $CONH_2$, or $NHCOCH_3$, (c) $CF_3$, (d) OH, (e) $CONH_2$, (f) $CO_2H$, and (g) $NH_2$.

7. A compound of claim 1 or a pharmaceutically acceptable salt thereof, having the formula (Ib) or a pharmaceutically acceptable salt thereof:

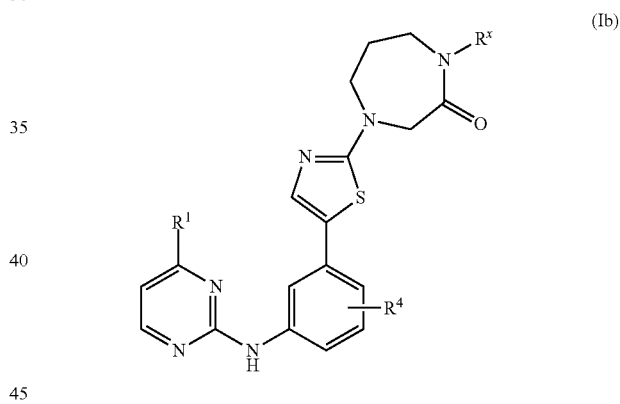

(Ib)

wherein $R^1$, $R^4$ and $R^x$ are as defined in claim 1.

8. A compound of claim 7 or a pharmaceutically acceptable salt thereof, wherein $R^x$ is H.

9. A pharmaceutical composition comprising a therapeutically effective amount of a compound of claim 1 or a pharmaceutically acceptable salt thereof, and a pharmaceutically acceptable carrier.

10. The compound of claim 1 or a pharmaceutically acceptable salt thereof, wherein $R^1$ is trifluoromethyl.

11. The compound of claim 2 or a pharmaceutically acceptable salt thereof, wherein $R^1$ is trifluoromethyl.

12. The compound of claim 7 or a pharmaceutically acceptable salt thereof, wherein $R^1$ is trifluoromethyl.

13. The compound of claim 1 or a pharmaceutically acceptable salt thereof, wherein the compound is 4-[5-(3-methyl-5-{[4-(trifluoromethyl)pyrimidin-2-yl]amino}phenyl)-1,3-thiazol-2-yl]-1,4-diazepan-2-one.

* * * * *